US012569561B2

(12) United States Patent
Park et al.

(10) Patent No.: US 12,569,561 B2

(45) Date of Patent: Mar. 10, 2026

(54) DOUBLE STRANDED OLIGONUCLEOTIDE CONSTRUCT COMPRISING ANDROGEN RECEPTOR SPECIFIC SEQUENCE, AND COMPOSITION FOR PREVENTING HAIR LOSS AND PROMOTING HAIR GROWTH COMPRISING SAME

(71) Applicant: BIONEER CORPORATION, Daejeon (KR)

(72) Inventors: Han-Oh Park, Sejong-si (KR); Sung Il Yun, Daejeon (KR); Sang-Jin Byun, Daejeon (KR); Myeong-Mi Lee, Jeju-do (KR); Seung Ya Yang, Gyeonggi-do (KR)

(73) Assignee: BIONEER CORPORATION, Daejeon (KR)

(*) Notice: Subject to any disclaimer, the term of this patent is extended or adjusted under 35 U.S.C. 154(b) by 722 days.

(21) Appl. No.: 17/297,193

(22) PCT Filed: Nov. 18, 2019

(86) PCT No.: PCT/KR2019/015723

§ 371 (c)(1),
(2) Date: Jun. 30, 2021

(87) PCT Pub. No.: WO2020/111614

PCT Pub. Date: Jun. 4, 2020

(65) Prior Publication Data

US 2022/0118093 A1 Apr. 21, 2022

(30) Foreign Application Priority Data

Nov. 28, 2018 (KR) ........................ 10-2018-0149562

(51) Int. Cl.

*A61K 31/713* (2006.01)
*A61K 8/60* (2006.01)

(Continued)

(52) U.S. Cl.

CPC .............. *A61K 47/26* (2013.01); *A61K 8/606* (2013.01); *A61K 8/8176* (2013.01); *A61K 8/84* (2013.01);

(Continued)

(58) Field of Classification Search

CPC ............ A61K 31/713; A61K 47/58–60; A61K 8/606; A61K 2800/413; A61Q 7/00; A61P 17/14

See application file for complete search history.

(56) References Cited

U.S. PATENT DOCUMENTS

| | | | |
|---|---|---|---|
| 5,660,985 | A | 8/1997 | Pieken |
| 5,808,023 | A | 9/1998 | Sanghvi et al. |

(Continued)

FOREIGN PATENT DOCUMENTS

| | | | |
|---|---|---|---|
| CA | 2761749 | A1 | 11/2010 |
| CA | 2761749 | C | 11/2010 |

(Continued)

OTHER PUBLICATIONS

Aug. 10, 2022 Office Action in corresponding Canadian patent Application 3121472.

(Continued)

*Primary Examiner* — Terra C Gibbs

(74) *Attorney, Agent, or Firm* — HULTQUIST, PLLC; Steven J. Hultquist

(57) ABSTRACT

Disclosed are a double stranded oligonucleotide construct, configured such that a hydrophilic material and a hydrophobic material are conjugated through a simple covalent bond or a linker-mediated covalent bond to both ends of a double stranded oligonucleotide in order to efficiently deliver an androgen-receptor-specific oligonucleotide into a cell, a nanoparticle capable of being produced by self-assembling double stranded oligonucleotide constructs in an aqueous (Continued)

solution through hydrophobic interactions, and a composition for preventing hair loss or promoting hair growth containing the double stranded oligonucleotide construct. The double stranded oligonucleotide construct including the androgen-receptor-specific oligonucleotide and the composition for preventing hair loss or promoting hair growth containing the same as an active ingredient can suppress the expression of an androgen receptor with high efficiency without side effects, and can thus exhibit excellent effects on preventing hair loss, particularly androgenetic alopecia, alopecia areata, and telogen effluvium, and promoting hair growth.

21 Claims, 5 Drawing Sheets

Specification includes a Sequence Listing.

(51) Int. Cl.

| | |
|---|---|
| ***A61K 8/81*** | (2006.01) |
| ***A61K 8/84*** | (2006.01) |
| ***A61K 8/86*** | (2006.01) |
| ***A61K 8/88*** | (2006.01) |
| ***A61K 47/26*** | (2006.01) |
| ***A61K 47/58*** | (2017.01) |
| ***A61K 47/59*** | (2017.01) |
| ***A61K 47/60*** | (2017.01) |
| ***A61P 17/14*** | (2006.01) |
| ***A61Q 7/00*** | (2006.01) |

(52) U.S. Cl.

CPC .................. *A61K 8/86* (2013.01); *A61K 8/88* (2013.01); *A61K 31/713* (2013.01); *A61K 47/58* (2017.08); *A61K 47/59* (2017.08); *A61K 47/595* (2017.08); *A61K 47/60* (2017.08); *A61P 17/14* (2018.01); *A61Q 7/00* (2013.01); *A61K 2800/413* (2013.01); *A61K 2800/57* (2013.01)

(56) References Cited

U.S. PATENT DOCUMENTS

| | | | | |
|---|---|---|---|---|
| 5,958,691 A | 9/1999 | Pieken et al. | | |
| 6,175,001 B1 | 1/2001 | Barbas et al. | | |
| 6,326,358 B1 | 12/2001 | Manoharan | | |
| 6,531,584 B1 | 3/2003 | Cook et al. | | |
| 8,927,515 B2 * | 1/2015 | Brown | ............... | C12N 15/1138<br>435/375 |
| 2007/0141009 A1 | 6/2007 | Kahn | | |
| 2016/0122764 A1 * | 5/2016 | Chae | ....................... | A61P 11/10<br>536/24.5 |

FOREIGN PATENT DOCUMENTS

| | | | |
|---|---|---|---|
| CN | 101054579 | A | 10/2007 |
| CN | 105705639 | A | 6/2016 |
| JP | 2011148798 | A | 8/2011 |
| JP | 2012-526548 | A | 11/2012 |
| JP | 2013534424 | A | 9/2013 |
| JP | 2016530875 | A | 10/2016 |
| KR | 10-0883471 | B1 | 2/2009 |
| KR | 10-2012-0080562 | A | 7/2012 |
| KR | 10-1224828 | B1 | 1/2013 |
| KR | 1020150006743 | A | 1/2015 |
| KR | 1020160033125 | A | 3/2016 |
| KR | 101862349 | B1 | 5/2018 |

OTHER PUBLICATIONS

Aug. 18, 2022 Office Action in corresponding Japanese Patent Application 2021-530850.

English Translation of Aug. 18, 2022 Office Action in corresponding Japanese Patent Application 2021-530850.

Sep. 5, 2022 Notice of Allowance in corresponding Korean Patent Application 10-2018-0149562.

English Translation of Sep. 5, 2022 Notice of Allowance in corresponding Korean Patent Application 10-2018-0149562.

Akhtar, S., et al., "Nonviral delivery of synthetic siRNAs in vivo", The Journal of Clinical Investigation, Dec. 2007, pp. 3623-3632, vol. 117, No. 12, Publisher: http://www.jci.org.

Amarzguioui, M., et al., "Tolerance for mutations and chemical modifications in a siRNA", Nucleic Acide Research, 2003, pp. 589-595, vol. 31, No. 2, Publisher: Oxford University Press.

Barik, S., "Silence of the transcripts: RNA interference in medicine", J Mol Med, 2005, pp. 764-773, vol. 83, Publisher: Springer-Verlag 2005.

Behlke, M., "Progress Towards in Vivo Use of siRNAs", Molecular Therapy, Apr. 2006, pp. 644-670, vol. 13, No. 4, Publisher: The American Society of Gene Therapy.

Bertrand, J-R, et al., "Comparison of antisense oligonucleotides and siRNAs in cell culture and in vivo", Biochemical and Biophysical Communications, 2002, pp. 1000-1004, vol. 296.

Braasch, D., et al., "Biodistribution of phosphodiester and phoshorothioate siRNA", Bioorganic & Medicinal Chemistry Letters, 2004, pp. 1139-1143, vol. 14, Publisher: Elsevier.

Bramsen, J.B., et al., "A screen of chemical modifications identifies position-specific modification by UNA to most potently reduce siRNA off-target effects", Nucleic Acids Research, 2010, pp. 5761-5773, vol. 38, No. 17, Publisher: Oxford University Press.

Chiu, Y-L, et al., "siRNA function in RNAi: A chemical modification analysis", RNA, 2003, pp. 1034-1048, vol. 9, Publisher: Cold Spring Harbor Laboratory Press.

Crooke, S., "Progress in Antisense Technology", Annu. Rev. Med., 2004, pp. 61-95, vol. 55, Publisher: Annual Reviews.

Dallob, A.L., et al., "The Effect of Finasteride, a 5-Reductase Inhibitor, on Scalp Skin Testerone and Dihydrotestosterone Concentrations in Patients with Male Pattern Baldness", Journal of Clinical Endocrinology and Metabolism, 1994, pp. 703-709, vol. 79, No. 3, Publisher: The Endocrine Society.

Ellsworth, K., et al., "Expression of the Type 1 and 2 Steroid 5-Reductases in Human Fetal Tissues", Biochemical and Biophysical Communications, Oct. 13, 1995, pp. 774-780, vol. 215, No. 2, Publisher: Academic Press, Inc.

Kaufman, K.D., "Androgens and alopecia", Molecular and Cellular Endocrinology, 2002, pp. 89-05, vol. 198, Publisher: Elsevier.

Naito, A., et al., "Dihydrotestosterone inhibits murine hair growth via the androgen receptor", British Journal of Dermatology, , pp. 300-305, vol. 159, Publisher: 2008 British Association of Dermatologists.

NCBI, "*Homo sapiens* androgen receptor (AR), transcript variant 1, mRNA", GenBank, 7/0/2016, vol. NM_000044.3.

Opalinska, J., et al., "Nucleic-Acid Therapeutics: Basic Principles and Recent Applications", Nature Reviews Drug Discovery, 2002, pp. 503-514, vol. 1.

Shigeta, K., et al., "Novel histidine-conjugated galactosylated cationic liposomes for efficient hepatocyte-selective gene transfer in human hepatoma HepG2 cells", Journal of Controlled Release, 2007, pp. 262-270, vol. 118, Publisher: Elsevier.

Vaish, N., et al., "Improved specificity of gene silencing by siRNAs containing unlocked nucleobase analogs", Nucleic Acids Research, 2011, pp. 1823-1832, vol. 39, No. 5, Publisher: Oxford University Press.

Veronese, F., "Peptide and protein PEGylation: a review of problems and solutions", Biomaterials, 2001, pp. 405-417, vol. 22, Publisher: Elsevier.

Veronese, F.M., et al., "PEGylation, successful aproach to drug delivery", Drug Discovery Today, Dec. 2005, pp. 1451-1458, vol. 10, No. 21, Publisher: Elsevier.

Xie, F., et al., "Harnessing in vivo siRNA delivery for drug discovery and therapeutic development", Drug Discovery Today, 2006, pp. 67-73, vol. 11, No. 1/2, Publisher: Elsevier.

Zelphati, O., et al., "Mechanism of oligonucleotide release from cationic liposomes", Biochemistry, Oct. 1996, pp. 11493-11498, vol. 93, Publisher: Proc. Natl. Acad. Sci. USA.

(56) References Cited

OTHER PUBLICATIONS

Cheng, M., et al., "The role of androgen and its receptor in androgenetic alopecia", Journal of Military Surgeon in Southwest China, 2017, pp. 335-338, vol. 19, No. 4.
Cheng, M., et al., English translation of "The role of androgen and its receptor in androgenetic alopecia", Journal of Military Surgeon in Southwest China, 2017, pp. 335-338, vol. 19, No. 4.
Office Action issued in Chinese Patent Application No. 201980087853.4 on Jun. 1, 2023.
Search Report issued in Chinese Patent Application No. 201980087853.4 on May 30, 2023.
English Translation of Office Action issued in Chinese Patent Application No. 201980087853.4 on Jun. 1, 2023.

* cited by examiner

1st screening result among 544 types of SAMi-hAR (50nM, Lipofectamine)

$2^{nd}$ screening results for SAMi-hAR subject to NLCap

DOUBLE STRANDED OLIGONUCLEOTIDE CONSTRUCT COMPRISING ANDROGEN RECEPTOR SPECIFIC SEQUENCE, AND COMPOSITION FOR PREVENTING HAIR LOSS AND PROMOTING HAIR GROWTH COMPRISING SAME

REFERENCE TO SEQUENCE LISTING SUBMITTED VIA PATENT CENTER

This application includes an electronically submitted sequence listing in .txt format. The .txt file contains a sequence listing entitled "564_UpdatedSeqListing_ST25.txt" created on Apr. 30, 2024 and is 125,577 bytes in size. The sequence listing contained in this .txt file is part of the specification and is hereby incorporated by reference herein in its entirety.

TECHNICAL FIELD

The present invention relates to a double stranded oligonucleotide construct including an androgen-receptor-specific sequence and a composition for preventing hair loss and promoting hair growth containing the same, and more particularly to a double stranded oligonucleotide construct configured such that a hydrophilic material and a hydrophobic material are conjugated through a simple covalent bond or a linker-mediated covalent bond to both ends of a double stranded oligonucleotide in order to efficiently deliver a nucleotide of an androgen-receptor-specific sequence into a cell, a nanoparticle capable of being produced by self-assembling double stranded oligonucleotide constructs in an aqueous solution through hydrophobic interactions, and a composition for preventing hair loss and promoting hair growth containing the double stranded oligonucleotide construct.

BACKGROUND ART

Hair plays an important role in body protection and external beauty, and the purpose of managing hair is to protect the scalp, maintain a healthy hair condition, improve one's appearance, and the like. Hair loss is the natural loss of hair that has stopped growing depending on the growth cycle, and in general, severe hair loss has been recognized as a genetic phenomenon that occurs mainly in men. In recent years, however, the importance of environmental factors has emerged, such as hair loss due to work stress, environmental pollution, exposure to harmful environments, and incorrect eating habits, and alopecia has been recognized as a disease that refers to a condition where there is no hair in areas where hair should exist. Alopecia is classified into scarring alopecia, in which hair follicles are destroyed and replaced with fibrous tissue, resulting in permanent hair loss, and non-scarring alopecia, in which the tissue is not fibrous and the hair follicles are preserved. Examples of non-scarring alopecia include telogen effluvium, hereditary androgenetic alopecia, alopecia areata, and anagen effluvium.

Hair undergoes a so-called "hair cycle" including a growing stage, a degenerating stage, a resting stage, and an exogen stage, over time. The lifespan of the growing stage is usually 2 to 8 years, accounting for about 90% of all hair at one time, and the division of hair germinal matrix cells continues in the lower half of the hair bulb in contact with the dermal papilla, resulting in hair. After the growing stage, there comes a period in which hair growth stops for a while, which is called a degenerating stage. This is the time to transition to a resting stage in which the hair generation and development stop, during which the roots of the hair also change, the activity of the hair germinal matrix cells and pigment cells stops, and keratin is not produced, so the growth of the hair is stopped. In the resting stage, the hair bulb contracts, and the hair falls out only in the exogen stage, during which proteases are known to be involved. It is thought that androgen, estrogen, thyroid hormone, steroid, prolactin, and growth hormone may be involved as factors that control hair growth, among which androgen is known as the most important regulator. The most common example of hormone-related hair loss is temporary hair loss after childbirth. During pregnancy, estrogen increases and the progression from the growing stage to the resting stage in the hair cycle is suppressed, and then estrogen decreases rapidly after childbirth, and the progression to the resting stage accelerates, resulting in telogen effluvium. In this way, there is hormone-dependent alopecia, but other causes of hair loss include genetic factors, male hormones, aging, blood circulation disorders, stress, superoxide radicals, etc. Here, countermeasures may vary depending on these causes. For hair loss caused by male hormones, DHT blockers are used as a medicine, and the basic mechanism of the blocker is to prevent the conversion of testosterone into highly active dihydrotestosterone (DHT) by 5-α-reductase. Since DHT has at least 5 times higher ability to bind to an androgen receptor (AR) than testosterone, the protein synthesis of hair follicles is delayed, so a substance that blocks the binding to an androgen receptor by preventing overproduction of DHT is used as a medicine (Dallob A. L. et al., 1994. *J. Clin. Endocrinol. Metab.* 79, 703-709; Ellsworth, K and Harris G., 1995, *Biochem. Biophys. Res. Commun.* 215, 774-780; Kaufman K D., 2002. *Mol and Cell Endocrinology.* 198, 85-89).

In 1942, Hamilton revealed the relationship between hair loss and male hormones. In androgenetic alopecia (AGA), testosterone present in hair root cells is converted into DHT, which is a powerful metabolite, and DHT (dihydrotestosterone) binds to an androgen receptor (AR) in hair follicles, so the activity of adenyl cyclase, which enhances intracellular metabolism, is inhibited, whereby the concentration of cAMP in the cells is lowered and sugar metabolism is decreased, and consequently, energy supply is inhibited and protein synthesis is delayed, which shortens the growing stage of hair follicles, and during the process of repeating this phenomenon, the proportion of hair follicles in the resting stage increases, causing the hair to gradually become thin and short. Briefly, it is known that testosterone present in hair root cells, a DHT receptor, which is a hormone component associated with overexpression of the androgen receptor, and the activity of 5-α-reductase are important for the occurrence of androgenetic alopecia, and also that testosterone is overproduced into dihydrotestosterone (DHT) by 5-α-reductase, and this metabolite stimulates the production of hair cycle inhibitors to thereby shorten the growing stage and inhibit the ability of hair follicles to produce hair (Kaufman K D., 2002. *Mol. and Cell. Endocrinology.* 198, 89-85; Naito et al., 2008. *Br. J. Dermatol.* 159, 300-305).

DHT is known to have at least 5 times higher ability than testosterone to bind to an androgen receptor (AR), and in androgen-specific cells and tissues, DHT is known to be more involved in androgen activity than testosterone. There are two subtypes of 5-α-reductase, which is responsible for these metabolic processes, and the roles thereof are somewhat different depending on the tissue. Type 1 5-α-reductase is present in the sebaceous gland, and Type 2 5-α-reductase is mainly present in the genitourinary tract and hair follicles.

Finasteride and dutasteride are drugs that target 5-α-reductase in order to suppress the overproduction of DHT, and it is known that finasteride acts only on Type 2 5-α-reductase and dutasteride acts on Type 1 and Type 2 5-α-reductases to thus have great effects on prostate-related diseases. Among these, the drug that has been approved by the FDA as a therapeutic agent for baldness is Propecia, which contains finasteride as a main ingredient. Hair-loss prevention medicines developed to date are mainly single compounds, such as minoxidil for promoting blood circulation and finasteride and dutasteride as male hormone inhibitors, and recently, drugs for JAK inhibitors (ruxolitinib, tofacitinib) have been approved by the FDA. However, research to find a material that is more effective than the above materials is continuously ongoing.

The androgen receptor is a 110 KDa steroidal receptor, and one of the important functions thereof is the transcription of genes related to androgens. The androgen receptor plays an important role in male-hormone-related diseases such as prostate cancer, prostatic hyperplasia, male pattern alopecia, muscle loss, and hypertrichosis. For this reason, the androgen receptor has been used as a target for the treatment of male-specific diseases such as prostate cancer and male pattern baldness. In the case of male hormones collectively referred to as androgens, testosterone is produced in the pituitary gland, adrenal gland, and testes, enters the cells of the target organ, and is reduced into dihydrotestosterone (DHT) by testosterone 5-α-reductase, followed by binding to the receptor and showing the action as an androgen. Therefore, as mentioned above, the development of a therapeutic agent for the disease is being sought using a method of suppressing the production of DHT by inhibiting the action of 5-α-reductase for reducing testosterone into DHT, or a method of suppressing the action of androgen by inhibiting the binding of DHT, produced from testosterone, to the receptor.

Technology for inhibiting gene expression is regarded as important in the development of therapeutic agents for disease treatment and in target verification. In particular, RNA interference (hereinafter referred to as 'RNAi') has been found to act on sequence-specific mRNA in various kinds of mammalian cells since the role thereof was discovered (Silence of the transcripts: RNA interference in medicine. J Mol Med (2005) 83: 764-773). When a long-chain RNA double strand is delivered to cells, the delivered RNA double strand is processed by an endonuclease called dicer and converted into small interfering RNA (hereinafter referred to as 'siRNA') of 21 to 23 double strands (base pair, bp), and siRNA binds to the RNA-induced silencing complex (RISC), and thus a guide (antisense) strand recognizes and degrades the target mRNA to thereby inhibit the expression of the target gene in a sequence-specific manner (NUCLEIC-ACID THERAPEUTICS: BASIC PRINCIPLES AND RECENT APPLICATIONS. Nature Reviews Drug Discovery. 2002. 1, 503-514).

According to Bertrand researchers, it has been reported that siRNA for the same target gene has a superior inhibitory effect on the expression of mRNA in vitro and in vivo compared to the antisense oligonucleotide (ASO), and that the effect is long-lasting (Comparison of antisense oligonucleotides and siRNAs in cell culture and in vivo. Biochem. Biophys. Res. Commun. 2002. 296: 1000-1004). Moreover, the mechanism of action of siRNA is that siRNA binds complementarily to target mRNA to regulate the expression of the target gene in a sequence-specific manner, and compared to existing antibody-based drugs or chemical drugs (small-molecule drugs), it has the advantage that the range of applicable targets can be dramatically expanded (Progress Towards in Vivo Use of siRNAs. MOLECULAR THERAPY. 2006 13(4):664-670).

In spite of the excellent effect and wide range of use of siRNA, in order to develop siRNA as a therapeutic agent, siRNA has to be effectively delivered to target cells by improving the stability of siRNA in the body and increasing cell delivery efficiency (Harnessing in vivo siRNA delivery for drug discovery and therapeutic development. Drug Discov. Today. 2006 January; 11(1-2):67-73).

With the goal of solving the above problem, thorough research is ongoing into modification of some nucleotides or backbones of siRNA to impart nuclease resistance thereto in order to improve the stability thereof in the body, and into the use of carriers such as viral vectors, liposomes or nanoparticles.

Delivery systems using viral vectors such as an adenovirus or retrovirus have high transfection efficacy, but high immunogenicity and oncogenicity. On the other hand, a non-viral delivery system containing nanoparticles has lower cell delivery efficiency than a viral delivery system, but it is advantageous because high stability in vivo, the potential for target-specific delivery, an improved delivery effect, such as uptake and internalization of the contained RNAi oligonucleotides into cells or tissues, and almost no cytotoxicity or immune stimulation, so it is currently considered a more powerful delivery method than the viral delivery system (Nonviral delivery of synthetic siRNAs in vivo. J Clin Invest. 2007 Dec. 3; 117(12): 3623-3632).

As for the method of using a nanocarrier in the non-viral delivery system, nanoparticles are formed using various polymers such as liposomes, cationic polymer complexes and the like, and siRNA is loaded on such a nanoparticle, namely a nanocarrier, and is delivered to cells. Among the methods of using a nanocarrier, a polymeric nanoparticle, polymer micelle, lipoplex, etc. may be mainly used, and in particular, the lipoplex is composed of cationic lipids and interacts with the anionic lipids of the endosome of the cell, causing the effect of destabilization of the endosome to thus enable intracellular delivery (Proc. Natl. Acad. Sci. 15; 93(21):11493-8, 1996).

In order to improve the intracellular delivery efficiency of siRNA, technology for attaining the stability of siRNA and efficient cell membrane permeability has been developed using an siRNA conjugate in which a hydrophilic material (e.g. polyethylene glycol (PEG)) as a biocompatible polymer is conjugated to siRNA through a simple covalent bond or a linker-mediated covalent bond (Korean Patent No. 883471). However, chemical modification of siRNA and conjugation of polyethylene glycol (PEG) (PEGylation) still have the drawbacks such as low stability in vivo and inefficient delivery to target organs. In order to solve these drawbacks, a double stranded oligonucleotide construct, in which hydrophilic and hydrophobic materials are bound to an oligonucleotide, particularly a double stranded oligonucleotide such as siRNA, has been developed, and the construct forms self-assembled nanoparticles called SAMiRNA™ (self-assembled micelle inhibitory RNA) through the hydrophobic interaction of the hydrophobic material (Korean Patent No. 1224828). The SAMiRNA™ technology has the advantage of being able to obtain homogenous nanoparticles while being very small in size compared to conventional delivery technologies.

As for a specific example of SAMiRNA™ technology, PEG (polyethylene glycol) or HEG (hexaethylene glycol) is used as a hydrophilic material, and PEG is a synthetic polymer and is often used to increase the solubility of pharmaceuticals, particularly proteins, and to control pharmacokinetics. PEG is a polydisperse material, and a batch of polymers is composed of the total sum of different numbers of monomers, and has a Gaussian molecular weight distribution, and the extent of homogeneity of a material is expressed as a polydispersity index (Mw/Mn). Specifically, when PEG has a low molecular weight (3-5 kDa), it exhibits a polydispersity index of about 1.01, whereas the case of a high molecular weight (20 kDa) shows a high polydispersity index of about 1.2, and thus the higher the molecular weight, the lower the homogeneity of the material (F. M. Veronese. Peptide and protein PEGylation: a review of problems and solutions. Biomaterials (2001) 22:405-417). Therefore, the case in which PEG is bound to a pharmaceutical is disadvantageous in that it is not easy to verify a single material because the polydispersity characteristic of PEG is reflected in the conjugate. Hence, there is a trend to produce materials having a low polydispersity index by improving the processes for synthesis and purification of PEG. In particular, in the case in which PEG is bound to a material having a low molecular weight, there are problems due to the polydispersity characteristics of the material, such as an inconvenient point in which it is not easy to check whether binding is easily achieved (Francesco M. Veronese and Gianfranco Pasut. PEGylation, successful approach to drug delivery. DRUG DISCOVERY TODAY (2005) 10(21):1451-1458).

Accordingly, in recent years, as an improved form of the existing self-assembled nanoparticles SAMiRNA™, the hydrophilic material of the double stranded nucleotide construct constituting the SAMiRNA™ is blocked into a basic unit including 1 to 15 homogeneous monomers having a certain molecular weight, and, as necessary, a linker, and by using an appropriate number of blocks depending on the need, a new form of delivery carrier technology has been developed that has a smaller size than that of the existing SAMiRNA™ and has significantly improved polydispersity.

Meanwhile, there is a report that the global market related to hair loss will reach $11.8 billion by 2024 (Grand View Research, Inc). Four in seven American men and one in five Chinese men are bald, and in 90% or more of cases, the cause is known to be androgenetic alopecia. However, most hair-loss prevention medicines developed to date target DHT and 5-α-reductase, and a medicine or hair growth product targeting the androgen receptor, which is directly related to androgen, has not been developed.

Accordingly, the present inventors have made great efforts to develop a hair-growth-related product targeting the androgen receptor, which is directly related to androgen, and ascertained that a certain sequence specific to an androgen receptor may effectively inhibit the expression of the androgen receptor, and that a double stranded oligonucleotide construct including the same and a composition containing the construct are very effective at preventing hair loss or promoting hair growth, thus culminating in the present invention.

DISCLOSURE

It is an object of the present invention to provide a novel oligonucleotide sequence that is specific to an androgen receptor and is capable of inhibiting the expression thereof with very high efficiency, and a double stranded oligonucleotide construct for effectively delivering the sequence to hair root cells.

It is another object of the present invention to provide a nanoparticle containing the double stranded oligonucleotide construct.

It is still another object of the present invention to provide a pharmaceutical composition for preventing hair loss or promoting hair growth containing the novel oligonucleotide sequence or the double stranded oligonucleotide construct as an active ingredient.

It is yet another object of the present invention to provide a cosmetic composition for preventing hair loss or promoting hair growth containing the novel oligonucleotide sequence or the double stranded oligonucleotide construct as an active ingredient.

In accomplish the above and other objects, the present invention provides a double stranded oligonucleotide construct having the structure of Structural Formula (1) below.

A-X—R—Y—B    Structural Formula (1)

In Structural Formula (1), A is a hydrophilic material, B is a hydrophobic material, each of X and Y independently represents a simple covalent bond or a linker-mediated covalent bond, and R represents an androgen-receptor-specific oligonucleotide including a sense strand containing any one sequence selected from the group consisting of SEQ ID NOS: 6, 58, 68, 99, 107, 109, 260, 270, 284, 298, 348, 358, 359 and 434 and an antisense strand including a sequence complementary thereto.

In addition, the present invention provides a nanoparticle containing the double stranded oligonucleotide construct.

In addition, the present invention provides a pharmaceutical composition for preventing hair loss or promoting hair growth containing the double stranded oligonucleotide construct or the nanoparticle as an active ingredient.

In addition, the present invention provides a cosmetic composition for preventing hair loss or promoting hair growth containing the double stranded oligonucleotide construct or the nanoparticle as an active ingredient.

In addition, the present invention provides a method of treating hair loss including administering the construct, nanoparticle, or pharmaceutical composition according to the present invention to a subject in need of hair growth, or applying the construct, nanoparticle, or pharmaceutical composition according to the present invention onto an area in need of hair growth.

In addition, the present invention provides a method of preventing hair loss or promoting hair growth containing administering or applying the construct, nanoparticle, or cosmetic composition according to the present invention to a subject in need of hair-loss prevention or hair growth or onto the corresponding area.

In addition, the present invention provides the use of the double stranded oligonucleotide construct to prevent hair loss or to promote hair growth.

In addition, the present invention provides the use of the double stranded oligonucleotide construct to manufacture a medicine or a cosmetic for preventing hair loss or promoting hair growth.

Figure 1:
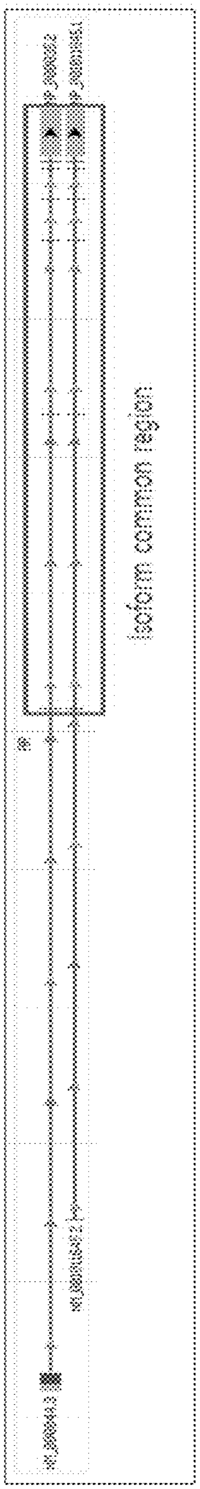
FIG. 1 shows an isoform common region in the exon map of human androgen receptor mRNA NM_000044.3 (isoform 1, 10,661 bp) and NM_001011645.2 (isoform 2, 8112 bp) for a human androgen-receptor-specific oligonucleotide candidate sequence design.
Figure 2:
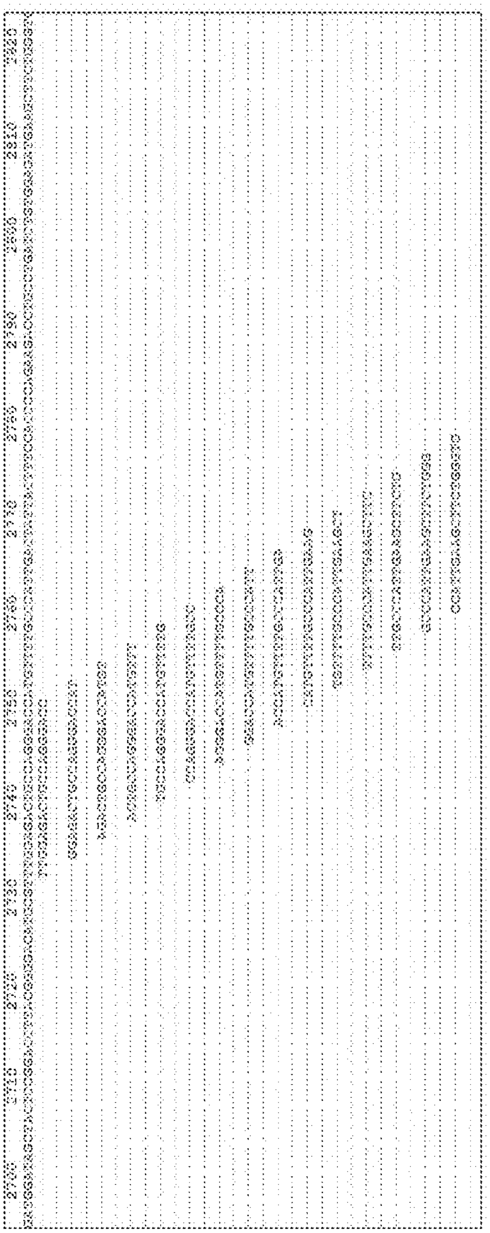
FIG. 2 shows a process of selecting candidate sequences composed of 19 bases using a 2-base sliding-window algorithm in the isoform common region for a human androgen-receptor-specific oligonucleotide candidate sequence design, wherein the following sequences are shown.
Figure 3:
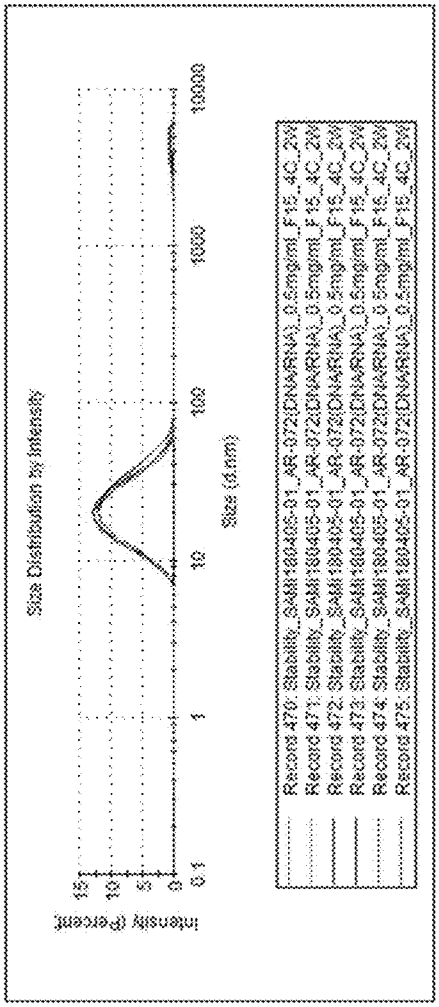
Figure 4:
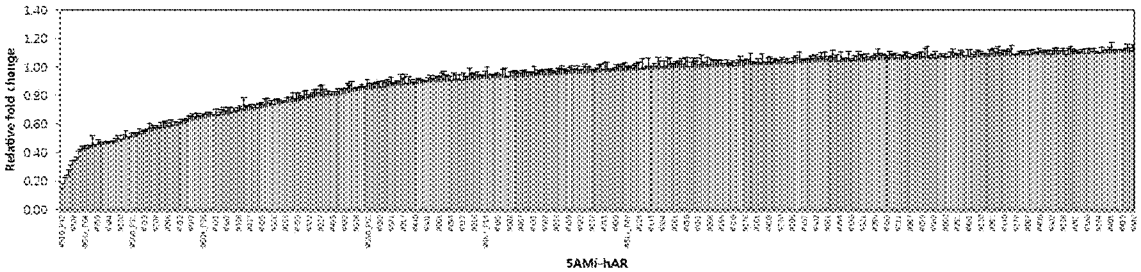
Figure 5:
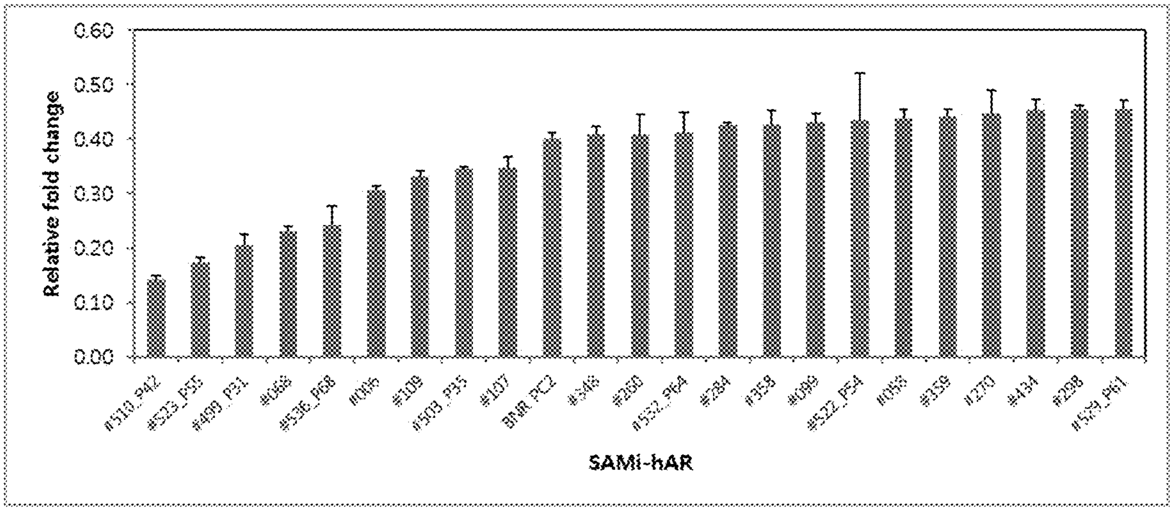
Figure 6:
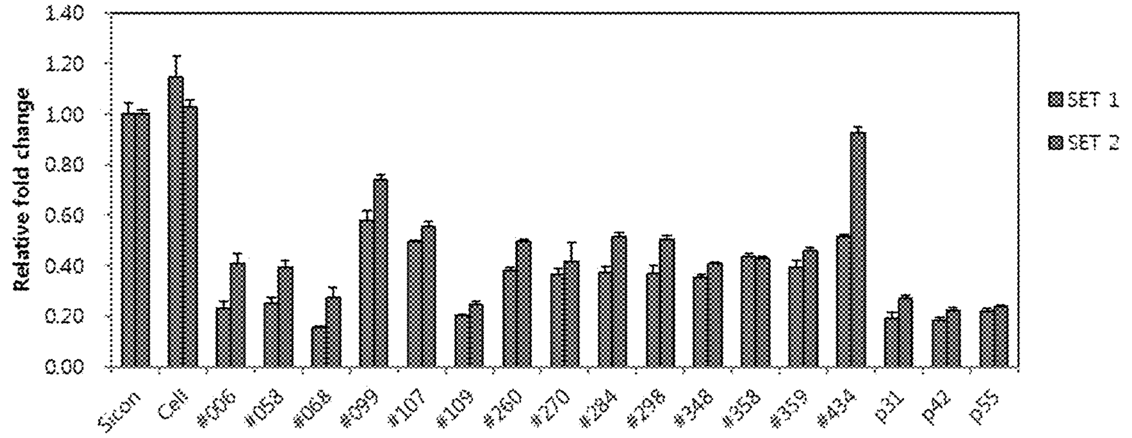
Figure 7:
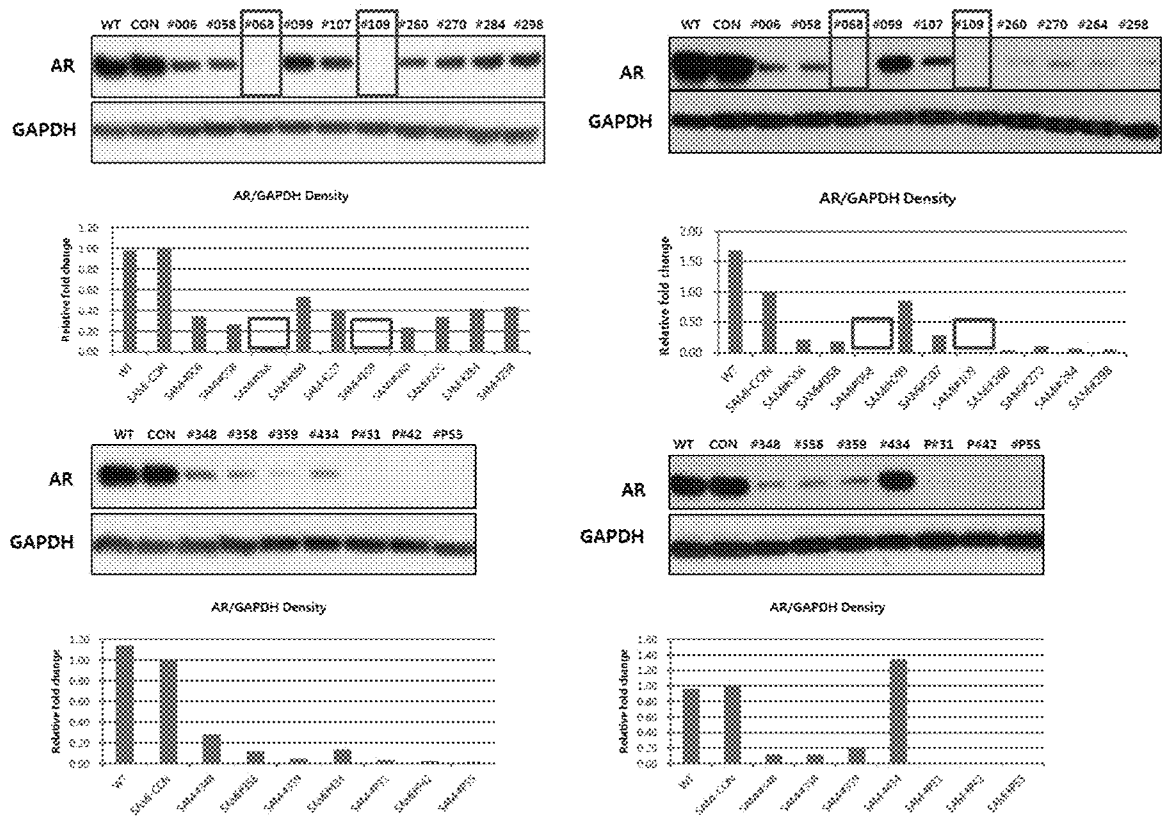
Figure 8:
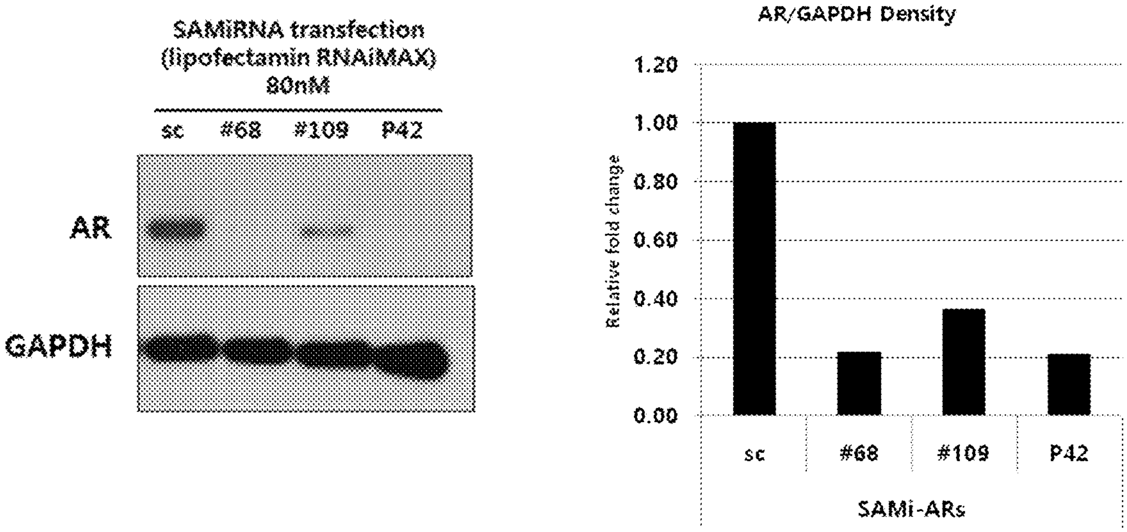
Figure 9:
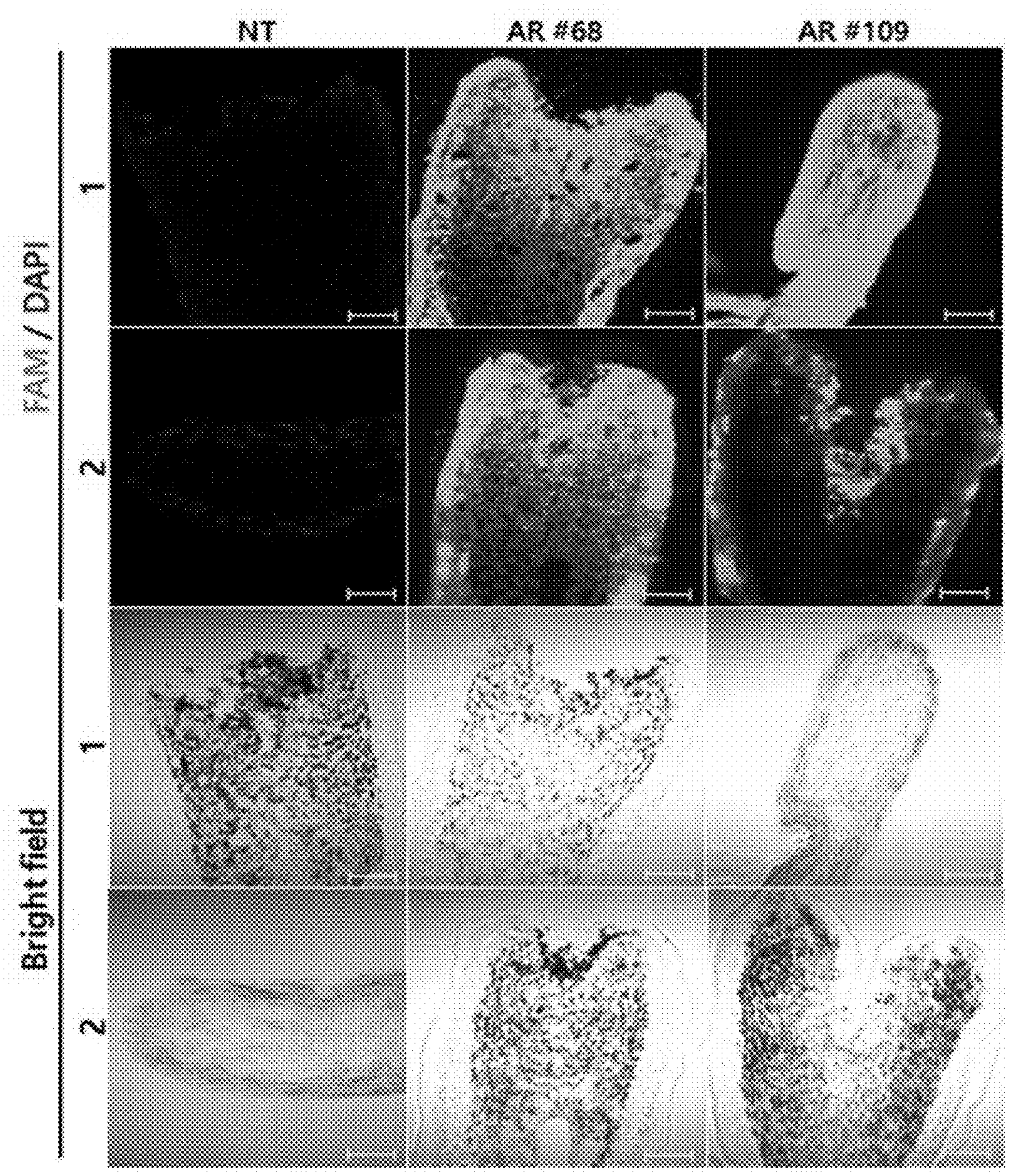

(SEQ ID NO: 546)
GATGGATAGCTACTCCGGACCTTACGGGGACATGCGTTTGGAGACTGCC
AGGGACCATGTTTTGCCCATTGACTATTACTTTCCACCCCAGAAGACCT
GCCTGATCTGTGGAGATGAAGCTTCTGGGTG;

(SEQ ID NO: 547)
TTGGAGACTGCCAGGGACC;

(SEQ ID NO: 548)
GGAGACTGCCAGGGACCAT;

(SEQ ID NO: 549)
AGACTGCCAGGGACCATGT;

(SEQ ID NO: 549)
AGACTGCCAGGGACCATGT;

(SEQ ID NO: 550)
ACTGCCAGGGACCATGTTT;

(SEQ ID NO: 551)
TGCCAGGGACCATGTTTTG;

(SEQ ID NO: 552)
CCAGGGACCATGTTTTGCC;

(SEQ ID NO: 553)
AGGGACCATGTTTTGCCCA;

(SEQ ID NO: 554)
GGACCATGTTTTGCCCATT;

(SEQ ID NO: 555)
ACCATGTTTTGCCCATTGA;

(SEQ ID NO: 556)
CATGTTTTGCCCATTGAAG;

(SEQ ID NO: 557)
TGTTTTGCCCATTGAAGCT;

(SEQ ID NO: 558)
TTTTGCCCATTGAAGCTTC;

(SEQ ID NO: 559)
TTGCCCATTGAAGCTTCTG;

(SEQ ID NO: 560)
GCCCATTGAAGCTTCTGGG; and (SEQ ID NO: 561)
CCATTGAAGCTTCTGGGTG;

FIG. 3 shows the nanoparticle size distribution of double stranded oligonucleotides including randomly selected androgen-receptor-specific oligonucleotides;

FIG. 4 shows the results of primary screening of 544 types of SAMiRNAs targeting the androgen receptor;

FIG. 5 shows the results of selection of SAMiRNAs including androgen-receptor-specific oligonucleotides for 14 sequences having the highest androgen receptor expression inhibitory effect among the screening results in FIG. 4;

FIG. 6 shows the results of secondary screening of SAMiRNAs including the androgen-receptor-specific oligonucleotides selected through the primary screening;

FIG. 7 shows the results of confirmation of the protein expression level of the androgen receptor after treatment of the SAMiRNA construct for the 14 selected sequences and the known sequences in the related literature;

FIG. 8 shows the results of confirmation of the inhibition of protein expression after treatment of the SAMiRNA construct for the two selected sequences among the results of FIG. 7 and the sequences of the related literature; and FIG. 9 shows the results of confirmation of the delivery effect of SAMiRNA nanoparticles into hair root cells using a confocal laser scanning microscope.

MODE FOR INVENTION

Unless otherwise defined, all technical and scientific terms used herein have the same meanings as those typically understood by those skilled in the art to which the present invention belongs. Generally, the nomenclature used herein and the test method described below are well known in the art and are typical.

In the present invention, in order to select an oligonucleotide capable of targeting an androgen receptor and inhibiting the expression thereof, a 2-base sliding-window algorithm was applied to the entire androgen receptor to thus determine a candidate sequence list. 468 candidate sequences having identity of 15 or fewer bases for RNA sequences with other genes were finally selected, and the extent of inhibition of the androgen receptor was tested using a total of 544 oligonucleotide sequences including 76 siRNA sequences disclosed in the known related literature (U.S. Patent Application Publication No. US 2007-0141009), and consequently, 14 types of oligonucleotides that were particularly effective were selected. Moreover, the oligonucleotide was capable of being manufactured into a double stranded oligonucleotide construct, thus increasing the intracellular delivery efficiency, thereby preventing hair loss and improving the hair growth effect.

Therefore, an aspect of the present invention pertains to an androgen-receptor-specific double stranded oligonucleotide including a sense strand including any one sequence selected from the group consisting of SEQ ID NOS: 6, 58, 68, 99, 107, 109, 260, 270, 284, 298, 348, 358, 359 and 434 and an antisense strand including a sequence complementary thereto.

The double stranded oligonucleotide according to the present invention is a concept including all materials having general RNAi (RNA interference) action, and the androgen-receptor-specific sequence also includes androgen-receptor-specific shRNA, ASO, etc., as will be obvious to those of ordinary skill in the art to which the present invention belongs. Conventional methods for delivering siRNA into target cells are still problematic in that siRNA is delivered into the cell through the cell membrane and is thus decreased in the activity thereof as it moves from the endosome in the cell to the cytoplasm, and is also easily degraded by lyases present in vivo. In addition, a DNA-RNA hybrid, in which DNA, which is an antisense oligo, and siRNA for degrading target mRNA are combined, is more stable than conventional double stranded oligo RNA in vivo, and the DNA portion thereof has an aptamer base sequence that is able to bind to the target protein, and thus it is efficiently delivered into target cells, and moreover, the DNA-RNA hybrid has an siRNA base sequence that inhibits the expression of RNA as a protein, so it binds to the target mRNA in the target cells and suppresses gene expression. Such DNA-RNA hybrid particles are composed only of biomaterials, are non-toxic, and are greatly resistant to DNase and RNase, which are nucleases present in the body, and thus may be regarded as new technology for RNAi.

In addition, so long as specificity to the androgen receptor is maintained, in the sense strand including any one sequence selected from the group consisting of SEQ ID NO: 1 to SEQ ID NO: 468 or the antisense strand complementary thereto, it will be obvious to those of ordinary skill in the art to which the present invention belongs that the androgenreceptor-specific siRNA including the sense strand including the sequence in which at least one base is substituted, deleted or inserted and the antisense strand is also incorporated in the scope of the present invention.

SEQ ID NOS: 1 to 468 are human androgen-receptor-specific sequences, and are RNA sense strand sequences having homology of 15 or fewer base sequences to other sites of the androgen receptor mRNA (Table 2). Also, SEQ ID NOS: 469 to 544 represent human androgen-receptor-specific siRNA sequences known from an existing patent (US 2007-0141009) (Table 3).

According to the present invention, as a result of comparing the intracellular activity with the androgen-receptor-specific oligonucleotide sequence disclosed in the existing patent, it was possible to discover an RNA sequence having superior efficiency and lower homology with other human mRNAs. The oligonucleotide according to the present invention is preferably an androgen-receptor-specific oligonucleotide including any one sequence selected from the group consisting of SEQ ID NOS: 6, 58, 68, 99, 107, 109, 260, 270, 284, 298, 348, 358, 359 and 434 as a sense strand, and more preferably an androgen-receptor-specific oligonucleotide comprising the sequence of SEQ ID NO: 68 or 109 as a sense strand.

The sense strand or antisense strand of the oligonucleotide according to the present invention is preferably composed of 19 to 31 nucleotides, and the sense strand comprising any one sequence selected from among SEQ ID NO: 1 to SEQ ID NO: 468 and the antisense strand complementary thereto are comprised.

Since the androgen-receptor-specific oligonucleotide according to the present invention has a base sequence designed to complementarily bind to mRNA encoding the corresponding gene, it is characterized in that it is capable of effectively suppressing the expression of the corresponding gene. In addition, it may include an overhang, which is a structure comprising one, two, or more unpaired nucleotides at the 3' end of the oligonucleotide.

In addition, in order to improve the stability of the oligonucleotide in vivo, various modifications may be included for conferring nuclease resistance and reducing non-specific immune responses. In the modification of the first or second oligonucleotide constituting the oligonucleotide, at least one modification selected from among a modification in which the —OH group at the 2' carbon position of the sugar structure in at least one nucleotide is substituted with $—CH_3$ (methyl), $—OCH_3$ (methoxy), $—NH_2$, —F (fluorine), —O-2-methoxyethyl-O-propyl, —O-2-methylthioethyl, —O-3-aminopropyl, —O-3-dimethylaminopropyl, —O—N-methylacetamido or —O-dimethylamidooxyethyl; a modification in which oxygen in the sugar structure in the nucleotide is substituted with sulfur; and a modification of nucleotide bonds to phosphorothioate, boranophosphate, or methyl phosphonate bonds may be used in combination, and modification into PNA (peptide nucleic acid), LNA (locked nucleic acid) or UNA (unlocked nucleic acid) may also be used (Ann. Rev. Med. 55, 61-65 2004; U.S. Pat. Nos. 5,660,985; 5,958,691; 6,531,584; 5,808,023; 6,326,358; 6,175,001; Bioorg. Med. Chem. Lett. 14:1139-1143, 2003; RNA, 9:1034-1048, 2003; Nucleic Acid Res. 31:589-595, 2003; Nucleic Acids Research, 38(17) 5761-5773, 2010; Nucleic Acids Research, 39(5) 1823-1832, 2011).

The androgen-receptor-specific oligonucleotide according to the present invention not only inhibits the expression of the corresponding gene, but also significantly inhibits the expression of the corresponding protein.

In an alternative embodiment, the present invention provides a conjugate in which a hydrophilic material and a hydrophobic material are conjugated to both ends of a double stranded oligonucleotide in order to improve in-vivo stability and efficient delivery of the androgen-receptor-specific double stranded oligonucleotide.

As described above, the double stranded oligonucleotide conjugate in which a hydrophilic material and a hydrophobic material are bound to a double stranded oligonucleotide may be formed into self-assembled nanoparticles through the hydrophobic interaction of the hydrophobic material (Korean Patent No. 1224828). Such nanoparticles have advantages of vastly superior delivery efficiency into the body and stability in the body as well as excellent particle size uniformity, so quality control is easy and the process of manufacturing a drug is simple.

Therefore, another aspect of the present invention pertains to a double stranded oligonucleotide construct having the structure of Structural Formula (1) below.

A-X—R—Y—B    Structural Formula (1)

In Structural Formula (1), A is a hydrophilic material, B is a hydrophobic material, each of X and Y independently represents a simple covalent bond or a linker-mediated covalent bond, and R represents an androgen-receptor-specific oligonucleotide comprising a sense strand including any one sequence selected from the group consisting of SEQ ID NOS: 6, 58, 68, 99, 107, 109, 260, 270, 284, 298, 348, 358, 359 and 434 and an antisense strand comprising a sequence complementary thereto.

More preferably, the double stranded oligonucleotide construct comprising the androgen-receptor-specific oligonucleotide according to the present invention has the structure of Structural Formula (2) below.

Structural Formula (2)

A—X—S—Y—B
AS

In Structural Formula (2), A, B, X and Y are as defined in Structural Formula (1), S represents the sense strand of the androgen-receptor-specific oligonucleotide, and AS represents the antisense strand of the androgen-receptor-specific oligonucleotide.

More preferably, the double stranded oligonucleotide construct comprising the androgen-receptor-specific oligonucleotide has the structure of Structural Formula (3) or (4) below.

Structural Formula (3)

A—X—5' S 3'—Y—B
AS

Structural Formula (4)

A—X—3' S 5'—Y—B
AS

In Structural Formula (3) and Structural Formula (4), A, B, S, AS, X and Y are as defined in Structural Formula (1), and 5' and 3' represent a 5' end and a 3' end of the sense strand of the androgen-receptor-specific oligonucleotide.

The double stranded oligonucleotide construct comprising the androgen-receptor-specific oligonucleotide in Structural Formula (1) to Structural Formula (4) may be configured such that one to three phosphate groups are bound to the 5' end of the antisense strand, and shRNA may be used in lieu of RNA, as will be obvious to those of ordinary skill in the art to which the present invention belongs.

The hydrophilic material in Structural Formula (1) to Structural Formula (4) is preferably a polymer material having a molecular weight of 200 to 10,000, and more preferably a polymer material having a molecular weight of 1,000 to 2,000. Examples of the hydrophilic polymer material preferably include, but are not necessarily limited to, nonionic hydrophilic polymer compounds, such as polyethylene glycol, polyvinylpyrrolidone, polyoxazoline, and the like.

In particular, the hydrophilic material A in Structural Formula (1) to Structural Formula (4) may be used in the form of a hydrophilic material block, as represented by Structural Formula (5) or Structural Formula (6) below. By using the appropriate number of such hydrophilic material blocks (n in Structural Formula (5) or Structural Formula (6)) depending on the need, problems due to polydispersity that may occur when using general synthetic polymer materials may be greatly mitigated.

$(A'_m\text{-}J)_n$ Structural Formula (5)

$(J\text{-}A'_m)_n$ Structural Formula (6)

In Structural Formula (5) or Structural Formula (6), A' is a hydrophilic material monomer, J is a linker for connecting m hydrophilic material monomers to each other or connecting m hydrophilic material monomers and siRNA to each other, m is an integer of 1 to 15, n is an integer of 1 to 10, and the repeating unit represented by $(A'_m\text{-}J)$ or $(J\text{-}A'_m)$ corresponds to the basic unit of the hydrophilic material block.

When using the hydrophilic material block as in Structural Formula (5) or Structural Formula (6), the double stranded oligonucleotide construct comprising the androgen-receptor-specific oligonucleotide according to the present invention may have the structure of Structural Formula (7) or Structural Formula (8) below.

$(A'_m\text{-}J)_n\text{-}X—R—Y—B$ Structural Formula (7)

$(J\text{-}A'_m)_n\text{-}X—R—Y—B$ Structural Formula (8)

In Structural Formula (7) and Structural Formula (8), X, R, Y and B are as defined in Structural Formula (1), and A', J, m and n are as defined in Structural Formula (5) and Structural Formula (6).

In Structural Formula (5) and Structural Formula (6), the hydrophilic material monomer A' may be used without limitation, so long as it meets the purpose of the present invention, among monomers of a nonionic hydrophilic polymer, and is preferably a monomer selected from among Compound (1) to Compound (3) shown in Table 1 below, and more preferably a monomer of Compound (1). In Compound (1), G is preferably selected from among $CH_2$, O, S, and NH.

In particular, among the hydrophilic material monomers, the monomer represented by Compound (1) is advantageous because various functional groups may be introduced thereto and also because it has good affinity in vivo and excellent biocompatibility, such as inducing a lower immune response, increases the in-vivo stability of the oligonucleotide contained in the construct according to Structural Formula (7) or Structural Formula (8), and increases the delivery efficiency thereof, so it is very suitable for the manufacture of the construct according to the present invention.

TABLE 1

| Structure of hydrophilic material monomer in the present invention | | |
|---|---|---|
| Compound (1) | Compound (2) | Compound (3) |
| 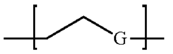<br>G is $CH_2$, O, S, or NH | 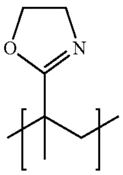 | 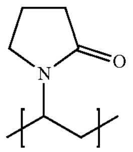 |

It is particularly preferable for the hydrophilic material in Structural Formula (5) to Structural Formula (8) to have a total molecular weight in the range of 1,000 to 2,000. Therefore, for example, when hexaethylene glycol according to Compound (1) in Structural Formula (7) and Structural Formula (8), that is, a material in which G is O and m is 6, is used, the molecular weight of the hexaethylene glycol spacer is 344, so the number of repetitions n is preferably 3 to 5. In particular, the present invention is characterized in that the repeating unit of the hydrophilic group, represented as $(A'_m\text{-}J)$ or $(J\text{-}A'_m)_n$ in Structural Formula (5) and Structural Formula (6), namely a hydrophilic material block, may be used in an appropriate number, represented by n, as necessary. The hydrophilic material monomer A and the linker J included in each of the hydrophilic material blocks may be independently the same or different in the hydrophilic material blocks. Specifically, when three hydrophilic material blocks are used (n=3), the first block may include the hydrophilic material monomer according to Compound (1), the second block may include the hydrophilic material monomer according to Compound (2), and the third block may include the hydrophilic material monomer according to Compound (3). In this way, different hydrophilic material monomers may be used for all hydrophilic material blocks, or any one hydrophilic material monomer selected from among the hydrophilic material monomers according to Compound (1) to Compound (3) may be identically used for all hydrophilic material blocks. Likewise, the linker that mediates the bonding of the hydrophilic material monomers may also use the same linker for each hydrophilic material block or a different linker for each hydrophilic material block. In addition, m, which is the number of hydrophilic material monomers, may be the same or different in the hydrophilic material blocks. Specifically, three hydrophilic material monomers (m=3) may be connected in the first hydrophilic material block, five hydrophilic material monomers (m=5) may be connected in the second hydrophilic material block, and four hydrophilic material monomers (m=4) may be connected in the third hydrophilic material block. In this way, different numbers of hydrophilic material monomers may be used, or the same number of hydrophilic material monomers may be used in all hydrophilic material blocks.

Moreover, in the present invention, the linker J is preferably selected from the group consisting of $PO_3^-$, $SO_3$, and $CO_2$, but is not limited thereto. Any linker may be used, so long as it meets the purpose of the present invention depending on the monomer of the hydrophilic material that is used, as will be obvious to those of ordinary skill in the art.

The hydrophobic material B in Structural Formula (1) to Structural Formula (4), Structural Formula (7), and Structural Formula (8) plays a role in forming nanoparticles composed of oligonucleotide constructs according to Structural Formula (1) to Structural Formula (4), Structural Formula (7), and Structural Formula (8) through hydrophobic interaction. The hydrophobic material preferably has a molecular weight of 250 to 1,000, and examples thereof may include, but are not limited to, a steroid derivative, a glyceride derivative, glycerol ether, polypropylene glycol, a $C_{12}$-$C_{50}$ unsaturated or saturated hydrocarbon, diacylphosphatidylcholine, fatty acid, phospholipid, lipopolyamine, and the like, and any hydrophobic material may be used so long as it meets the purpose of the present invention, as will be obvious to those of ordinary skill in the art to which the present invention belongs.

The steroid derivative may be selected from the group consisting of cholesterol, cholestanol, cholic acid, cholesteryl formate, cholestanyl formate, and cholesteryl amine, and the glyceride derivative may be selected from among mono-, di- and tri-glycerides. Here, fatty acid of the glyceride is preferably a $C_{12}$-$C_{50}$ unsaturated or saturated fatty acid.

In particular, among the hydrophobic materials, saturated or unsaturated hydrocarbon or cholesterol is preferred in that it has the advantage of being able to be easily bound in the synthesis step of the oligonucleotide construct according to the present invention, and a $C_{24}$ hydrocarbon, particularly a form containing a disulfide bond, is the most preferable.

The hydrophobic material is bound to the distal end of the hydrophilic material, and may be bound to any position on the sense strand or the antisense strand of the oligonucleotide.

The hydrophilic material or hydrophobic material and the androgen-receptor-specific oligonucleotide in Structural Formula (1) to Structural Formula (4), Structural Formula (7), and Structural Formula (8) according to the present invention are bound together via a simple covalent bond or a linker-mediated covalent bond (X or Y). The linker that mediates the covalent bond is covalently joined at the end of the hydrophilic material or the hydrophobic material and the androgen-receptor-specific oligonucleotide, and is not particularly limited, so long as it provides a cleavable bond in a specific environment as necessary. Therefore, the linker may be any compound that is joined to activate the androgen-receptor-specific oligonucleotide and/or the hydrophilic material (or hydrophobic material) during the process of manufacturing the double stranded oligonucleotide construct according to the present invention. The covalent bond may be either a non-cleavable bond or a cleavable bond. Here, the non-cleavable bond may be an amide bond or a phosphate bond, and the cleavable bond may be a disulfide bond, an acid-cleavable bond, an ester bond, an anhydride bond, a biodegradable bond, or an enzyme-cleavable bond, but the present invention is not limited thereto.

In addition, the androgen-receptor-specific oligonucleotide represented by R (or S and AS) in Structural Formula (1) to Structural Formula (4), Structural Formula (7), and Structural Formula (8) may be used without limitation, so long as it is a sequence that is able to specifically bind to mRNA of the androgen receptor. In the present invention, the androgen-receptor-specific oligonucleotide is preferably composed of a sense strand comprising any one sequence selected from the group consisting of SEQ ID NOS: 6, 58, 68, 99, 107, 109, 260, 270, 284, 298, 348, 358, 359, and 434 and an antisense strand comprising a sequence complementary thereto.

In particular, siRNA contained in Structural Formula (1) to Structural Formula (4), Structural Formula (7), and Structural Formula (8) according to the present invention is preferably an androgen-receptor-specific oligonucleotide composed of a sense strand comprising any one sequence selected from the group consisting of SEQ ID NOS: 6, 58, 68, 99, 107, 109, 260, 270, 284, 298, 348, 358, 359, and 434 and an antisense strand comprising a sequence complementary thereto.

In the double stranded oligonucleotide construct including the androgen-receptor-specific oligonucleotide according to the present invention, an amine group or a polyhistidine group may be additionally introduced at an end portion of the hydrophilic material opposite an end portion bound to the oligonucleotide.

This serves to facilitate the intracellular introduction of the carrier of the double stranded oligonucleotide construct including the androgen-receptor-specific oligonucleotide according to the present invention and the escape thereof from the endosome. In order to facilitate the intracellular introduction of the carrier, such as a quantum dot, dendrimer, liposome, etc., and escape thereof from the endosome, the use of an amine group and a polyhistidine group and the effect thereof have been reported.

Specifically, the primary amine group modified at the end or outside of the carrier forms a conjugate through electrostatic interaction with a negatively charged gene while protonating at the pH in vivo, and after intracellular introduction thereof, the carrier may be protected from the degradation of lysosomes because the escape from the endosome is facilitated due to the internal tertiary amine having a buffering effect at the low pH of the endosome (Gene transfer and expression inhibition using polymer-based hybrid materials. *Polymer Sci. Technol.*, Vol. 23, No. 3, pp 254-259). Moreover, histidine, a non-essential amino acid, has imidazoline (pKa3 6.04) at the residue (—R), thus effectively increasing the buffering capacity in endosomes and lysosomes, so it is known that the histidine modification may be used to increase the endosome escape efficiency in non-viral gene carriers including liposomes (Novel histidine-conjugated galactosylated cationic liposomes for efficient hepatocyte selective gene transfer in human hepatoma HepG2 cells. J. Controlled Release 118, pp 262-270).

The amine group or polyhistidine group may be connected to a hydrophilic material or to a hydrophilic material block via at least one linker.

When an amine group or a polyhistidine group is introduced into the hydrophilic material of the double stranded oligonucleotide construct according to Structural Formula (1) of the present invention, the structure of Structural Formula (9) may be represented.

$$P\text{-}J_1\text{-}J_2\text{-}A\text{—}X\text{—}R\text{—}Y\text{—}B \qquad \text{Structural Formula (9)}$$

In Structural Formula (9), A, B, R, X and Y are as defined in Structural Formula (1).

P represents an amine group or a polyhistidine group, $J_1$ and $J_2$ are linkers, $J_1$ and $J_2$ may be independently selected from among a simple covalent bond, $PO_3^-$, $SO_3$, $CO_2$, $C_{2-12}$ alkyl, alkenyl, and alkynyl, but are not limited thereto, and depending on the type of hydrophilic material that is used, any linker for $J_1$ and $J_2$ may be used, so long as it meets the purpose of the present invention, as will be obvious to those of ordinary skill in the art.

When an amine group is introduced, $J_2$ is preferably a simple covalent bond or $PO_3^-$, and $J_1$ is preferably $C_6$ alkyl, but the present invention is not limited thereto.

Also, when a polyhistidine group is introduced, in Structural Formula (9), $J_2$ is preferably a simple covalent bond or $PO_3^-$, and $J_1$ is preferably Compound (4) below, but the present invention is not limited thereto.

Compound (4)

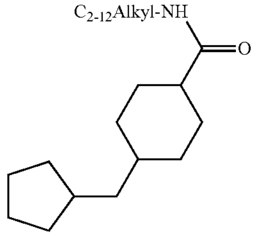

Moreover, when the hydrophilic material of the double stranded oligonucleotide construct according to Structural Formula (9) is a hydrophilic material block according to Structural Formula (5) or Structural Formula (6), and also when an amine group or a polyhistidine group is introduced thereto, the structure of Structural Formula (10) or Structural Formula (11) may be represented.

$P\text{-}J_1\text{-}J_2\text{-}(A'_m\text{-}J)_n\text{-}X—R—Y—B$ Structural Formula (10)

$P\text{-}J_1\text{-}J_2\text{-}(J\text{-}A'_m)_n\text{-}X—R—Y—B$ Structural Formula (11)

In Structural Formula (10) and Structural Formula (11), X, R, Y, B, A', J, m and n are as defined in Structural Formula (5) or Structural Formula (6), and P, $J_1$ and $J_2$ are as defined in Structural Formula (9).

In particular, in Structural Formula (10) and Structural Formula (11), the hydrophilic material is preferably provided in the form of being bound to the 3' end of the sense strand of the androgen-receptor-specific oligonucleotide. Here, Structural Formula (9) to Structural Formula (11) may have the form of Structural Formula (12) to Structural Formula (14) below.

Structural Formula (12)

$P—J_1—J_2—A—X\text{-}3'$ S $5'\text{-}Y—B$
AS

Structural Formula (13)

$P—J_1—J_2—(A'_m—J)_n—X\text{-}3'$ S $5'\text{-}Y—B$
AS

Structural Formula (14)

$P—J_1—J_2—(J—A'_m)_n—X\text{-}3'$ S $5'\text{-}Y—B$
AS

In Structural Formula (12) to Structural Formula (14), X, R, Y, B, A, A', J, m, n, P, $J_1$ and $J_2$ are as defined in Structural Formula (9) to Structural Formula (11), and 5' and 3' represent a 5' end and a 3' end of the sense strand of the androgen-receptor-specific oligonucleotide.

As the amine group that may be introduced in the present invention, primary to tertiary amine groups may be used, and the use of a primary amine group is particularly preferable. The amine group that is introduced may be provided as an amine salt, and, for example, the salt of the primary amine group may be provided in the form of $NH_3+$.

Also, the polyhistidine group that may be introduced in the present invention preferably comprises 3 to 10 histidines, particularly preferably 5 to 8 histidines, and most preferably 6 histidines. Additionally, at least one cysteine may be included, in addition to histidine.

Meanwhile, when the double stranded oligonucleotide construct comprising the androgen-receptor-specific oligonucleotide according to the present invention and the nanoparticle formed therefrom are provided with a targeting moiety, delivery thereof into the target cells is efficiently promoted, and thus it may be delivered even at a relatively low dose to target cells to exhibit a high target gene expression regulation function, and is able to prevent the delivery of non-specific androgen-receptor-specific oligonucleotides to other organs and cells.

Accordingly, the present invention provides a double stranded oligonucleotide construct configured such that a ligand L, particularly a ligand having a property of specifically binding to a receptor that promotes target cell internalization through receptor-mediated endocytosis (RME), is additionally bound to the construct according to Structural Formula (1) to Structural Formula (4), Structural Formula (7), and Structural Formula (8). For example, the form in which the ligand is bound to the double stranded oligonucleotide construct according to Structural Formula (1) has the structure of Structural Formula (15) below.

$(L_i\text{-}Z)\text{-}A\text{-}X—R—Y—B$ Structural Formula (15)

In Structural Formula (15), A, B, X and Y are as defined in Structural Formula (1), L is a ligand having a property of specifically binding to a receptor that promotes target cell internalization through receptor-mediated endocytosis (RME), and i is an integer of 1 to 5, preferably an integer of 1 to 3.

The ligand in Structural Formula (15) is preferably selected from among target-receptor-specific antibodies, aptamers, and peptides having RME properties capable of promoting cell internalization in a target-cell-specific manner, and chemical materials, including folate (the terms folate and folic acid generally being used interchangeably with each other, with “folate” as used herein meaning folate in a natural state or an activated state in the human body), hexoamine such as N-acetylgalactosamine (NAG), a sugar or carbohydrate such as glucose or mannose, and the like, but is not limited thereto.

In addition, the hydrophilic material A in Structural Formula (15) may be used in the form of a hydrophilic material block according to Structural Formula (5) and Structural Formula (6).

Still another aspect of the present invention pertains to a nanoparticle comprising the double stranded oligonucleotide construct comprising the androgen-receptor-specific oligonucleotide.

As described above, the double stranded oligonucleotide construct comprising the androgen-receptor-specific oligonucleotide is amphiphilic because both hydrophobic and hydrophilic materials are contained therein, and the hydrophilic portion has affinity through interactions such as hydrogen bonds, etc. with water molecules present in the body and is thus directed outwards, and hydrophobic materials are directed inwards through hydrophobic interactions therebetween, thus forming a thermodynamically stable nanoparticle. Specifically, the hydrophobic material is located in the center of the nanoparticle, and the hydrophilic material is located in the outer direction of the androgen-receptor-specific oligonucleotide, resulting in a nanoparticle having a form that protects the androgen-receptor-specific oligonucleotide. The nanoparticle thus formed improves the intracellular delivery of the androgen-receptor-specific oligonucleotide and increases oligonucleotide efficacy.

The nanoparticle according to the present invention may be formed only with the double stranded oligonucleotide construct comprising the oligonucleotide having the same sequence, or may also be composed of a double stranded oligonucleotide construct comprising an oligonucleotide having a different sequence. In the present invention, the oligonucleotide having the different sequence may be an oligonucleotide specific to an androgen receptor as a different target gene, and the case of different sequences while having the same target gene specificity may be incorporated.

Also, a double stranded oligonucleotide construct comprising siRNA specific to other hair-loss-related genes, in addition to the androgen-receptor-specific oligonucleotide, may be included in the scope of nanoparticles according to the present invention.

Yet another aspect of the present invention pertains to a pharmaceutical composition for preventing hair loss, particularly androgenetic alopecia, or promoting hair growth, containing, as an active ingredient, an androgen-receptor-specific double stranded oligonucleotide, a double stranded oligonucleotide construct including the same, and/or a nanoparticle including the double stranded oligonucleotide construct.

The pharmaceutical composition may be used for a formulation selected from among ointment, paste, gel, jelly, serum, aerosol spray, non-aerosol spray, foam, cream, lotion, solution, and suspension formulations, but is not limited thereto.

The composition according to the present invention exhibits an effect of preventing hair loss or inducing hair growth by inhibiting the binding of DHT, which is a metabolite of testosterone, to an androgen receptor.

In addition to the double stranded oligonucleotide according to the present invention or the construct thereof, a double stranded oligonucleotide specific to a hair-loss-disease-related gene other than the androgen receptor or a double stranded oligonucleotide construct comprising the same may be further included in the composition according to the present invention.

The composition according to the present invention may be applied to hair loss associated with a gene involved in the upstream or downstream signaling of the androgen receptor, particularly androgenetic alopecia, but is not limited thereto.

The composition of the present invention may be manufactured so as to further include at least one pharmaceutically acceptable carrier in addition to the above active ingredient. The pharmaceutically acceptable carrier has to be compatible with the active ingredient of the present invention, and may include saline, sterile water, Ringer's solution, buffered saline, dextrose solution, maltodextrin solution, glycerol, and ethanol, which may be used alone or in combinations of two or more thereof. Also, other typical additives, such as antioxidants, buffers, bacteriostatic agents, and the like, may be added as necessary. Also, diluents, dispersants, surfactants, binders, and lubricants may be further added to manufacture injectable formulations such as aqueous solutions, suspensions, emulsions, and the like. In particular, it is preferable to provide a formulation in a lyophilized form. In order to manufacture a lyophilized formulation, a method commonly known in the art to which the present invention belongs may be used, and a stabilizer for lyophilization may be added. Furthermore, a formulation is preferably manufactured depending on each disease or component using an appropriate method in the art or using a method disclosed in Remington's Pharmaceutical Science (Mack Publishing Company, Easton PA).

The amount and administration method of the active ingredient, etc. contained in the composition of the present invention may be determined by an expert of ordinary skill in the art based on the symptoms and severity of hair loss of an individual. Moreover, the composition of the present invention may be formulated in various forms, such as powders, tablets, injections, ointments, and the like, and may be provided in unit-dose or multi-dose containers, such as sealed ampoules and bottles.

Still yet another aspect of the present invention provides a cosmetic composition for preventing hair loss, particularly androgenetic alopecia, or promoting hair growth, containing, as an active ingredient, an androgen-receptor-specific double stranded oligonucleotide, a double stranded oligonucleotide construct comprising the same, and/or a nanoparticle including the double stranded oligonucleotide construct.

The composition may be used for a formulation selected from among hair tonic, hair conditioner, hair essence, hair lotion, hair nutrition lotion, hair shampoo, hair rinse, hair treatment, hair cream, hair nutrition cream, hair moisture cream, hair massage cream, hair wax, hair aerosol, hair pack, hair nutrition pack, hair soap, hair cleansing foam, hair oil, hair drying agent, hair preservative, hair dye, hair wave agent, hair decolorant, hair gel, hair glaze, hair dressing, hair lacquer, hair moisturizer, hair mousse, and hair spray formulations, but is not limited thereto.

A further aspect of the present invention provides a method of treating hair loss comprising administering the construct, nanoparticle, or pharmaceutical composition according to the present invention to a subject in need of hair growth, or applying the construct, nanoparticle, or pharmaceutical composition according to the present invention onto an area in need of hair growth.

In addition, the present invention pertains to a method of preventing hair loss or promoting hair growth comprising administering or applying the construct, nanoparticle, or cosmetic composition according to the present invention to a subject in need of hair-loss prevention or hair growth or onto the corresponding area.

In addition, the present invention pertains to the use of the double stranded oligonucleotide construct to prevent hair loss or to promote hair growth.

In addition, the present invention pertains to the use of the double stranded oligonucleotide construct to manufacture a medicine or a cosmetic for preventing hair loss or promoting hair growth.

Hair loss in the present invention includes androgenetic alopecia, alopecia areata, and telogen effluvium.

A better understanding of the present invention may be obtained through the following examples. These examples are merely set forth to illustrate the present invention, and are not to be construed as limiting the scope of the present invention, as will be apparent to those of ordinary skill in the art.

Example 1. Algorithm and Candidate Sequence Selection for Oligonucleotide Screening Targeting Androgen Receptor An siRNA-based high-throughput drug-screening method is capable of generating all possible candidate sequences by applying a 1-base or 2-base sliding-window algorithm to total mRNA and also of removing unnecessary candidate sequences through homology filtering, thus confirming the extent of inhibition of gene expression for all of the finally selected oligonucleotides.

First, the design process for the oligonucleotide candidate sequence for the androgen receptor was performed in a manner in which the isoform common region was extracted based on the exon map of the human androgen receptor mRNA NM_000044.3 (isoform 1, 10,661 bp) and NM_001011645.2 (isoform 2, 8112 bp), and a 2-base sliding-window algorithm was applied to the extracted isoform common region, thereby selecting 3,956 candidate sequences composed of 19 bases.

In the selected oligonucleotide candidate sequence list, 468 candidate sequences having identity of 15 or fewer bases for RNA sequences with other genes were finally selected when the BLAST e-value for human total reference sequence RNA was 100 or less. Here, an experiment on the extent of inhibition of the expression of the androgen receptor was performed using a total of 544 oligonucleotide sequences including 76 siRNA sequences mentioned in previously known related literature (U.S. Patent Application Publication No. US 2007-0141009).

TABLE 2

Androgen-receptor-specific oligonucleotide candidate sequence selected through 2-base sliding-window screening

| SEQ ID NO: | Accession No. | Position | Sense strand sequence |
|---|---|---|---|
| 1 | NM_000044.3 | 2739-2757 | ACTGCCAGGGACCATGTTT |
| 2 | NM_000044.3 | 2741-2759 | TGCCAGGGACCATGTTTTG |
| 3 | NM_000044.3 | 2743-2761 | CCAGGGACCATGTTTTGCC |
| 4 | NM_000044.3 | 2745-2763 | AGGGACCATGTTTTGCCCA |
| 5 | NM_000044.3 | 2755-2773 | TTTTGCCCATTGACTATTA |
| 6 | NM_000044.3 | 2757-2775 | TTGCCCATTGACTATTACT |
| 7 | NM_000044.3 | 2763-2781 | ATTGACTATTACTTTCCAC |
| 8 | NM_000044.3 | 2765-2783 | TGACTATTACTTTCCACCC |
| 9 | NM_000044.3 | 2767-2785 | ACTATTACTTTCCACCCCA |
| 10 | NM_000044.3 | 2769-2787 | TATTACTTTCCACCCCAGA |
| 11 | NM_000044.3 | 2785-2803 | AGAAGACCTGCCTGATCTG |
| 12 | NM_000044.3 | 2861-2879 | CTTCTTCAAAAGAGCCGCT |
| 13 | NM_000044.3 | 2921-2939 | CACTATTGATAAATTCCGA |
| 14 | NM_000044.3 | 2923-2941 | CTATTGATAAATTCCGAAG |
| 15 | NM_000044.3 | 2947-2965 | ATTGTCCATCTTGTCGTCT |
| 16 | NM_000044.3 | 2959-2977 | GTCGTCTTCGGAAATGTTA |
| 17 | NM_000044.3 | 2965-2983 | TTCGGAAATGTTATGAAGC |
| 18 | NM_000044.3 | 2971-2989 | AATGTTATGAAGCAGGGAT |
| 19 | NM_000044.3 | 3093-3111 | CTGACAGTGTCACACATTG |
| 20 | NM_000044.3 | 3111-3129 | GAAGGCTATGAATGTCAGC |
| 21 | NM_000044.3 | 3169-3187 | TAGTGTGTGCTGGACACGA |
| 22 | NM_000044.3 | 3171-3189 | GTGTGTGCTGGACACGACA |
| 23 | NM_000044.3 | 3189-3207 | AACAACCAGCCCGACTCCT |
| 24 | NM_000044.3 | 3197-3215 | GCCCGACTCCTTTGCAGCC |
| 25 | NM_000044.3 | 3217-3235 | TGCTCTCTAGCCTCAATGA |
| 26 | NM_000044.3 | 3243-3261 | GAGAGACAGCTTGTACACG |
| 27 | NM_000044.3 | 3251-3269 | GCTTGTACACGTGGTCAAG |
| 28 | NM_000044.3 | 3253-3271 | TTGTACACGTGGTCAAGTG |

TABLE 2-continued

Androgen-receptor-specific oligonucleotide candidate sequence selected through 2-base sliding-window screening

| SEQ ID NO: | Accession No. | Position | Sense strand sequence |
|---|---|---|---|
| 29 | NM_000044.3 | 3255-3273 | GTACACGTGGTCAAGTGGG |
| 30 | NM_000044.3 | 3257-3275 | ACACGTGGTCAAGTGGGCC |
| 31 | NM_000044.3 | 3259-3277 | ACGTGGTCAAGTGGGCCAA |
| 32 | NM_000044.3 | 3263-3281 | GGTCAAGTGGGCCAAGGCC |
| 33 | NM_000044.3 | 3285-3303 | CCTGGCTTCCGCAACTTAC |
| 34 | NM_000044.3 | 3287-3305 | TGGCTTCCGCAACTTACAC |
| 35 | NM_000044.3 | 3289-3307 | GCTTCCGCAACTTACACGT |
| 36 | NM_000044.3 | 3291-3309 | TTCCGCAACTTACACGTGG |
| 37 | NM_000044.3 | 3293-3311 | CCGCAACTTACACGTGGAC |
| 38 | NM_000044.3 | 3295-3313 | GCAACTTACACGTGGACGA |
| 39 | NM_000044.3 | 3303-3321 | CACGTGGACGACCAGATGG |
| 40 | NM_000044.3 | 3309-3327 | GACGACCAGATGGCTGTCA |
| 41 | NM_000044.3 | 3325-3343 | TCATTCAGTACTCCTGGAT |
| 42 | NM_000044.3 | 3347-3365 | GCTCATGGTGTTTGCCATG |
| 43 | NM_000044.3 | 3361-3379 | CCATGGGCTGGCGATCCTT |
| 44 | NM_000044.3 | 3369-3387 | TGGCGATCCTTCACCAATG |
| 45 | NM_000044.3 | 3385-3403 | ATGTCAACTCCAGGATGCT |
| 46 | NM_000044.3 | 3391-3409 | ACTCCAGGATGCTCTACTT |
| 47 | NM_000044.3 | 3395-3413 | CAGGATGCTCTACTTCGCC |
| 48 | NM_000044.3 | 3397-3415 | GGATGCTCTACTTCGCCCC |
| 49 | NM_000044.3 | 3399-3417 | ATGCTCTACTTCGCCCCTG |
| 50 | NM_000044.3 | 3401-3419 | GCTCTACTTCGCCCCTGAT |
| 51 | NM_000044.3 | 3403-3421 | TCTACTTCGCCCCTGATCT |
| 52 | NM_000044.3 | 3405-3423 | TACTTCGCCCCTGATCTGG |
| 53 | NM_000044.3 | 3407-3425 | CTTCGCCCCTGATCTGGTT |
| 54 | NM_000044.3 | 3409-3427 | TCGCCCCTGATCTGGTTTT |
| 55 | NM_000044.3 | 3411-3429 | GCCCCTGATCTGGTTTTCA |
| 56 | NM_000044.3 | 3413-3431 | CCCTGATCTGGTTTTCAAT |
| 57 | NM_000044.3 | 3427-3445 | TCAATGAGTACCGCATGCA |
| 58 | NM_000044.3 | 3429-3447 | AATGAGTACCGCATGCACA |
| 59 | NM_000044.3 | 3435-3453 | TACCGCATGCACAAGTCCC |
| 60 | NM_000044.3 | 3437-3455 | CCGCATGCACAAGTCCCGG |
| 61 | NM_000044.3 | 3439-3457 | GCATGCACAAGTCCCGGAT |
| 62 | NM_000044.3 | 3451-3469 | CCCGGATGTACAGCCAGTG |
| 63 | NM_000044.3 | 3461-3479 | CAGCCAGTGTGTCCGAATG |
| 64 | NM_000044.3 | 3463-3481 | GCCAGTGTGTCCGAATGAG |

TABLE 2-continued

Androgen-receptor-specific oligonucleotide candidate sequence selected through 2-base sliding-window screening

| SEQ ID NO: | Accession No. | Position | Sense strand sequence |
|---|---|---|---|
| 65 | NM_000044.3 | 3465-3483 | CAGTGTGTCCGAATGAGGC |
| 66 | NM_000044.3 | 3469-3487 | GTGTCCGAATGAGGCACCT |
| 67 | NM_000044.3 | 3479-3497 | GAGGCACCTCTCTCAAGAG |
| 68 | NM_000044.3 | 3495-3513 | GAGTTTGGATGGCTCCAAA |
| 69 | NM_000044.3 | 3507-3525 | CTCCAAATCACCCCCCAGG |
| 70 | NM_000044.3 | 3509-3527 | CCAAATCACCCCCCAGGAA |
| 71 | NM_000044.3 | 3527-3545 | ATTCCTGTGCATGAAAGCA |
| 72 | NM_000044.3 | 3567-3585 | CCAGTGGATGGGCTGAAAA |
| 73 | NM_000044.3 | 3569-3587 | AGTGGATGGGCTGAAAAAT |
| 74 | NM_000044.3 | 3601-3619 | ATGAACTTCGAATGAACTA |
| 75 | NM_000044.3 | 3603-3621 | GAACTTCGAATGAACTACA |
| 76 | NM_000044.3 | 3605-3623 | ACTTCGAATGAACTACATC |
| 77 | NM_000044.3 | 3607-3625 | TTCGAATGAACTACATCAA |
| 78 | NM_000044.3 | 3609-3627 | CGAATGAACTACATCAAGG |
| 79 | NM_000044.3 | 3621-3639 | ATCAAGGAACTCGATCGTA |
| 80 | NM_000044.3 | 3623-3641 | CAAGGAACTCGATCGTATC |
| 81 | NM_000044.3 | 3625-3643 | AGGAACTCGATCGTATCAT |
| 82 | NM_000044.3 | 3627-3645 | GAACTCGATCGTATCATTG |
| 83 | NM_000044.3 | 3629-3647 | ACTCGATCGTATCATTGCA |
| 84 | NM_000044.3 | 3631-3649 | TCGATCGTATCATTGCATG |
| 85 | NM_000044.3 | 3633-3651 | GATCGTATCATTGCATGCA |
| 86 | NM_000044.3 | 3669-3687 | TCCTGCTCAAGACGCTTCT |
| 87 | NM_000044.3 | 3671-3689 | CTGCTCAAGACGCTTCTAC |
| 88 | NM_000044.3 | 3709-3727 | ACTCCGTGCAGCCTATTGC |
| 89 | NM_000044.3 | 3711-3729 | TCCGTGCAGCCTATTGCGA |
| 90 | NM_000044.3 | 3713-3731 | CGTGCAGCCTATTGCGAGA |
| 91 | NM_000044.3 | 3715-3733 | TGCAGCCTATTGCGAGAGA |
| 92 | NM_000044.3 | 3717-3735 | CAGCCTATTGCGAGAGAGC |
| 93 | NM_000044.3 | 3719-3737 | GCCTATTGCGAGAGAGCTG |
| 94 | NM_000044.3 | 3749-3767 | TTTTGACCTGCTAATCAAG |
| 95 | NM_000044.3 | 3759-3777 | CTAATCAAGTCACACATGG |
| 96 | NM_000044.3 | 3765-3783 | AAGTCACACATGGTGAGCG |
| 97 | NM_000044.3 | 3781-3799 | GCGTGGACTTTCCGGAAAT |
| 98 | NM_000044.3 | 3789-3807 | TTTCCGGAAATGATGGCAG |
| 99 | NM_000044.3 | 3845-3863 | GAAAGTCAAGCCCATCTAT |
| 100 | NM_000044.3 | 3847-3865 | AAGTCAAGCCCATCTATTT |

TABLE 2-continued

Androgen-receptor-specific oligonucleotide candidate sequence selected through 2-base sliding-window screening

| SEQ ID NO: | Accession No. | Position | Sense strand sequence |
|---|---|---|---|
| 101 | NM_000044.3 | 3937-3955 | CTGTTATAACTCTGCACTA |
| 102 | NM_000044.3 | 3939-3957 | GTTATAACTCTGCACTACT |
| 103 | NM_000044.3 | 3941-3959 | TATAACTCTGCACTACTCC |
| 104 | NM_000044.3 | 3947-3965 | TCTGCACTACTCCTCTGCA |
| 105 | NM_000044.3 | 3971-3989 | TTGGGGAATTTCCTCTATT |
| 106 | NM_000044.3 | 3973-3991 | GGGGAATTTCCTCTATTGA |
| 107 | NM_000044.3 | 3987-4005 | ATTGATGTACAGTCTGTCA |
| 108 | NM_000044.3 | 3989-4007 | TGATGTACAGTCTGTCATG |
| 109 | NM_000044.3 | 3991-4009 | ATGTACAGTCTGTCATGAA |
| 110 | NM_000044.3 | 3993-4011 | GTACAGTCTGTCATGAACA |
| 111 | NM_000044.3 | 4021-4039 | ATTCTATTTGCTGGGCTTT |
| 112 | NM_000044.3 | 4071-4089 | TTCCCTCCCTATCTAACCC |
| 113 | NM_000044.3 | 4073-4091 | CCCTCCCTATCTAACCCTC |
| 114 | NM_000044.3 | 4075-4093 | CTCCCTATCTAACCCTCCC |
| 115 | NM_000044.3 | 4077-4095 | CCCTATCTAACCCTCCCAT |
| 116 | NM_000044.3 | 4079-4097 | CTATCTAACCCTCCCATGG |
| 117 | NM_000044.3 | 4089-4107 | CTCCCATGGCACCTTCAGA |
| 118 | NM_000044.3 | 4091-4109 | CCCATGGCACCTTCAGACT |
| 119 | NM_000044.3 | 4117-4135 | CCATTGTGGCTCCTATCTG |
| 120 | NM_000044.3 | 4119-4137 | ATTGTGGCTCCTATCTGTG |
| 121 | NM_000044.3 | 4125-4143 | GCTCCTATCTGTGTTTTGA |
| 122 | NM_000044.3 | 4179-4197 | CATATGGCCCAGTGTCAAG |
| 123 | NM_000044.3 | 4181-4199 | TATGGCCCAGTGTCAAGTT |
| 124 | NM_000044.3 | 4205-4223 | TGTTTACAGCACTACTCTG |
| 125 | NM_000044.3 | 4229-4247 | GCCACACAAACGTTTACTT |
| 126 | NM_000044.3 | 4243-4261 | TACTTATCTTATGCCACGG |
| 127 | NM_000044.3 | 4245-4263 | CTTATCTTATGCCACGGGA |
| 128 | NM_000044.3 | 4253-4271 | ATGCCACGGGAAGTTTAGA |
| 129 | NM_000044.3 | 4263-4281 | AAGTTTAGAGAGCTAAGAT |
| 130 | NM_000044.3 | 4265-4283 | GTTTAGAGAGCTAAGATTA |
| 131 | NM_000044.3 | 4267-4285 | TTAGAGAGCTAAGATTATC |
| 132 | NM_000044.3 | 4269-4287 | AGAGAGCTAAGATTATCTG |
| 133 | NM_000044.3 | 4451-4469 | GAGGCCAATAGTGACGAGA |
| 134 | NM_000044.3 | 4461-4479 | GTGACGAGAAGGTGAAAAT |
| 135 | NM_000044.3 | 4463-4481 | GACGAGAAGGTGAAAATTG |
| 136 | NM_000044.3 | 4487-4505 | CCATGGGGAGTTACTGATT |

TABLE 2-continued

Androgen-receptor-specific oligonucleotide candidate sequence selected through 2-base sliding-window screening

| SEQ ID NO: | Accession No. | Position | Sense strand sequence |
|---|---|---|---|
| 137 | NM_000044.3 | 4521-4539 | TCCACGGGAGACTTTATTT |
| 138 | NM_000044.3 | 4523-4541 | CACGGGAGACTTTATTTTC |
| 139 | NM_000044.3 | 4549-4567 | GGCTATTGCCATTAGAGGG |
| 140 | NM_000044.3 | 4551-4569 | CTATTGCCATTAGAGGGCA |
| 141 | NM_000044.3 | 4621-4639 | AAGGAGGGCAATGGAGCAT |
| 142 | NM_000044.3 | 4623-4641 | GGAGGGCAATGGAGCATCA |
| 143 | NM_000044.3 | 4625-4643 | AGGGCAATGGAGCATCAGT |
| 144 | NM_000044.3 | 4627-4645 | GGCAATGGAGCATCAGTAC |
| 145 | NM_000044.3 | 4641-4659 | AGTACCTGCCCACAGCCTT |
| 146 | NM_000044.3 | 4661-4679 | GTCCCTGGGGGCTAGACTG |
| 147 | NM_000044.3 | 4667-4685 | GGGGGCTAGACTGCTCAAC |
| 148 | NM_000044.3 | 4691-4709 | AGCAATTCATTATACTGAA |
| 149 | NM_000044.3 | 4713-4731 | GTGCTTGTTGTTGAAAATT |
| 150 | NM_000044.3 | 4735-4753 | CTGCATGTTAATGCCTCAC |
| 151 | NM_000044.3 | 4783-4801 | CCTCCAACTTCAGATTGAC |
| 152 | NM_000044.3 | 4785-4803 | TCCAACTTCAGATTGACTT |
| 153 | NM_000044.3 | 4817-4835 | TAAGACCTTTGAACTGAAT |
| 154 | NM_000044.3 | 4819-4837 | AGACCTTTGAACTGAATGT |
| 155 | NM_000044.3 | 4853-4871 | CTTGGCGACTTCCACAGAA |
| 156 | NM_000044.3 | 4855-4873 | TGGCGACTTCCACAGAAAA |
| 157 | NM_000044.3 | 4877-4895 | TGACCACTGAGAAGAAGGA |
| 158 | NM_000044.3 | 4935-4953 | CAGGTCTGCTTTCTCATGT |
| 159 | NM_000044.3 | 4947-4965 | CTCATGTGTGAGTCAGGGA |
| 160 | NM_000044.3 | 5019-5037 | GACACTGACTGAATAGTTA |
| 161 | NM_000044.3 | 5037-5055 | AAACTCTCACTGCCACTAC |
| 162 | NM_000044.3 | 5041-5059 | TCTCACTGCCACTACCTTT |
| 163 | NM_000044.3 | 5099-5117 | ACTCCGTGAAGCCACAAGC |
| 164 | NM_000044.3 | 5105-5123 | TGAAGCCACAAGCACCTTA |
| 165 | NM_000044.3 | 5111-5129 | CACAAGCACCTTATGTCCT |
| 166 | NM_000044.3 | 5199-5217 | TTCTTTTGGGCATGTTCAC |
| 167 | NM_000044.3 | 5201-5219 | CTTTTGGGCATGTTCACAG |
| 168 | NM_000044.3 | 5241-5259 | CCACCAAGAAGGTTAGCAG |
| 169 | NM_000044.3 | 5249-5267 | AAGGTTAGCAGGCCAACAG |
| 170 | NM_000044.3 | 5251-5269 | GGTTAGCAGGCCAACAGCT |
| 171 | NM_000044.3 | 5269-5287 | TCTGACATCTATCTGTAGA |
| 172 | NM_000044.3 | 5273-5291 | ACATCTATCTGTAGATGCC |

TABLE 2-continued

Androgen-receptor-specific oligonucleotide candidate sequence selected through 2-base sliding-window screening

| SEQ ID NO: | Accession No. | Position | Sense strand sequence |
|---|---|---|---|
| 173 | NM_000044.3 | 5275-5293 | ATCTATCTGTAGATGCCAG |
| 174 | NM_000044.3 | 5311-5329 | TACCAACTCTCAGATCGCT |
| 175 | NM_000044.3 | 5313-5331 | CCAACTCTCAGATCGCTGG |
| 176 | NM_000044.3 | 5323-5341 | GATCGCTGGAGCCCTTAGA |
| 177 | NM_000044.3 | 5335-5353 | CCTTAGACAAACTGGAAAG |
| 178 | NM_000044.3 | 5401-5419 | CAGAGATGATACCCTCCCA |
| 179 | NM_000044.3 | 5407-5425 | TGATACCCTCCCAGCAAGT |
| 180 | NM_000044.3 | 5459-5477 | AAAGGGGCTACCCAGATCA |
| 181 | NM_000044.3 | 5465-5483 | GCTACCCAGATCAGGGTTG |
| 182 | NM_000044.3 | 5493-5511 | CTCAATTACCAGGGTGGGA |
| 183 | NM_000044.3 | 5553-5571 | CTTGTCACCCAGCATATCC |
| 184 | NM_000044.3 | 5647-5665 | AGCCTAAAGCCAGATGGAC |
| 185 | NM_000044.3 | 5715-5733 | TCTGACATTGCCCATACTC |
| 186 | NM_000044.3 | 5771-5789 | GAGGGAGGCCAAACCATTG |
| 187 | NM_000044.3 | 5773-5791 | GGGAGGCCAAACCATTGAG |
| 188 | NM_000044.3 | 5775-5793 | GAGGCCAAACCATTGAGAC |
| 189 | NM_000044.3 | 5795-5813 | TTCTACAGAACCATGGCTT |
| 190 | NM_000044.3 | 5803-5821 | AACCATGGCTTCTTTCGGA |
| 191 | NM_000044.3 | 5811-5829 | CTTCTTTCGGAAAGGTCTG |
| 192 | NM_000044.3 | 5815-5833 | TTTCGGAAAGGTCTGGTTG |
| 193 | NM_000044.3 | 5841-5859 | TCCAATACTTTGCCACCCA |
| 194 | NM_000044.3 | 5859-5877 | ATGAACTCAGGGTGTGCCC |
| 195 | NM_000044.3 | 5867-5885 | AGGGTGTGCCCTGGGACAC |
| 196 | NM_000044.3 | 5883-5901 | CACTGGTTTTATATAGTCT |
| 197 | NM_000044.3 | 5895-5913 | ATAGTCTTTTGGCACACCT |
| 198 | NM_000044.3 | 5897-5915 | AGTCTTTTGGCACACCTGT |
| 199 | NM_000044.3 | 5915-5933 | TGTTCTGTTGACTTCGTTC |
| 200 | NM_000044.3 | 5963-5981 | ACCTACTTTCTCATCTTGG |
| 201 | NM_000044.3 | 5991-6009 | CCTTACTTAGCTCTTAATC |
| 202 | NM_000044.3 | 5999-6017 | AGCTCTTAATCTCATCTGT |
| 203 | NM_000044.3 | 6005-6023 | TAATCTCATCTGTTGAACT |
| 204 | NM_000044.3 | 6007-6025 | ATCTCATCTGTTGAACTCA |
| 205 | NM_000044.3 | 6045-6063 | TCAAGCTGCCCATTTTAAT |
| 206 | NM_000044.3 | 6077-6095 | TTGTTGAGAGGATAGTTTC |
| 207 | NM_000044.3 | 6099-6117 | GTGACATGATATGATCCAC |
| 208 | NM_000044.3 | 6145-6163 | TGATATTAATAGCCAAACG |

TABLE 2-continued

Androgen-receptor-specific oligonucleotide candidate sequence selected through 2-base sliding-window screening

| SEQ ID NO: | Accession No. | Position | Sense strand sequence |
|---|---|---|---|
| 209 | NM_000044.3 | 6147-6165 | ATATTAATAGCCAAACGAA |
| 210 | NM_000044.3 | 6149-6167 | ATTAATAGCCAAACGAACT |
| 211 | NM_000044.3 | 6151-6169 | TAATAGCCAAACGAACTTC |
| 212 | NM_000044.3 | 6153-6171 | ATAGCCAAACGAACTTCAA |
| 213 | NM_000044.3 | 6155-6173 | AGCCAAACGAACTTCAAAA |
| 214 | NM_000044.3 | 6157-6175 | CCAAACGAACTTCAAAACA |
| 215 | NM_000044.3 | 6159-6177 | AAACGAACTTCAAAACAGC |
| 216 | NM_000044.3 | 6193-6211 | AGAGGGGAACCTAAGATGA |
| 217 | NM_000044.3 | 6195-6213 | AGGGGAACCTAAGATGAGT |
| 218 | NM_000044.3 | 6197-6215 | GGGAACCTAAGATGAGTAA |
| 219 | NM_000044.3 | 6199-6217 | GAACCTAAGATGAGTAATA |
| 220 | NM_000044.3 | 6211-6229 | AGTAATATGCCAATCCAAG |
| 221 | NM_000044.3 | 6213-6231 | TAATATGCCAATCCAAGAC |
| 222 | NM_000044.3 | 6215-6233 | ATATGCCAATCCAAGACTG |
| 223 | NM_000044.3 | 6243-6261 | ACTAAAGCTGACAGGTTCC |
| 224 | NM_000044.3 | 6265-6283 | TTTGGGGTGGGATAGACAT |
| 225 | NM_000044.3 | 6299-6317 | ATTATTACACAATCTGGCT |
| 226 | NM_000044.3 | 6301-6319 | TATTACACAATCTGGCTCA |
| 227 | NM_000044.3 | 6317-6335 | TCATGTACAGGATCACTTT |
| 228 | NM_000044.3 | 6377-6395 | GTTACACTAGGTTACATTT |
| 229 | NM_000044.3 | 6395-6413 | TTAATAGGTCCTTTACATC |
| 230 | NM_000044.3 | 6439-6457 | GTGATACACAGATTGAATT |
| 231 | NM_000044.3 | 6469-6487 | ATATCTCTCCTTGTAAATA |
| 232 | NM_000044.3 | 6485-6503 | ATACTAGAAGCTCTCCTTT |
| 233 | NM_000044.3 | 6487-6505 | ACTAGAAGCTCTCCTTTAC |
| 234 | NM_000044.3 | 6533-6551 | TGGGTTTCCCAATTGTGAC |
| 235 | NM_000044.3 | 6607-6625 | AGCAGTGTAATTAAAAGCA |
| 236 | NM_000044.3 | 6623-6641 | GCAACAACTGGATTACTCC |
| 237 | NM_000044.3 | 6625-6643 | AACAACTGGATTACTCCAA |
| 238 | NM_000044.3 | 6661-6679 | CTAGGGAAAAATAGCCTAC |
| 239 | NM_000044.3 | 6663-6681 | AGGGAAAAATAGCCTACAC |
| 240 | NM_000044.3 | 6673-6691 | AGCCTACACAAGCCTTTAG |
| 241 | NM_000044.3 | 6675-6693 | CCTACACAAGCCTTTAGGC |
| 242 | NM_000044.3 | 6677-6695 | TACACAAGCCTTTAGGCCT |
| 243 | NM_000044.3 | 6679-6697 | CACAAGCCTTTAGGCCTAC |
| 244 | NM_000044.3 | 6681-6699 | CAAGCCTTTAGGCCTACTC |

TABLE 2-continued

Androgen-receptor-specific oligonucleotide candidate sequence selected through 2-base sliding-window screening

| SEQ ID NO: | Accession No. | Position | Sense strand sequence |
|---|---|---|---|
| 245 | NM_000044.3 | 6711-6729 | GGGTTTGAGTGAACAAAGG |
| 246 | NM_000044.3 | 6787-6805 | TTTGGCCATTGATGTTCTA |
| 247 | NM_000044.3 | 6789-6807 | TGGCCATTGATGTTCTAGC |
| 248 | NM_000044.3 | 6833-6851 | TTGCATGCGCTCTGCTCTA |
| 249 | NM_000044.3 | 6835-6853 | GCATGCGCTCTGCTCTACA |
| 250 | NM_000044.3 | 6837-6855 | ATGCGCTCTGCTCTACAAA |
| 251 | NM_000044.3 | 6845-6863 | TGCTCTACAAACAGAGTTG |
| 252 | NM_000044.3 | 6847-6865 | CTCTACAAACAGAGTTGGT |
| 253 | NM_000044.3 | 6865-6883 | TATGGTTGGTATACTGTAC |
| 254 | NM_000044.3 | 6901-6919 | GCCACTCAGACCCACTTAG |
| 255 | NM_000044.3 | 6903-6921 | CACTCAGACCCACTTAGCT |
| 256 | NM_000044.3 | 6913-6931 | CACTTAGCTGGTGAGCTAG |
| 257 | NM_000044.3 | 6915-6933 | CTTAGCTGGTGAGCTAGAA |
| 258 | NM_000044.3 | 6979-6997 | AAGTTGGCAGTGCTCGATG |
| 259 | NM_000044.3 | 6981-6999 | GTTGGCAGTGCTCGATGTG |
| 260 | NM_000044.3 | 6989-7007 | TGCTCGATGTGGACGAAGA |
| 261 | NM_000044.3 | 6991-7009 | CTCGATGTGGACGAAGAGT |
| 262 | NM_000044.3 | 6999-7017 | GGACGAAGAGTGAGGAAGA |
| 263 | NM_000044.3 | 7095-7113 | TCAAAGAAAAGAGTCGTGT |
| 264 | NM_000044.3 | 7115-7133 | GCAGTTTCAGCTCTCGTTC |
| 265 | NM_000044.3 | 7119-7137 | TTTCAGCTCTCGTTCATTG |
| 266 | NM_000044.3 | 7123-7141 | AGCTCTCGTTCATTGGGCA |
| 267 | NM_000044.3 | 7125-7143 | CTCTCGTTCATTGGGCAGC |
| 268 | NM_000044.3 | 7127-7145 | CTCGTTCATTGGGCAGCTC |
| 269 | NM_000044.3 | 7129-7147 | CGTTCATTGGGCAGCTCGC |
| 270 | NM_000044.3 | 7169-7187 | ACATGGGAGTTGTTGGATT |
| 271 | NM_000044.3 | 7203-7221 | TTTTCTATGCCATAGGCAA |
| 272 | NM_000044.3 | 7205-7223 | TTCTATGCCATAGGCAATA |
| 273 | NM_000044.3 | 7263-7281 | TACTCTGAGAAAGGGATAT |
| 274 | NM_000044.3 | 7283-7301 | TTGAAGGACTGTCATATAT |
| 275 | NM_000044.3 | 7335-7353 | TTTATGTATGTTCACTGGC |
| 276 | NM_000044.3 | 7337-7355 | TATGTATGTTCACTGGCAC |
| 277 | NM_000044.3 | 7351-7369 | GGCACTAAAAAATATAGAG |
| 278 | NM_000044.3 | 7357-7375 | AAAAAATATAGAGAGCTTC |
| 279 | NM_000044.3 | 7413-7431 | GGTTGAAAAATAATGTGCT |
| 280 | NM_000044.3 | 7431-7449 | TGATGCTAGAGTCCCTCTC |

TABLE 2-continued

Androgen-receptor-specific oligonucleotide candidate sequence selected through 2-base sliding-window screening

| SEQ ID NO: | Accession No. | Position | Sense strand sequence |
|---|---|---|---|
| 281 | NM_000044.3 | 7433-7451 | ATGCTAGAGTCCCTCTCTG |
| 282 | NM_000044.3 | 7441-7459 | GTCCCTCTCTGTCCATACT |
| 283 | NM_000044.3 | 7487-7505 | TAGCAAGTTTTATTTGACT |
| 284 | NM_000044.3 | 7553-7571 | AGCTAACATTGAGCTTCAA |
| 285 | NM_000044.3 | 7585-7603 | GTTTGTTTCATTAGGCACA |
| 286 | NM_000044.3 | 7587-7605 | TTGTTTCATTAGGCACAGC |
| 287 | NM_000044.3 | 7593-7611 | CATTAGGCACAGCACAGAT |
| 288 | NM_000044.3 | 7647-7665 | CAGGGCATAAAGGCCCAGG |
| 289 | NM_000044.3 | 7695-7713 | ACCAAAGCTGCATTTCAGG |
| 290 | NM_000044.3 | 7709-7727 | TCAGGAGACTCTCTCCAGA |
| 291 | NM_000044.3 | 7721-7739 | CTCCAGACAGCCCAGTAAC |
| 292 | NM_000044.3 | 7727-7745 | ACAGCCCAGTAACTACCCG |
| 293 | NM_000044.3 | 7729-7747 | AGCCCAGTAACTACCCGAG |
| 294 | NM_000044.3 | 7731-7749 | CCCAGTAACTACCCGAGCA |
| 295 | NM_000044.3 | 7733-7751 | CAGTAACTACCCGAGCATG |
| 296 | NM_000044.3 | 7735-7753 | GTAACTACCCGAGCATGGC |
| 297 | NM_000044.3 | 7777-7795 | AGAGGCTGACTGTCTACGA |
| 298 | NM_000044.3 | 7779-7797 | AGGCTGACTGTCTACGAAT |
| 299 | NM_000044.3 | 7781-7799 | GCTGACTGTCTACGAATTA |
| 300 | NM_000044.3 | 7783-7801 | TGACTGTCTACGAATTATC |
| 301 | NM_000044.3 | 7785-7803 | ACTGTCTACGAATTATCTT |
| 302 | NM_000044.3 | 7791-7809 | TACGAATTATCTTGTGCCA |
| 303 | NM_000044.3 | 7793-7811 | CGAATTATCTTGTGCCAGT |
| 304 | NM_000044.3 | 7845-7863 | GGTTTTCATGTTTGACCCA |
| 305 | NM_000044.3 | 7847-7865 | TTTTCATGTTTGACCCACT |
| 306 | NM_000044.3 | 7969-7987 | TTCTACCCCTGATGCCTTT |
| 307 | NM_000044.3 | 7987-8005 | TGTAGGCAGATCTGTTCTC |
| 308 | NM_000044.3 | 7989-8007 | TAGGCAGATCTGTTCTCAC |
| 309 | NM_000044.3 | 8081-8099 | GATTACATTGTACCTGCTA |
| 310 | NM_000044.3 | 8083-8101 | TTACATTGTACCTGCTAAG |
| 311 | NM_000044.3 | 8087-8105 | ATTGTACCTGCTAAGATAC |
| 312 | NM_000044.3 | 8109-8127 | AATTCATAAGGGCAGGGGG |
| 313 | NM_000044.3 | 8123-8141 | GGGGGGGAGCAAGCATTAG |
| 314 | NM_000044.3 | 8125-8143 | GGGGGAGCAAGCATTAGTG |
| 315 | NM_000044.3 | 8127-8145 | GGGAGCAAGCATTAGTGCC |
| 316 | NM_000044.3 | 8145-8163 | CTCTTTGATAAGCTGTCCA |
| 317 | NM_000044.3 | 8149-8167 | TTGATAAGCTGTCCAAAGA |
| 318 | NM_000044.3 | 8167-8185 | ACAGACTAAAGGACTCTGC |
| 319 | NM_000044.3 | 8185-8203 | CTGGTGACTGACTTATAAG |
| 320 | NM_000044.3 | 8187-8205 | GGTGACTGACTTATAAGAG |
| 321 | NM_000044.3 | 8191-8209 | ACTGACTTATAAGAGCTTT |
| 322 | NM_000044.3 | 8279-8297 | ATGGGTCCTTCACTAAGTG |
| 323 | NM_000044.3 | 8301-8319 | TTATAAGCAGAACTGGCTT |
| 324 | NM_000044.3 | 8323-8341 | TTTTCTCTAGTAGTTGCTG |
| 325 | NM_000044.3 | 8327-8345 | CTCTAGTAGTTGCTGAGCA |
| 326 | NM_000044.3 | 8343-8361 | GCAAATTGTTGAAGCTCCA |
| 327 | NM_000044.3 | 8349-8367 | TGTTGAAGCTCCATCATTG |
| 328 | NM_000044.3 | 8351-8369 | TTGAAGCTCCATCATTGCA |
| 329 | NM_000044.3 | 8353-8371 | GAAGCTCCATCATTGCATG |
| 330 | NM_000044.3 | 8355-8373 | AGCTCCATCATTGCATGGT |
| 331 | NM_000044.3 | 8357-8375 | CTCCATCATTGCATGGTTG |
| 332 | NM_000044.3 | 8359-8377 | CCATCATTGCATGGTTGGA |
| 333 | NM_000044.3 | 8361-8379 | ATCATTGCATGGTTGGAAA |
| 334 | NM_000044.3 | 8393-8411 | AGCCACTGTGTTTGCTAGT |
| 335 | NM_000044.3 | 8405-8423 | TGCTAGTGCCCATGTTAGC |
| 336 | NM_000044.3 | 8407-8425 | CTAGTGCCCATGTTAGCTT |
| 337 | NM_000044.3 | 8447-8465 | GCTGATAAGGGAGCATTTA |
| 338 | NM_000044.3 | 8449-8467 | TGATAAGGGAGCATTTAAA |
| 339 | NM_000044.3 | 8455-8473 | GGGAGCATTTAAAGTACTA |
| 340 | NM_000044.3 | 8529-8547 | GGCACAAAAAGTTATCTGC |
| 341 | NM_000044.3 | 8539-8557 | GTTATCTGCAGTTGAAGGC |
| 342 | NM_000044.3 | 8659-8677 | GTGTGTGTTCTGATAGCTT |
| 343 | NM_000044.3 | 8735-8753 | TGAGAGAGGATGCAGTTTT |
| 344 | NM_000044.3 | 8783-8801 | ACACCTGGATTGATCAGTT |
| 345 | NM_000044.3 | 8785-8803 | ACCTGGATTGATCAGTTAA |
| 346 | NM_000044.3 | 8787-8805 | CTGGATTGATCAGTTAACT |
| 347 | NM_000044.3 | 8789-8807 | GGATTGATCAGTTAACTAA |
| 348 | NM_000044.3 | 8793-8811 | TGATCAGTTAACTAAAAGT |
| 349 | NM_000044.3 | 8795-8813 | ATCAGTTAACTAAAAGTTT |
| 350 | NM_000044.3 | 8797-8815 | CAGTTAACTAAAAGTTTTC |
| 351 | NM_000044.3 | 8817-8835 | CCCCTATTGGGTTTGACCC |
| 352 | NM_000044.3 | 8819-8837 | CCTATTGGGTTTGACCCAC |

TABLE 2-continued

Androgen-receptor-specific oligonucleotide candidate sequence selected through 2-base sliding-window screening

| SEQ ID NO: | Accession No. | Position | Sense strand sequence |
|---|---|---|---|
| 353 | NM_000044.3 | 8825-8843 | GGGTTTGACCCACAGGTCC |
| 354 | NM_000044.3 | 8857-8875 | AGGGATAAAAAGAGTAGAG |
| 355 | NM_000044.3 | 8871-8889 | TAGAGGACATGATACATTG |
| 356 | NM_000044.3 | 8873-8891 | GAGGACATGATACATTGTA |
| 357 | NM_000044.3 | 8881-8899 | GATACATTGTACTTTACTA |
| 358 | NM_000044.3 | 8893-8911 | TTTACTAGTTCAAGACAGA |
| 359 | NM_000044.3 | 8897-8915 | CTAGTTCAAGACAGATGAA |
| 360 | NM_000044.3 | 8989-9007 | CCTACCCAAGTGATTGACC |
| 361 | NM_000044.3 | 9001-9019 | ATTGACCAGTGGCCCCCTA |
| 362 | NM_000044.3 | 9003-9021 | TGACCAGTGGCCCCCTAAT |
| 363 | NM_000044.3 | 9009-9027 | GTGGCCCCCTAATGGGACC |
| 364 | NM_000044.3 | 9015-9033 | CCCTAATGGGACCTGAGCT |
| 365 | NM_000044.3 | 9017-9035 | CTAATGGGACCTGAGCTGT |
| 366 | NM_000044.3 | 9083-9101 | GGGCAGTTTCCTGCATTGG |
| 367 | NM_000044.3 | 9095-9113 | GCATTGGAACCTGGAGCAA |
| 368 | NM_000044.3 | 9101-9119 | GAACCTGGAGCAAGCGCTC |
| 369 | NM_000044.3 | 9107-9125 | GGAGCAAGCGCTCTATCTT |
| 370 | NM_000044.3 | 9109-9127 | AGCAAGCGCTCTATCTTTC |
| 371 | NM_000044.3 | 9111-9129 | CAAGCGCTCTATCTTTCAC |
| 372 | NM_000044.3 | 9113-9131 | AGCGCTCTATCTTTCACAC |
| 373 | NM_000044.3 | 9125-9143 | TTCACACAAATTCCCTCAC |
| 374 | NM_000044.3 | 9127-9145 | CACACAAATTCCCTCACCT |
| 375 | NM_000044.3 | 9151-9169 | TGAGGTGCTCTTGTTACTG |
| 376 | NM_000044.3 | 9153-9171 | AGGTGCTCTTGTTACTGGG |
| 377 | NM_000044.3 | 9155-9173 | GTGCTCTTGTTACTGGGTG |
| 378 | NM_000044.3 | 9157-9175 | GCTCTTGTTACTGGGTGTC |
| 379 | NM_000044.3 | 9161-9179 | TTGTTACTGGGTGTCTGTG |
| 380 | NM_000044.3 | 9175-9193 | CTGTGTGCTGTAATTCTGG |
| 381 | NM_000044.3 | 9177-9195 | GTGTGCTGTAATTCTGGTT |
| 382 | NM_000044.3 | 9239-9257 | TTCTCTGTTAAAACTTGTC |
| 383 | NM_000044.3 | 9249-9267 | AAACTTGTCAGAGTACTAG |
| 384 | NM_000044.3 | 9251-9269 | ACTTGTCAGAGTACTAGAA |
| 385 | NM_000044.3 | 9253-9271 | TTGTCAGAGTACTAGAAGT |
| 386 | NM_000044.3 | 9261-9279 | GTACTAGAAGTTGTATCTC |
| 387 | NM_000044.3 | 9271-9289 | TTGTATCTCTGTAGGTGCA |
| 388 | NM_000044.3 | 9325-9343 | TGATTAAGAGATTGACACT |

TABLE 2-continued

Androgen-receptor-specific oligonucleotide candidate sequence selected through 2-base sliding-window screening

| SEQ ID NO: | Accession No. | Position | Sense strand sequence |
|---|---|---|---|
| 389 | NM_000044.3 | 9327-9345 | ATTAAGAGATTGACACTTC |
| 390 | NM_000044.3 | 9329-9347 | TAAGAGATTGACACTTCTG |
| 391 | NM_000044.3 | 9339-9357 | ACACTTCTGTTGCCTAGGA |
| 392 | NM_000044.3 | 9341-9359 | ACTTCTGTTGCCTAGGACC |
| 393 | NM_000044.3 | 9343-9361 | TTCTGTTGCCTAGGACCTC |
| 394 | NM_000044.3 | 9345-9363 | CTGTTGCCTAGGACCTCCC |
| 395 | NM_000044.3 | 9379-9397 | AGGTGAAGGCAGAAAAATC |
| 396 | NM_000044.3 | 9401-9419 | ATTAGTTACTCCTCTTCAG |
| 397 | NM_000044.3 | 9403-9421 | TAGTTACTCCTCTTCAGAC |
| 398 | NM_000044.3 | 9551-9569 | ATTTGGCCAGAAAGTAGGT |
| 399 | NM_000044.3 | 9563-9581 | AGTAGGTAATATGCATTGA |
| 400 | NM_000044.3 | 9565-9583 | TAGGTAATATGCATTGATT |
| 401 | NM_000044.3 | 9567-9585 | GGTAATATGCATTGATTGG |
| 402 | NM_000044.3 | 9571-9589 | ATATGCATTGATTGGCTTC |
| 403 | NM_000044.3 | 9573-9591 | ATGCATTGATTGGCTTCTG |
| 404 | NM_000044.3 | 9599-9617 | TTCAGTATAGCAAGGTGCT |
| 405 | NM_000044.3 | 9601-9619 | CAGTATAGCAAGGTGCTAG |
| 406 | NM_000044.3 | 9603-9621 | GTATAGCAAGGTGCTAGGT |
| 407 | NM_000044.3 | 9609-9627 | CAAGGTGCTAGGTTTTTTC |
| 408 | NM_000044.3 | 9671-9689 | CTTAGAATGGGTGGCCCTT |
| 409 | NM_000044.3 | 9705-9723 | TCCCACATAAGCTACTTAA |
| 410 | NM_000044.3 | 9707-9725 | CCACATAAGCTACTTAACA |
| 411 | NM_000044.3 | 9719-9737 | CTTAACAAGATTGTCATGG |
| 412 | NM_000044.3 | 9737-9755 | GAGCTGCAGATTCCATTGC |
| 413 | NM_000044.3 | 9751-9769 | ATTGCCCACCAAAGACTAG |
| 414 | NM_000044.3 | 9855-9873 | GTATGGGAACCTGTACTCT |
| 415 | NM_000044.3 | 9893-9911 | TTTGCATTATCTCACAACC |
| 416 | NM_000044.3 | 9895-9913 | TGCATTATCTCACAACCTT |
| 417 | NM_000044.3 | 9897-9915 | CATTATCTCACAACCTTAG |
| 418 | NM_000044.3 | 9905-9923 | CACAACCTTAGCCCTTGGT |
| 419 | NM_000044.3 | 9907-9925 | CAACCTTAGCCCTTGGTGC |
| 420 | NM_000044.3 | 9911-9929 | CTTAGCCCTTGGTGCTAAC |
| 421 | NM_000044.3 | 9913-9931 | TAGCCCTTGGTGCTAACTG |
| 422 | NM_000044.3 | 9919-9937 | TTGGTGCTAACTGTCCTAC |
| 423 | NM_000044.3 | 9925-9943 | CTAACTGTCCTACAGTGAA |
| 424 | NM_000044.3 | 9927-9945 | AACTGTCCTACAGTGAAGT |

TABLE 2-continued

Androgen-receptor-specific oligonucleotide candidate sequence selected through 2-base sliding-window screening

| SEQ ID NO: | Accession No. | Position | Sense strand sequence |
|---|---|---|---|
| 425 | NM_000044.3 | 9939-9957 | GTGAAGTGCCTGGGGGGTT |
| 426 | NM_000044.3 | 9941-9959 | GAAGTGCCTGGGGGGTTGT |
| 427 | NM_000044.3 | 9947-9965 | CCTGGGGGGTTGTCCTATC |
| 428 | NM_000044.3 | 9949-9967 | TGGGGGGTTGTCCTATCCC |
| 429 | NM_000044.3 | 9951-9969 | GGGGGTTGTCCTATCCCAT |
| 430 | NM_000044.3 | 9953-9971 | GGGTTGTCCTATCCCATAA |
| 431 | NM_000044.3 | 9955-9973 | GTTGTCCTATCCCATAAGC |
| 432 | NM_000044.3 | 9957-9975 | TGTCCTATCCCATAAGCCA |
| 433 | NM_000044.3 | 9959-9977 | TCCTATCCCATAAGCCACT |
| 434 | NM_000044.3 | 10003-10021 | GAATGACCCACGCAAAAAA |
| 435 | NM_000044.3 | 10039-10057 | AAAGTCCCCTCACAACCCA |
| 436 | NM_000044.3 | 10041-10059 | AGTCCCCTCACAACCCAGT |
| 437 | NM_000044.3 | 10043-10061 | TCCCCTCACAACCCAGTGA |
| 438 | NM_000044.3 | 10051-10069 | CAACCCAGTGACACCTTTC |
| 439 | NM_000044.3 | 10053-10071 | ACCCAGTGACACCTTTCTG |
| 440 | NM_000044.3 | 10075-10093 | TCCTCTAGACTGGAACATT |
| 441 | NM_000044.3 | 10077-10095 | CTCTAGACTGGAACATTGA |
| 442 | NM_000044.3 | 10099-10117 | GGGAGTGCCTCAGACATGA |
| 443 | NM_000044.3 | 10101-10119 | GAGTGCCTCAGACATGACA |
| 444 | NM_000044.3 | 10103-10121 | GTGCCTCAGACATGACATT |
| 445 | NM_000044.3 | 10163-10181 | AGACTATGTAAACAGAGAT |
| 446 | NM_000044.3 | 10287-10305 | TTTAGATGGGGCTCATTTC |
| 447 | NM_000044.3 | 10299-10317 | TCATTTCTCACGGTGGCAC |
| 448 | NM_000044.3 | 10301-10319 | ATTTCTCACGGTGGCACTT |
| 449 | NM_000044.3 | 10341-10359 | CCAGCTCCAAGCGCTAGTG |
| 450 | NM_000044.3 | 10343-10361 | AGCTCCAAGCGCTAGTGTT |
| 451 | NM_000044.3 | 10347-10365 | CCAAGCGCTAGTGTTCTGT |
| 452 | NM_000044.3 | 10349-10367 | AAGCGCTAGTGTTCTGTTC |
| 453 | NM_000044.3 | 10383-10401 | GGAATCTTTTGTTGCTCTA |
| 454 | NM_000044.3 | 10413-10431 | AAATGGCAGAAACTTGTTT |
| 455 | NM_000044.3 | 10481-10499 | AATGTCATCCATTGTGTAA |
| 456 | NM_000044.3 | 10499-10517 | AAATATTGGCTTACTGGTC |
| 457 | NM_000044.3 | 10501-10519 | ATATTGGCTTACTGGTCTG |
| 458 | NM_000044.3 | 10535-10553 | CCACATCCCCTGTTATGGC |
| 459 | NM_000044.3 | 10537-10555 | ACATCCCCTGTTATGGCTG |
| 460 | NM_000044.3 | 10541-10559 | CCCCTGTTATGGCTGCAGG |
| 461 | NM_000044.3 | 10543-10561 | CCTGTTATGGCTGCAGGAT |
| 462 | NM_000044.3 | 10545-10563 | TGTTATGGCTGCAGGATCG |
| 463 | NM_000044.3 | 10553-10571 | CTGCAGGATCGAGTTATTG |
| 464 | NM_000044.3 | 10555-10573 | GCAGGATCGAGTTATTGTT |
| 465 | NM_000044.3 | 10557-10575 | AGGATCGAGTTATTGTTAA |
| 466 | NM_000044.3 | 10559-10577 | GATCGAGTTATTGTTAACA |
| 467 | NM_000044.3 | 10601-10619 | ATGTCCTCTTATCATTGTT |
| 468 | NM_000044.3 | 10603-10621 | GTCCTCTTATCATTGTTGT |
| 545 | — | — | CTTACGCTGAGTACTTCGA |

TABLE 3

Androgen-receptor-specific siRNA sequence described in related literature (US 2007-0141009A)

| SEQ ID NO: | Related Patent | Position | Sense strand sequence |
|---|---|---|---|
| 469 | US2007-0141009A1 | 1122-1140 | GUGCAGUUAGGGCUGGGAA |
| 470 | US2007-0141009A1 | 1141-1159 | GGGUCUACCCUCGGCCGCC |
| 471 | US2007-0141009A1 | 1190-1208 | UCUGUUCCAGAGCGUGCGC |
| 472 | US2007-0141009A1 | 1212-1230 | GUGAUCCAGAACCCGGGCC |
| 473 | US2007-0141009A1 | 1455-1473 | CAGCAACCUUCACAGCCGC |
| 474 | US2007-0141009A1 | 1544-1562 | GGGGCUGCCGCAGCAGCUG |
| 475 | US2007-0141009A1 | 1661-1679 | AGACAUCCUGAGCGAGGCC |
| 476 | US2007-0141009A1 | 1692-1710 | CUCCUUCAGCAACAGCAGC |
| 477 | US2007-0141009A1 | 1728-1746 | GGCAGCAGCAGCGGGAGAG |
| 478 | US2007-0141009A1 | 1781-1799 | GGACAAUUACUUAGGGGGC |
| 479 | US2007-0141009A1 | 1787-1805 | UUACUUAGGGGGCACUUCG |
| 480 | US2007-0141009A1 | 1838-1856 | GGCAGUGUCGGUGUCCAUG |
| 481 | US2007-0141009A1 | 1899-1917 | CAGCUUCGGGGGGAUUGCA |
| 482 | US2007-0141009A1 | 1983-2001 | UGCAAAGGUUCUCUGCUAG |
| 483 | US2007-0141009A1 | 1988-2006 | AGGUUCUCUGCUAGACGAC |
| 484 | US2007-0141009A1 | 2018-2036 | GAGCACUGAAGAUACUGCU |
| 485 | US2007-0141009A1 | 2028-2046 | GAUACUGCUGAGUAUUCCC |
| 486 | US2007-0141009A1 | 2054-2072 | GGGAGGUUACACCAAAGGG |
| 487 | US2007-0141009A1 | 2079-2097 | GGCGAGAGCCUAGGCUGCU |
| 488 | US2007-0141009A1 | 2162-2180 | GUCCGGAGCACUGGACGAG |
| 489 | US2007-0141009A1 | 2213-2231 | CUUUCCACUGGCUCUGGCC |

TABLE 3-continued

Androgen-receptor-specific siRNA sequence described in related literature (US 2007-0141009A)

| SEQ ID NO: | Related Patent | Position | Sense strand sequence |
|---|---|---|---|
| 490 | US2007-0141009A1 | 2279-2297 | GCUGGAGAACCCGCUGGAC |
| 491 | US2007-0141009A1 | 2288-2306 | CCCGCUGGACUACGGCAGC |
| 492 | US2007-0141009A1 | 2442-2460 | GAAGGCCAGUUGUAUGGAC |
| 493 | US2007-0141009A1 | 2445-2463 | GGCCAGUUGUAUGGACCGU |
| 494 | US2007-0141009A1 | 2678-2696 | AAGCGAAAUGGGCCCCUGG |
| 495 | US2007-0141009A1 | 2680-2698 | GCGAAAUGGGCCCCUGGAU |
| 496 | US2007-0141009A1 | 2685-2703 | AUGGGCCCCUGGAUGGAUA |
| 497 | US2007-0141009A1 | 2814-2832 | GCUUCUGGGUGUCACUAUG |
| 498 | US2007-0141009A1 | 2858-2876 | GGUCUUCUUCAAAAGAGCC |
| 499 | US2007-0141009A1 | 2870-2888 | AAGAGCCGCUGAAGGGAAA |
| 500 | US2007-0141009A1 | 2872-2890 | GAGCCGCUGAAGGGAAACA |
| 501 | US2007-0141009A1 | 2883-2901 | GGGAAACAGAAGUACCUGU |
| 502 | US2007-0141009A1 | 2888-2906 | ACAGAAGUACCUGUGCGCC |
| 503 | US2007-0141009A1 | 2894-2912 | GUACCUGUGCGCCAGCAGA |
| 504 | US2007-0141009A1 | 2933-2951 | AUUCCGAAGGAAAAAUUGU |
| 505 | US2007-0141009A1 | 2941-2959 | GGAAAAAUUGUCCAUCUUG |
| 506 | US2007-0141009A1 | 2945-2963 | AAAUUGUCCAUCUUGUCGU |
| 507 | US2007-0141009A1 | 2947-2965 | AUUGUCCAUCUUGUCGUCU |
| 508 | US2007-0141009A1 | 2982-3000 | GCAGGGAUGACUCUGGGAG |
| 509 | US2007-0141009A1 | 3008-3026 | GCUGAAGAAACUUGGUAAU |
| 510 | US2007-0141009A1 | 3014-3032 | GAAACUUGGUAAUCUGAAA |
| 511 | US2007-0141009A1 | 3017-3035 | ACUUGGUAAUCUGAAACUA |
| 512 | US2007-0141009A1 | 3045-3063 | GGAGAGGCUUCCAGCACCA |
| 513 | US2007-0141009A1 | 3114-3132 | GGCUAUGAAUGUCAGCCCA |
| 514 | US2007-0141009A1 | 3123-3141 | UGUCAGCCCAUCUUUCUGA |
| 515 | US2007-0141009A1 | 3191-3209 | CAACCAGCCCGACUCCUUU |
| 516 | US2007-0141009A1 | 3194-3212 | CCAGCCCGACUCCUUUGCA |
| 517 | US2007-0141009A1 | 3233-3251 | UGAACUGGGAGAGAGACAG |
| 518 | US2007-0141009A1 | 3237-3255 | CUGGGAGAGAGACAGCUUG |
| 519 | US2007-0141009A1 | 3278-3296 | GGCCUUGCCUGGCUUCCGC |
| 520 | US2007-0141009A1 | 3299-3317 | CUUACACGUGGACGACCAG |
| 521 | US2007-0141009A1 | 3431-3449 | UGAGUACCGCAUGCACAAG |
| 522 | US2007-0141009A1 | 3478-3496 | UGAGGCACCUCUCUCAAGA |
| 523 | US2007-0141009A1 | 3495-3513 | GAGUUUGGAUGGCUCCAAA |
| 524 | US2007-0141009A1 | 3528-3546 | UUCCUGUGCAUGAAAGCAC |
| 525 | US2007-0141009A1 | 3542-3560 | AGCACUGCUACUCUUCAGC |
| 526 | US2007-0141009A1 | 3584-3602 | AAAUCAAAAAUUCUUUGAU |
| 527 | US2007-0141009A1 | 3586-3604 | AUCAAAAAUUCUUUGAUGA |
| 528 | US2007-0141009A1 | 3591-3609 | AAAUUCUUUGAUGAACUUC |
| 529 | US2007-0141009A1 | 3593-3611 | AUUCUUUGAUGAACUUCGA |
| 530 | US2007-0141009A1 | 3606-3624 | CUUCGAAUGAACUACAUCA |
| 531 | US2007-0141009A1 | 3613-3631 | UGAACUACAUCAAGGAACU |
| 532 | US2007-0141009A1 | 3617-3635 | CUACAUCAAGGAACUCGAU |
| 533 | US2007-0141009A1 | 3653-3671 | AAGAAAAAAUCCCACAUCC |
| 534 | US2007-0141009A1 | 3655-3673 | GAAAAAAUCCCACAUCCUG |
| 535 | US2007-0141009A1 | 3658-3676 | AAAAUCCCACAUCCUGCUC |
| 536 | US2007-0141009A1 | 3660-3678 | AAUCCCACAUCCUGCUCAA |
| 537 | US2007-0141009A1 | 3662-3680 | UCCCACAUCCUGCUCAAGA |
| 538 | US2007-0141009A1 | 3701-3719 | GCUCCUGGACUCCGUGCAG |
| 539 | US2007-0141009A1 | 3763-3781 | UCAAGUCACACAUGGUGAG |
| 540 | US2007-0141009A1 | 3767-3785 | GUCACACAUGGUGAGCGUG |
| 541 | US2007-0141009A1 | 3825-3843 | GUGCCCAAGAUCCUUUCUG |
| 542 | US2007-0141009A1 | 3833-3851 | GAUCCUUUCUGGGAAAGUC |
| 543 | US2007-0141009A1 | 3848-3866 | AGUCAAGCCCAUCUAUUUC |
| 544 | US2007-0141009A1 | 3854-3872 | GCCCAUCUAUUUCCACACC |

Example 2. Synthesis of Double Stranded Oligonucleotide Construct

The double stranded oligonucleotide construct (SAMiRNA) manufactured in the present invention has the structure represented by the following Structural Formula.

A—X—S—Y—B pAS

The synthesis process includes repeating the cycle including deblocking, coupling, capping, and oxidation on a solid support (CPG) to which the nucleoside was attached, thereby obtaining an RNA single strand having a desired sequence. An RNA synthesizer (384 synthesizer, BIONEER, Korea) was used for a series of processes of synthesis of double stranded oligo RNA.

The sense strand of the double stranded oligonucleotide construct was manufactured by linking phosphodiester bonds constituting a DNA backbone using β-cyanoethylphosphoamidite on polyethylene glycol (PEG)-CPG as a support to synthesize a construct of a double stranded oligonucleotide having a sense strand having polyethylene glycol bound to the 3' end and a hydrophilic material, after which $C_{24}$ containing a disulfide bond was bound to the 5' end. For an antisense strand to be annealed with the sense strand, an antisense strand having a sequence complementary to the sense strand was manufactured by linking phosphodiester bonds constituting an RNA backbone using β-cyanoethylphosphoamidite, after which an antisense strand having a phosphate group bound to the 5' end was manufactured using a chemical phosphorylation reagent (CPR) for attaching a phosphate group to the 5' end.

After completion of synthesis, the synthesized oligonucleotide single strand and oligonucleotide-polymer construct were separated from CPG using 28% (v/v) ammonia in a water bath at 60° C., followed by deprotection to remove the protective residue. The deprotected oligonucleotide single strand and oligonucleotide-polymer construct were treated with N-methylpyrrolidone, triethylamine and triethylaminetrihydrofluoride at a volume ratio of 10:3:4 in an oven at 70° C., thus removing 2'. The oligonucleotide single strand, the oligonucleotide-polymer construct, and the ligand-bound oligonucleotide-polymer construct were separated from the reaction mixture through high-performance liquid chromatography (HPLC), and the molecular weights thereof were measured using a MALDI-TOF mass spectrometer (SHIMADZU, Japan), and whether the resultant products matched the base sequence and oligonucleotide-polymer construct to be synthesized was confirmed. Thereafter, in order to manufacture each double stranded oligonucleotide construct, the sense strand and the antisense strand were mixed in the same amount and placed in a 1× annealing buffer (30 mM HEPES, 100 mM potassium acetate, and 2 mM magnesium acetate) at a pH of 7.0 or more, allowed to react for 3 minutes in a constant-temperature water bath at 90° C., and then allowed to react again at 37° C., thereby manufacturing desired SAMiRNA, monoSAMiRNA (n=1), monoSAMiRNA (n=2), monoSAMiRNA (n=3), and monoSAMiRNA (n=4). The annealing of the double stranded oligonucleotide constructs thus manufactured was confirmed through electrophoresis.

Example 3. Screening of SAMiRNA Nanoparticles Inducing RNAi by Targeting Androgen Receptor

3.1 Manufacture and Particle Size Analysis of SAMiRNA Nanoparticles

Based on the results of measurement of the size and polydispersity index of SAMiRNA using a Zetasizer Nano ZS (Malvern, UK) for particle size analysis of 544 types of SAMiRNAs targeting the androgen receptor sequence synthesized in Example 2, the size and polydispersity index of the nanoparticles for the randomly selected SAMiRNAs are shown in Table 4 below, and a representative graph thereof is shown in FIG. 3.

TABLE 4

Nanoparticle size and polydispersity index of androgen-receptor-specific SAMiRNA

| SEQ ID NO: | Code Name | Size | PDI |
|---|---|---|---|
| 545 | SAMi-CON | 28 ± 1.0 | 0.28 ± 0.04 |
| 10 | SAMi-AR #10 | 27.8 ± 0.7 | 0.18 ± 0.07 |

3.2 Intracellular Treatment Method of SAMiRNA Nanoparticles

LNCaP, which is a human-derived prostate cancer cell line, was used to discover SAMiRNA, which inhibits the expression of an androgen receptor, and the LNCaP cell line was cultured at 37° C. and 5% $CO_2$ using an RPMI medium (HyClone, US) containing 10% fetal bovine serum (HyClone, US) and 1% penicillin-streptomycin (HyClone, US). Using the same medium as above, the LNCaP cell line was dispensed at $4\times10^4$ cells/well into a 12-well plate (Costar, US), and on the next day, SAMiRNA was diluted with 1×DPBS and used to treat the cells at 50 nM. SAMiRNA was treated a total of 4 times under the condition of treatment once every 12 hours, and was cultured at 37° C. and 5% $CO_2$.

3.3 SAMiRNA Screening Through Analysis of Efficacy of Inhibiting Expression of Androgen Receptor mRNA RNA extracted from the SAMiRNA-treated cells as in Example 3.2 was synthesized into cDNA using AccuPower® RocketScript™ Cycle RT Premix with oligo (dT) 20, after which the relative expression level of the androgen receptor gene was analyzed compared to the SAMiRNA control sample using the Taqman-probe-type multiplex qPCR method.

As a result, as shown in FIG. 4, 9 sequences mentioned in the related patent (US 2007-0141009A) and 14 sequences in Table 2 were selected out of sequences showing ability to inhibit the expression of the androgen receptor mRNA by 60% or more from among 544 types of SAMiRNAs targeting the androgen receptor (FIG. 5), and the results of re-evaluation of the ability of 14 sequences to inhibit the expression of the androgen receptor mRNA are shown in FIG. 6. Two types of SAMiRNAs that most effectively inhibit the expression of the androgen receptor gene were finally selected, and the sequence information of the corresponding SAMiRNAs is shown in Table 5 below.

TABLE 5

SAMiRNA sequence that effectively inhibits expression of androgen receptor

| SEQ ID NO: | Code Name | Position | Sense strand sequence |
|---|---|---|---|
| 68 | SAMi-AR #68 | 3495-3513 | GAGTTTGGATGGCTCCAAA |
| 109 | SAMi-AR #109 | 3991-4009 | ATGTACAGTCTGTCATGAA |

3.4 Evaluation of Efficacy of Selected SAMiRNA on Inhibiting Expression of Androgen Receptor Protein Western blot (WB) assay was performed in order to confirm whether 14 types of SAMiRNAs selected together including Nos. 68 and 109 sequences selected in Example 3.3 effectively inhibit the expression of the androgen receptor protein. The LNCaP cell line was dispensed at $1.2\times10^5$ cells/well into a 6-well plate (Costar, US) and cultured at 37° C. and 5% $CO_2$. The next day, transfection was performed at a concentration of 50 nM using lipofectamine (Invitrogen, USA). After culture for 48 hours, the medium was removed and the protein was isolated using a cell lysis buffer (Cell Signaling Technology, USA) containing a protease inhibitor cocktail (Sigma Aldrich, USA). After quantifying the amount of protein using a BCA assay kit (Thermo, USA), 20□ of protein was boiled at 95° C. for 10 minutes along with a Laemmli's 5× sample buffer. The denatured protein was electrophoresed on an SDS-polyacrylamide gel and then transferred to a PVDF membrane. The membrane was immersed in a blocking solution (5% non-fat dry milk in TBS and 0.05% Tween 20) and treated for 1 hour at room temperature, followed by reaction in a 4° C. refrigerator overnight along with a primary antibody AR antibody (1:2000, Santa Cruz, USA) and GAPDH antibody (1:5000, Cell Signaling Technology, USA), washing three times with TBST, and then reaction for 1 hour at room temperature with a horseradish-peroxidase-conjugated secondary antibody (Cell Signaling Technology), after which the protein band was detected using, as a chemiluminescent reagent, SuperSignal® Pico Chemiluminescent Substrate (Thermo, USA).

The ability of 14 types of SAMiRNAs to inhibit the expression of the androgen receptor protein was confirmed as shown in FIG. 7, and the inhibitory ability of Nos. 68 and 109 sequences was also vastly superior in protein expression.

3.5 Evaluation of Efficacy of Inhibition of Expression of Androgen Receptor Protein in Hair Follicle Dermal Papilla Cell (HFDPC) as Human-Derived Hair Root Cell In order to confirm whether SEQ ID NOS: 68 and 109 finally selected in Example 3.4 actually inhibit the expression of the androgen receptor protein in human hair root cells, the extent of inhibition of protein expression was measured using human-derived hair root cells, namely hair follicle dermal papilla cells (HFDPCs) (FIG. 8). Both sequences were found to be capable of inhibiting the expression of the androgen receptor protein.

Example 4. Confirmation of Intradermal Delivery Effect of SAMiRNA Nanoparticles In order to confirm whether SAMiRNA-AR #68 and SAMiRNA-AR #109 manufactured with finally selected SEQ ID NOS: 68 and 109 are actually delivered to human hair roots, the effect of gene transfer was measured in human hair.

Hair was collected by pulling the tip of the hair on the day of the experiment, cut to a length of about 1 cm from the root, and cultured in an incubator for 1 hour using 200 □ of a M199 medium (10% FBS+1% penicillin) in a 96-well plate. Thereafter, in order to observe gene transfer, culture was performed in an incubator for 24 hours using 200 □ of a M199 medium containing 2 μM and 10 μM SAMiRNA labeled with a fluorescent material (FAM dye). After 24 hours of material treatment, washing was performed three times using DPBS, and finally, the hair roots were fixed for 20 minutes in PBS containing 3.7% formaldehyde and 2% FBS.

The hair roots that had been fixed were planted in the base mold containing the OCT compound and placed on a pre-frozen stainless plate to completely freeze the OCT compound. The frozen tissues were stored at −70° C. and allowed to stand at −20° C. for about 30 minutes to facilitate tissue sectioning before cutting with a tissue-sectioning machine. The sectioned tissue was placed on a slide to a thickness of 10 μm and dried for 1 hour, and after drying, a mounting process was performed. Here, a mounting medium containing DAPI was used. Based on the result of observation of fluorescence using a confocal laser scanning microscope (LSM5 LIVE CONFIGURATION VARIOTWO VRGB), it was confirmed that the SAMiRNA was delivered to the hair root cells of the hair tissue (FIG. 9).

Although specific embodiments of the present invention have been disclosed in detail as described above, it will be obvious to those skilled in the art that the description is merely of preferable exemplary embodiments and is not to be construed as limiting the scope of the present invention. Therefore, the substantial scope of the present invention will be defined by the appended claims and equivalents thereof.

INDUSTRIAL APPLICABILITY

According to the present invention, a double stranded oligonucleotide construct including an androgen-receptor-specific oligonucleotide and a composition for preventing hair loss or promoting hair growth containing the same as an active ingredient can suppress the expression of an androgen receptor with high efficiency without side effects, and can thus exhibit excellent effects on preventing hair loss, particularly androgenetic alopecia, alopecia areata, and telogen effluvium, and promoting hair growth.

SEQUENCE LIST FREE TEXT

An electronic file is attached.

---

The invention claimed is:

1. A double stranded oligonucleotide construct for inhibiting androgen receptor gene expression, having a structure of Structure Formula (1) below:

A-X—R—Y—B     Structural Formula (1)

wherein in Structural Formula (1):

A is a hydrophilic material any one selected from the group consisting of polyethylene glycol (PEG), polyvinylpyrrolidone, polyoxazoline and a hydrophilic material having a structure of Structural Formula (5) or Structural Formula (6) below:

$(A'_m-J)_n$     Structural Formula (5)

$(J-A'_m)_n$     Structural Formula (6)

wherein in Structural Formula (5) and Structural Formula (6), A' is a hydrophilic material monomer, J is a linker for connecting m hydrophilic material monomers to each other or connecting m hydrophilic material monomers and an oligonucleotide to each other, m is an integer of 1 to 15, and n is an integer of 1 to 10, the hydrophilic material monomer A' being any one compound selected from among Compound (1) to Compound (3) below, and the linker (J) being selected from the group consisting of $PO_3^-$, $SO_3$, and $CO_2$,

| Compound (1) | Compound (2) | Compound (3) |
|---|---|---|
| 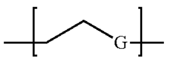 G is O, S, or NH | 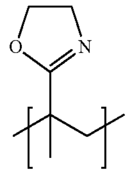 | 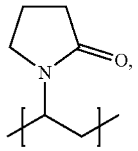 |

B is a hydrophobic material selected from the group consisting of a steroid derivative, a glyceride derivative, glycerol ether, polypropylene glycol, a $C_{12}$-$C_{50}$ unsaturated or saturated hydrocarbon, diacylphosphatidylcholine, fatty acid, phospholipid, and lipopolyamine, wherein the steroid derivative is selected from the group consisting of cholesterol, cholestanol, cholic acid, cholesteryl formate, cholestanyl formate, and cholesteryl amine, wherein the glyceride derivative is selected from the group consisting of mono-, di- and tri-glycerides, each of X and Y independently represents a simple covalent bond or a linker-mediated covalent bond, and R represents a DNA-RNA hybrid androgen-receptor-specific oligonucleotide comprising (i) a DNA sense strand and (ii) an RNA antisense strand complementary thereto, wherein the DNA sense strand is the 19-nucleotide sequence of SEQ ID NO: 68 or the 19-nucleotide sequence of SEQ ID NO: 109.

2. The double stranded oligonucleotide construct according to claim 1, wherein the double stranded oligonucleotide construct has a structure of Structural Formula (2) below:

Structural Formula (2)

A—X—S—Y—B
AS in Structural Formula (2), S represents the sense strand of the oligonucleotide according to claim 1, AS represents the antisense strand thereof, and A, B, X and Y are as defined in claim 1.

3. The double stranded oligonucleotide construct according to claim 2, wherein the double stranded oligonucleotide construct has a structure of Structural Formula (3) or Structural Formula (4) below:

Structural Formula (3)

A—X-5′ S 3′-Y—B
AS

Structural Formula (4)

A—X-3′ S 5′-Y—B
AS in Structural Formula (3) and Structural Formula (4), A, B, X, Y, S and AS are as defined in claim 2, and 5' and 3' represent a 5' end and a 3' end of the sense strand of the oligonucleotide.

4. The double stranded oligonucleotide construct according to claim 1, wherein the hydrophilic material has a molecular weight of 200 to 10,000.

5. The double stranded oligonucleotide construct according to claim 1, wherein the hydrophobic material has a molecular weight of 250 to 1,000.

6. The double stranded oligonucleotide construct according to claim 1, wherein the covalent bond represented by X and Y is a non-cleavable bond or a cleavable bond.

7. The double stranded oligonucleotide construct according to claim 6, wherein the non-cleavable bond is an amide bond or a phosphate bond.

8. The double stranded oligonucleotide construct according to claim 6, wherein the cleavable bond is a disulfide bond, an acid-cleavable bond, an ester bond, an anhydride bond, a biodegradable bond, or an enzyme-cleavable bond.

9. The double stranded oligonucleotide construct according to claim 1, wherein a ligand having a property of specifically binding to a receptor that promotes target cell internalization through receptor-mediated endocytosis (RME) is additionally bound to the hydrophilic material.

10. The double stranded oligonucleotide construct according to claim 9, wherein the ligand is selected from the group consisting of a target-receptor-specific antibody, aptamer, peptide, folate, N-acetyl galactosamine (NAG), glucose, and mannose.

11. The double stranded oligonucleotide construct according to claim 1, wherein an amine group or a polyhistidine group is additionally introduced at an end portion of the hydrophilic material opposite an end portion bound with the oligonucleotide.

12. The double stranded oligonucleotide construct according to claim 11, wherein the amine group or the polyhistidine group is connected to the hydrophilic material or to a hydrophilic block through at least one linker.

13. The double stranded oligonucleotide construct according to claim 1, wherein the hydrophilic material is polyethylene glycol (PEG), and the hydrophobic material is C24 containing a disulfide bond.

14. A nanoparticle comprising the double stranded oligonucleotide construct according to claim 1.

15. The nanoparticle according to claim 14, wherein double stranded oligonucleotide constructs comprising oligonucleotides having different sequences are mixed.

16. A composition for preventing hair loss or promoting hair growth, comprising the nanoparticle according to claim 14 as an active ingredient.

17. The composition according to claim 16, in a formulation selected from among ointment, paste, gel, jelly, serum, aerosol spray, non-aerosol spray, foam, cream, lotion, solution, and suspension formulations.

18. The composition according to claim 16, in a formulation selected from among hair tonic, hair conditioner, hair essence, hair lotion, hair nutrition lotion, hair shampoo, hair rinse, hair treatment, hair cream, hair nutrition cream, hair moisture cream, hair massage cream, hair wax, hair aerosol, hair pack, hair nutrition pack, hair soap, hair cleansing foam, hair oil, hair dryer, hair preservative, hair dye, hair wave agent, hair decolorant, hair gel, hair glaze, hair dressing, hair lacquer, hair moisturizer, hair mousse, and hair spray formulations.

19. A composition for preventing hair loss or promoting hair growth, comprising the double stranded oligonucleotide construct according to claim 1 as an active ingredient.

20. The composition according to claim 19, in a formulation selected from among ointment, paste, gel, jelly, serum, aerosol spray, non-aerosol spray, foam, cream, lotion, solution, and suspension formulations.

21. The composition according to claim 19, in a formulation selected from among hair tonic, hair conditioner, hair essence, hair lotion, hair nutrition lotion, hair shampoo, hair rinse, hair treatment, hair cream, hair nutrition cream, hair moisture cream, hair massage cream, hair wax, hair aerosol, hair pack, hair nutrition pack, hair soap, hair cleansing foam, hair oil, hair dryer, hair preservative, hair dye, hair wave agent, hair decolorant, hair gel, hair glaze, hair dressing, hair lacquer, hair moisturizer, hair mousse, and hair spray formulations.

* * * * *

SEQUENCE LISTING

```
<160> NUMBER OF SEQ ID NOS: 561

<210> SEQ ID NO 1
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 1

acugccaggg accauguuu                                               19


<210> SEQ ID NO 2
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 2

ugccagggac cauguuuug                                               19
```

-continued

<210> SEQ ID NO 3
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 3
ccagggacca uguuuugcc 19

<210> SEQ ID NO 4
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 4
agggaccaug uuuugccca 19

<210> SEQ ID NO 5
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 5
uuuugcccau ugacuauua 19

<210> SEQ ID NO 6
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 6
uugcccauug acuauuacu 19

<210> SEQ ID NO 7
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 7
auugacuauu acuuuccac 19

<210> SEQ ID NO 8
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 8
ugacuauuac uuuccaccc 19

<210> SEQ ID NO 9

-continued

<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 9
acuauuacuu uccacccca                                        19

<210> SEQ ID NO 10
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 10
uauuacuuuc caccccaga                                        19

<210> SEQ ID NO 11
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 11
agaagaccug ccugaucug                                        19

<210> SEQ ID NO 12
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 12
cuucuucaaa agagccgcu                                        19

<210> SEQ ID NO 13
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 13
cacuauugau aaauuccga                                        19

<210> SEQ ID NO 14
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 14
cuauugauaa auuccgaag                                        19

<210> SEQ ID NO 15
<211> LENGTH: 19

<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 15
auuguccauc uugucgucu 19

<210> SEQ ID NO 16
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 16
gucgucuucg gaaauguua 19

<210> SEQ ID NO 17
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 17
uucggaaaug uuaugaagc 19

<210> SEQ ID NO 18
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 18
aauguuauga agcagggau 19

<210> SEQ ID NO 19
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 19
cugacagugu cacacauug 19

<210> SEQ ID NO 20
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 20
gaaggcuaug aaugucagc 19

<210> SEQ ID NO 21
<211> LENGTH: 19
<212> TYPE: RNA

<213> ORGANISM: Artificial Sequence
<220> FEATURE:
<223> OTHER INFORMATION: SiRNA sense strand for targeting Adrogen
      Receptor

<400> SEQUENCE: 21
uagugugugc uggacacga 19

<210> SEQ ID NO 22
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 22
gugugugcug gacacgaca 19

<210> SEQ ID NO 23
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 23
aacaaccagc ccgacuccu 19

<210> SEQ ID NO 24
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 24
gcccgacucc uuugcagcc 19

<210> SEQ ID NO 25
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 25
ugcucucuag ccucaauga 19

<210> SEQ ID NO 26
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 26
gagagacagc uuguacacg 19

<210> SEQ ID NO 27
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 27
gcuuguacac guggucaag 19

<210> SEQ ID NO 28
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 28
uuguacacgu ggucaagug 19

<210> SEQ ID NO 29
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 29
guacacgugg ucaaguggg 19

<210> SEQ ID NO 30
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 30
acacgugguc aagugggcc 19

<210> SEQ ID NO 31
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 31
acguggucaa gugggccaa 19

<210> SEQ ID NO 32
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 32
ggucaagugg gccaaggcc 19

<210> SEQ ID NO 33
<211> LENGTH: 19
<212> TYPE: RNA
<213> ORGANISM: Artificial Sequence
<220> FEATURE:

```
<223> OTHER INFORMATION: SiRNA sense strand for targeting Adrogen
      Receptor

<400> SEQUENCE: 33

ccuggcuucc gcaacuuac                                                19


<210> SEQ ID NO 34
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 34

uggcuuccgc aacuuacac                                                19


<210> SEQ ID NO 35
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 35

gcuuccgcaa cuuacacgu                                                19


<210> SEQ ID NO 36
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 36

uuccgcaacu uacacgugg                                                19


<210> SEQ ID NO 37
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 37

ccgcaacuua cacguggac                                                19


<210> SEQ ID NO 38
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 38

gcaacuuaca cguggacga                                                19


<210> SEQ ID NO 39
<211> LENGTH: 19
<212> TYPE: RNA
<213> ORGANISM: Artificial Sequence
<220> FEATURE:
<223> OTHER INFORMATION: SiRNA sense strand for targeting Adrogen
```

Receptor

<400> SEQUENCE: 39
cacguggacg accagaugg 19

<210> SEQ ID NO 40
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 40
gacgaccaga uggcuguca 19

<210> SEQ ID NO 41
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 41
ucauucagua cuccuggau 19

<210> SEQ ID NO 42
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 42
gcucauggug uuugccaug 19

<210> SEQ ID NO 43
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 43
ccaugggcug gcgauccuu 19

<210> SEQ ID NO 44
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 44
uggcgauccu ucaccaaug 19

<210> SEQ ID NO 45
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 45
augucaacuc caggaugcu 19

<210> SEQ ID NO 46
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 46
acuccaggau gcucuacuu 19

<210> SEQ ID NO 47
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 47
caggaugcuc uacuucgcc 19

<210> SEQ ID NO 48
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 48
ggaugcucua cuucgcccc 19

<210> SEQ ID NO 49
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 49
augcucuacu ucgccccug 19

<210> SEQ ID NO 50
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 50
gcucuacuuc gccccugau 19

<210> SEQ ID NO 51
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 51
ucuacuucgc cccugaucu 19

<210> SEQ ID NO 52
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 52
uacuucgccc cugaucugg 19

<210> SEQ ID NO 53
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 53
cuucgccccu gaucugguu 19

<210> SEQ ID NO 54
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 54
ucgccccuga ucugguuuu 19

<210> SEQ ID NO 55
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 55
gccccugauc ugguuuuca 19

<210> SEQ ID NO 56
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 56
cccugaucug guuuucaau 19

<210> SEQ ID NO 57
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 57
ucaaugagua ccgcaugca 19

<210> SEQ ID NO 58
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 58
aaugaguacc gcaugcaca 19

<210> SEQ ID NO 59
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 59
uaccgcaugc acaaguccc 19

<210> SEQ ID NO 60
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 60
ccgcaugcac aaguccegg 19

<210> SEQ ID NO 61
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 61
gcaugcacaa gucccggau 19

<210> SEQ ID NO 62
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 62
cccggaugua cagccagug 19

<210> SEQ ID NO 63
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 63
cagccagugu guccgaaug 19

<210> SEQ ID NO 64
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 64
gccagugugu ccgaaugag 19

<210> SEQ ID NO 65
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 65
cagugugucc gaaugaggc 19

<210> SEQ ID NO 66
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 66
guguccgaau gaggcaccu 19

<210> SEQ ID NO 67
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 67
gaggcaccuc ucucaagag 19

<210> SEQ ID NO 68
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 68
gaguuuggau ggcuccaaa 19

<210> SEQ ID NO 69
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 69
cuccaaauca ccccccagg 19

<210> SEQ ID NO 70
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 70
ccaaaucacc ccccaggaa 19

<210> SEQ ID NO 71
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 71
auuccugugc augaaagca 19

<210> SEQ ID NO 72
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 72
ccaguggaug ggcugaaaa 19

<210> SEQ ID NO 73
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 73
aguggauggg cugaaaaau 19

<210> SEQ ID NO 74
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 74
augaacuucg aaugaacua 19

<210> SEQ ID NO 75
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 75
gaacuucgaa ugaacuaca 19

<210> SEQ ID NO 76
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 76
acuucgaaug aacuacauc 19

<210> SEQ ID NO 77
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 77
uucgaaugaa cuacaucaa 19

<210> SEQ ID NO 78
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 78
cgaaugaacu acaucaagg 19

<210> SEQ ID NO 79
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 79
aucaaggaac ucgaucgua 19

<210> SEQ ID NO 80
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 80
caaggaacuc gaucguauc 19

<210> SEQ ID NO 81
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 81
aggaacucga ucguaucau 19

-continued

<210> SEQ ID NO 82
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 82
gaacucgauc guaucauug 19

<210> SEQ ID NO 83
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 83
acucgaucgu aucauugca 19

<210> SEQ ID NO 84
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 84
ucgaucguau cauugcaug 19

<210> SEQ ID NO 85
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 85
gaucguauca uugcaugca 19

<210> SEQ ID NO 86
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 86
uccugcucaa gacgcuucu 19

<210> SEQ ID NO 87
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 87
cugcucaaga cgcuucuac 19

<210> SEQ ID NO 88

<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 88
acuccgugca gccuauugc 19

<210> SEQ ID NO 89
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 89
uccgugcagc cuauugcga 19

<210> SEQ ID NO 90
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 90
cgugcagccu auugcgaga 19

<210> SEQ ID NO 91
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 91
ugcagccuau ugcgagaga 19

<210> SEQ ID NO 92
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 92
cagccuauug cgagagagc 19

<210> SEQ ID NO 93
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 93
gccuauugcg agagagcug 19

<210> SEQ ID NO 94
<211> LENGTH: 19

<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 94
uuuugaccug cuaaucaag 19

<210> SEQ ID NO 95
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 95
cuaaucaagu cacacaugg 19

<210> SEQ ID NO 96
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 96
aagucacaca uggugagcg 19

<210> SEQ ID NO 97
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 97
gcguggacuu uccggaaau 19

<210> SEQ ID NO 98
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 98
uuuccggaaa ugauggcag 19

<210> SEQ ID NO 99
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 99
gaaagucaag cccaucuau 19

<210> SEQ ID NO 100
<211> LENGTH: 19
<212> TYPE: RNA

<213> ORGANISM: Artificial Sequence
<220> FEATURE:
<223> OTHER INFORMATION: SiRNA sense strand for targeting Adrogen
Receptor

<400> SEQUENCE: 100
aagucaagcc caucuauuu 19

<210> SEQ ID NO 101
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 101
cuguuauaac ucugcacua 19

<210> SEQ ID NO 102
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 102
guuauaacuc ugcacuacu 19

<210> SEQ ID NO 103
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 103
uauaacucug cacuacucc 19

<210> SEQ ID NO 104
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 104
ucugcacuac uccucugca 19

<210> SEQ ID NO 105
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 105
uuggggaauu uccucuauu 19

<210> SEQ ID NO 106
<211> LENGTH: 19
<212> TYPE: RNA
<213> ORGANISM: Artificial Sequence

```
<220> FEATURE:
<223> OTHER INFORMATION: SiRNA sense strand for targeting Adrogen
      Receptor

<400> SEQUENCE: 106

ggggaauuuc cucuauuga                                                19


<210> SEQ ID NO 107
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 107

auugauguac agucuguca                                                19


<210> SEQ ID NO 108
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 108

ugauguacag ucugucaug                                                19


<210> SEQ ID NO 109
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 109

auguacaguc ugucaugaa                                                19


<210> SEQ ID NO 110
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 110

guacagucug ucaugaaca                                                19


<210> SEQ ID NO 111
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 111

auucuauuug cugggcuuu                                                19


<210> SEQ ID NO 112
<211> LENGTH: 19
<212> TYPE: RNA
<213> ORGANISM: Artificial Sequence
<220> FEATURE:
```

<223> OTHER INFORMATION: SiRNA sense strand for targeting Adrogen Receptor

<400> SEQUENCE: 112
uucccucccu aucuaaccc 19

<210> SEQ ID NO 113
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 113
cccucccuau cuaacccuc 19

<210> SEQ ID NO 114
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 114
cucccuaucu aacccuccc 19

<210> SEQ ID NO 115
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 115
cccuaucuaa cccucccau 19

<210> SEQ ID NO 116
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 116
cuaucuaacc cucccaugg 19

<210> SEQ ID NO 117
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 117
cucccauggc accuucaga 19

<210> SEQ ID NO 118
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 118
cccauggcac cuucagacu 19

<210> SEQ ID NO 119
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 119
ccauuguggc uccuaucug 19

<210> SEQ ID NO 120
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 120
auuguggcuc cuaucugug 19

<210> SEQ ID NO 121
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 121
gcuccuaucu guguuuuga 19

<210> SEQ ID NO 122
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 122
cauauggccc agugucaag 19

<210> SEQ ID NO 123
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 123
uauggcccag ugucaaguu 19

<210> SEQ ID NO 124
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 124
uguuuacagc acuacucug 19

<210> SEQ ID NO 125
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 125
gccacacaaa cguuuacuu 19

<210> SEQ ID NO 126
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 126
uacuuaucuu augccacgg 19

<210> SEQ ID NO 127
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 127
cuuaucuuau gccacggga 19

<210> SEQ ID NO 128
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 128
augccacggg aaguuuaga 19

<210> SEQ ID NO 129
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 129
aaguuuagag agcuaagau 19

<210> SEQ ID NO 130
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 130
guuuagagag cuaagauua 19

<210> SEQ ID NO 131
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 131
uuagagagcu aagauuauc 19

<210> SEQ ID NO 132
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 132
agagagcuaa gauuaucug 19

<210> SEQ ID NO 133
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 133
gaggccaaua gugacgaga 19

<210> SEQ ID NO 134
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 134
gugacgagaa ggugaaaau 19

<210> SEQ ID NO 135
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 135
gacgagaagg ugaaaauug 19

<210> SEQ ID NO 136
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 136

```
ccauggggag uuacugauu                                                19


<210> SEQ ID NO 137
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 137

uccacgggag acuuuauuu                                                19


<210> SEQ ID NO 138
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 138

cacgggagac uuuauuuuc                                                19


<210> SEQ ID NO 139
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 139

ggcuauugcc auuagaggg                                                19


<210> SEQ ID NO 140
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 140

cuauugccau uagagggca                                                19


<210> SEQ ID NO 141
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 141

aaggagggca auggagcau                                                19


<210> SEQ ID NO 142
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 142
```

ggagggcaau ggagcauca 19

<210> SEQ ID NO 143
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 143
agggcaaugg agcaucagu 19

<210> SEQ ID NO 144
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 144
ggcaauggag caucaguac 19

<210> SEQ ID NO 145
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 145
aguaccugcc cacagccuu 19

<210> SEQ ID NO 146
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 146
gucccugggg gcuagacug 19

<210> SEQ ID NO 147
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 147
gggggcuaga cugcucaac 19

<210> SEQ ID NO 148
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 148
agcaauucau uauacugaa 19

<210> SEQ ID NO 149
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 149
gugcuuguug uugaaaauu 19

<210> SEQ ID NO 150
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 150
cugcauguua augccucac 19

<210> SEQ ID NO 151
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 151
ccuccaacuu cagauugac 19

<210> SEQ ID NO 152
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 152
uccaacuuca gauugacuu 19

<210> SEQ ID NO 153
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 153
uaagaccuuu gaacugaau 19

<210> SEQ ID NO 154
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 154
agaccuuuga acugaaugu 19

-continued

<210> SEQ ID NO 155
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 155
cuuggcgacu uccacagaa 19

<210> SEQ ID NO 156
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 156
uggcgacuuc cacagaaaa 19

<210> SEQ ID NO 157
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 157
ugaccacuga gaagaagga 19

<210> SEQ ID NO 158
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 158
caggucugcu uucucaugu 19

<210> SEQ ID NO 159
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 159
cucaugugug agucaggga 19

<210> SEQ ID NO 160
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 160
gacacugacu gaauaguua 19

<210> SEQ ID NO 161
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 161
aaacucucac ugccacuac 19

<210> SEQ ID NO 162
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 162
ucucacugcc acuaccuuu 19

<210> SEQ ID NO 163
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 163
acuccgugaa gccacaagc 19

<210> SEQ ID NO 164
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 164
ugaagccaca agcaccuua 19

<210> SEQ ID NO 165
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 165
cacaagcacc uuauguccu 19

<210> SEQ ID NO 166
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 166
uucuuuuggg cauguucac 19

<210> SEQ ID NO 167

<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 167
cuuuugggca uguucacag 19

<210> SEQ ID NO 168
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 168
ccaccaagaa gguuagcag 19

<210> SEQ ID NO 169
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 169
aagguuagca ggccaacag 19

<210> SEQ ID NO 170
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 170
gguuagcagg ccaacagcu 19

<210> SEQ ID NO 171
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 171
ucugacaucu aucuguaga 19

<210> SEQ ID NO 172
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 172
acaucuaucu guagaugcc 19

<210> SEQ ID NO 173
<211> LENGTH: 19

```
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 173

aucuaucugu agaugccag                                                   19


<210> SEQ ID NO 174
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 174

uaccaacucu cagaucgcu                                                   19


<210> SEQ ID NO 175
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 175

ccaacucuca gaucgcugg                                                   19


<210> SEQ ID NO 176
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 176

gaucgcugga gcccuuaga                                                   19


<210> SEQ ID NO 177
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 177

ccuuagacaa acuggaaag                                                   19


<210> SEQ ID NO 178
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 178

cagagaugau acccuccca                                                   19


<210> SEQ ID NO 179
<211> LENGTH: 19
<212> TYPE: RNA
```

<213> ORGANISM: Artificial Sequence
<220> FEATURE:
<223> OTHER INFORMATION: SiRNA sense strand for targeting Adrogen
      Receptor

<400> SEQUENCE: 179
ugauacccuc ccagcaagu 19

<210> SEQ ID NO 180
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 180
aaaggggcua cccagauca 19

<210> SEQ ID NO 181
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 181
gcuacccaga ucaggguug 19

<210> SEQ ID NO 182
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 182
cucaauuacc aggguggga 19

<210> SEQ ID NO 183
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 183
cuugucaccc agcauaucc 19

<210> SEQ ID NO 184
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 184
agccuaaagc cagauggac 19

<210> SEQ ID NO 185
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 185
ucugacauug cccauacuc 19

<210> SEQ ID NO 186
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 186
gagggaggcc aaaccauug 19

<210> SEQ ID NO 187
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 187
gggaggccaa accauugag 19

<210> SEQ ID NO 188
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 188
gaggccaaac cauugagac 19

<210> SEQ ID NO 189
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 189
uucuacagaa ccauggcuu 19

<210> SEQ ID NO 190
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 190
aaccauggcu ucuuucgga 19

<210> SEQ ID NO 191
<211> LENGTH: 19
<212> TYPE: RNA
<213> ORGANISM: Artificial Sequence
<220> FEATURE:

<223> OTHER INFORMATION: SiRNA sense strand for targeting Adrogen
      Receptor

<400> SEQUENCE: 191
cuucuuucgg aaaggucug 19

<210> SEQ ID NO 192
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 192
uuucggaaag gucugguug 19

<210> SEQ ID NO 193
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 193
uccaauacuu ugccaccca 19

<210> SEQ ID NO 194
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 194
augaacucag ggugugccc 19

<210> SEQ ID NO 195
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 195
agggugugcc cugggacac 19

<210> SEQ ID NO 196
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 196
cacugguuuu auauagucu 19

<210> SEQ ID NO 197
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 197
auagucuuuu ggcacaccu 19

<210> SEQ ID NO 198
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 198
agucuuuugg cacaccugu 19

<210> SEQ ID NO 199
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 199
uguucuguug acuucguuc 19

<210> SEQ ID NO 200
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 200
accuacuuuc ucaucuugg 19

<210> SEQ ID NO 201
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 201
ccuuacuuag cucuuaauc 19

<210> SEQ ID NO 202
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 202
agcucuuaau cucaucugu 19

<210> SEQ ID NO 203
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 203
uaaucucauc uguugaacu 19

<210> SEQ ID NO 204
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 204
aucucaucug uugaacuca 19

<210> SEQ ID NO 205
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 205
ucaagcugcc cauuuuaau 19

<210> SEQ ID NO 206
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 206
uuguugagag gauaguuuc 19

<210> SEQ ID NO 207
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 207
gugacaugau augauccac 19

<210> SEQ ID NO 208
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 208
ugauauuaau agccaaacg 19

<210> SEQ ID NO 209
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 209
auauuaauag ccaaacgaa 19

<210> SEQ ID NO 210
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 210
auuaauagcc aaacgaacu 19

<210> SEQ ID NO 211
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 211
uaauagccaa acgaacuuc 19

<210> SEQ ID NO 212
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 212
auagccaaac gaacuucaa 19

<210> SEQ ID NO 213
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 213
agccaaacga acuucaaaa 19

<210> SEQ ID NO 214
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 214
ccaaacgaac uucaaaaca 19

<210> SEQ ID NO 215
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 215
aaacgaacuu caaaacagc 19

<210> SEQ ID NO 216
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 216
agaggggaac cuaagauga 19

<210> SEQ ID NO 217
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 217
aggggaaccu aagaugagu 19

<210> SEQ ID NO 218
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 218
gggaaccuaa gaugaguaa 19

<210> SEQ ID NO 219
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 219
gaaccuaaga ugaguaaua 19

<210> SEQ ID NO 220
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 220
aguaauaugc caauccaag 19

<210> SEQ ID NO 221
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 221
uaauaugcca auccaagac 19

<210> SEQ ID NO 222
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 222
auaugccaau ccaagacug 19

<210> SEQ ID NO 223
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 223
acuaaagcug acagguucc 19

<210> SEQ ID NO 224
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 224
uuuggggugg gauagacau 19

<210> SEQ ID NO 225
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 225
auuauuacac aaucuggcu 19

<210> SEQ ID NO 226
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 226
uauuacacaa ucuggcuca 19

<210> SEQ ID NO 227
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 227
ucauguacag gaucacuuu 19

<210> SEQ ID NO 228
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 228
guuacacuag guuacauuu 19

<210> SEQ ID NO 229
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 229
uuaauagguc cuuuacauc 19

<210> SEQ ID NO 230
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 230
gugauacaca gauugaauu 19

<210> SEQ ID NO 231
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 231
auaucucucc uuguaaaua 19

<210> SEQ ID NO 232
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 232
auacuagaag cucuccuuu 19

<210> SEQ ID NO 233
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 233
acuagaagcu cuccuuuac 19

<210> SEQ ID NO 234
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 234
uggguuuccc aauugugac 19

<210> SEQ ID NO 235
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 235
agcaguguaa uuaaaagca 19

<210> SEQ ID NO 236
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 236
gcaacaacug gauuacucc 19

<210> SEQ ID NO 237
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 237
aacaacugga uuacuccaa 19

<210> SEQ ID NO 238
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 238
cuagggaaaa auagccuac 19

<210> SEQ ID NO 239
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 239
agggaaaaau agccuacac 19

<210> SEQ ID NO 240
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 240
agccuacaca agccuuuag 19

<210> SEQ ID NO 241
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 241
ccuacacaag ccuuuaggc 19

<210> SEQ ID NO 242
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 242
uacacaagcc uuuaggccu 19

<210> SEQ ID NO 243
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 243
cacaagccuu uaggccuac 19

<210> SEQ ID NO 244
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 244
caagccuuua ggccuacuc 19

<210> SEQ ID NO 245
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 245
ggguuugagu gaacaaagg 19

<210> SEQ ID NO 246

-continued

<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 246
uuuggccauu gauguucua 19

<210> SEQ ID NO 247
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 247
uggccauuga uguucuagc 19

<210> SEQ ID NO 248
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 248
uugcaugcgc ucugcucua 19

<210> SEQ ID NO 249
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 249
gcaugcgcuc ugcucuaca 19

<210> SEQ ID NO 250
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 250
augcgcucug cucuacaaa 19

<210> SEQ ID NO 251
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 251
ugcucuacaa acagaguug 19

<210> SEQ ID NO 252
<211> LENGTH: 19

<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 252
cucuacaaac agaguuggu 19

<210> SEQ ID NO 253
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 253
uaugguuggu auacuguac 19

<210> SEQ ID NO 254
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 254
gccacucaga cccacuuag 19

<210> SEQ ID NO 255
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 255
cacucagacc cacuuagcu 19

<210> SEQ ID NO 256
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 256
cacuuagcug gugagcuag 19

<210> SEQ ID NO 257
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 257
cuuagcuggu gagcuagaa 19

<210> SEQ ID NO 258
<211> LENGTH: 19
<212> TYPE: RNA

<213> ORGANISM: Artificial Sequence
<220> FEATURE:
<223> OTHER INFORMATION: SiRNA sense strand for targeting Adrogen
Receptor

<400> SEQUENCE: 258
aaguuggcag ugcucgaug 19

<210> SEQ ID NO 259
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 259
guuggcagug cucgaugug 19

<210> SEQ ID NO 260
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 260
ugcucgaugu ggacgaaga 19

<210> SEQ ID NO 261
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 261
cucgaugugg acgaagagu 19

<210> SEQ ID NO 262
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 262
ggacgaagag ugaggaaga 19

<210> SEQ ID NO 263
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 263
ucaaagaaaa gagucgugu 19

<210> SEQ ID NO 264
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 264
gcaguuucag cucucguuc 19

<210> SEQ ID NO 265
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 265
uuucagcucu cguucauug 19

<210> SEQ ID NO 266
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 266
agcucucguu cauugggca 19

<210> SEQ ID NO 267
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 267
cucucguuca uugggcagc 19

<210> SEQ ID NO 268
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 268
cucguucauu gggcagcuc 19

<210> SEQ ID NO 269
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 269
cguucauugg gcagcucgc 19

<210> SEQ ID NO 270
<211> LENGTH: 19
<212> TYPE: RNA
<213> ORGANISM: Artificial Sequence
<220> FEATURE:

<223> OTHER INFORMATION: SiRNA sense strand for targeting Adrogen
      Receptor

<400> SEQUENCE: 270
acaugggagu uguuggauu 19

<210> SEQ ID NO 271
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 271
uuuucuaugc cauaggcaa 19

<210> SEQ ID NO 272
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 272
uucuaugcca uaggcaaua 19

<210> SEQ ID NO 273
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 273
uacucugaga aagggauau 19

<210> SEQ ID NO 274
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 274
uugaaggacu gucauauau 19

<210> SEQ ID NO 275
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 275
uuuauguaug uucacuggc 19

<210> SEQ ID NO 276
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 276
uauguauguu cacuggcac 19

<210> SEQ ID NO 277
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 277
ggcacuaaaa aauauagag 19

<210> SEQ ID NO 278
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 278
aaaaaauaua gagagcuuc 19

<210> SEQ ID NO 279
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 279
gguugaaaaa uaaugugcu 19

<210> SEQ ID NO 280
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 280
ugaugcuaga gucccucuc 19

<210> SEQ ID NO 281
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 281
augcuagagu cccucucug 19

<210> SEQ ID NO 282
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 282
gucccucucu guccauacu 19

<210> SEQ ID NO 283
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 283
uagcaaguuu uauuugacu 19

<210> SEQ ID NO 284
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 284
agcuaacauu gagcuucaa 19

<210> SEQ ID NO 285
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 285
guuuguuuca uuaggcaca 19

<210> SEQ ID NO 286
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 286
uuguuucauu aggcacagc 19

<210> SEQ ID NO 287
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 287
cauuaggcac agcacagau 19

<210> SEQ ID NO 288
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 288
cagggcauaa aggcccagg 19

<210> SEQ ID NO 289
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 289
accaaagcug cauuucagg 19

<210> SEQ ID NO 290
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 290
ucaggagacu cucuccaga 19

<210> SEQ ID NO 291
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 291
cuccagacag cccaguaac 19

<210> SEQ ID NO 292
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 292
acagcccagu aacuacccg 19

<210> SEQ ID NO 293
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 293
agcccaguaa cuacccgag 19

<210> SEQ ID NO 294
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 294
cccaguaacu acccgagca 19

<210> SEQ ID NO 295
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 295
caguaacuac ccgagcaug 19

<210> SEQ ID NO 296
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 296
guaacuaccc gagcauggc 19

<210> SEQ ID NO 297
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 297
agaggcugac ugucuacga 19

<210> SEQ ID NO 298
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 298
aggcugacug ucuacgaau 19

<210> SEQ ID NO 299
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 299
gcugacuguc uacgaauua 19

<210> SEQ ID NO 300
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 300
ugacugucua cgaauuauc 19

<210> SEQ ID NO 301
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 301
acugucuacg aauuaucuu 19

<210> SEQ ID NO 302
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 302
uacgaauuau cuugugcca 19

<210> SEQ ID NO 303
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 303
cgaauuaucu ugugccagu 19

<210> SEQ ID NO 304
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 304
gguuuucaug uuugaccca 19

<210> SEQ ID NO 305
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 305
uuuucauguu ugacccacu 19

<210> SEQ ID NO 306
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 306
uucuaccccu gaugccuuu 19

<210> SEQ ID NO 307
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 307
uguaggcaga ucuguucuc 19

<210> SEQ ID NO 308
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 308
uaggcagauc uguucucac 19

<210> SEQ ID NO 309
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 309
gauuacauug uaccugcua 19

<210> SEQ ID NO 310
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 310
uuacauugua ccugcuaag 19

<210> SEQ ID NO 311
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 311
auuguaccug cuaagauac 19

<210> SEQ ID NO 312
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 312
aauucauaag ggcaggggg 19

<210> SEQ ID NO 313
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 313 ggggggagc aagcauuag 19

<210> SEQ ID NO 314
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 314
gggggagcaa gcauuagug 19

<210> SEQ ID NO 315
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 315
gggagcaagc auuagugcc 19

<210> SEQ ID NO 316
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 316
cucuuugaua agcugucca 19

<210> SEQ ID NO 317
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 317
uugauaagcu guccaaaga 19

<210> SEQ ID NO 318
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 318
acagacuaaa ggacucugc 19

<210> SEQ ID NO 319
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 319
cuggugacug acuuauaag 19

<210> SEQ ID NO 320
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 320
ggugacugac uuauaagag 19

<210> SEQ ID NO 321
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 321
acugacuuau aagagcuuu 19

<210> SEQ ID NO 322
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 322
auggguccuu cacuaagug 19

<210> SEQ ID NO 323
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 323
uuauaagcag aacuggcuu 19

<210> SEQ ID NO 324
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 324 uuucucuag uaguugcug 19

<210> SEQ ID NO 325

<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 325
cucuaguagu ugcugagca 19

<210> SEQ ID NO 326
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 326
gcaaauuguu gaagcucca 19

<210> SEQ ID NO 327
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 327
uguugaagcu ccaucauug 19

<210> SEQ ID NO 328
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 328
uugaagcucc aucauugca 19

<210> SEQ ID NO 329
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 329
gaagcuccau cauugcaug 19

<210> SEQ ID NO 330
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 330
agcuccauca uugcauggu 19

<210> SEQ ID NO 331
<211> LENGTH: 19

-continued

<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 331
cuccaucauu gcaugguug 19

<210> SEQ ID NO 332
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 332
ccaucauugc augguugga 19

<210> SEQ ID NO 333
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 333
aucauugcau gguuggaaa 19

<210> SEQ ID NO 334
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 334
agccacugug uuugcuagu 19

<210> SEQ ID NO 335
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 335
ugcuagugcc cauguuagc 19

<210> SEQ ID NO 336
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 336
cuagugccca uguuagcuu 19

<210> SEQ ID NO 337
<211> LENGTH: 19
<212> TYPE: RNA

<213> ORGANISM: Artificial Sequence
<220> FEATURE:
<223> OTHER INFORMATION: SiRNA sense strand for targeting Adrogen
Receptor

<400> SEQUENCE: 337
gcugauaagg gagcauuua 19

<210> SEQ ID NO 338
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 338
ugauaaggga gcauuuaaa 19

<210> SEQ ID NO 339
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 339
gggagcauuu aaaguacua 19

<210> SEQ ID NO 340
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 340
ggcacaaaaa guuaucugc 19

<210> SEQ ID NO 341
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 341
guuaucugca guugaaggc 19

<210> SEQ ID NO 342
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 342
guguguguuc ugauagcuu 19

<210> SEQ ID NO 343
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 343
ugagagagga ugcaguuuu 19

<210> SEQ ID NO 344
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 344
acaccuggau ugaucaguu 19

<210> SEQ ID NO 345
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 345
accuggauug aucaguuaa 19

<210> SEQ ID NO 346
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 346
cuggauugau caguuaacu 19

<210> SEQ ID NO 347
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 347
ggauugauca guuaacuaa 19

<210> SEQ ID NO 348
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 348
ugaucaguua acuaaaagu 19

<210> SEQ ID NO 349
<211> LENGTH: 19
<212> TYPE: RNA
<213> ORGANISM: Artificial Sequence
<220> FEATURE:

<223> OTHER INFORMATION: SiRNA sense strand for targeting Adrogen
      Receptor

<400> SEQUENCE: 349
aucaguuaac uaaaaguuu 19

<210> SEQ ID NO 350
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 350
caguuaacua aaaguuuuc 19

<210> SEQ ID NO 351
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 351
ccccuauugg guuugaccc 19

<210> SEQ ID NO 352
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 352
ccuauugggu uugacccac 19

<210> SEQ ID NO 353
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 353
ggguuugacc cacagguccc 19

<210> SEQ ID NO 354
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 354
agggauaaaa agaguagag 19

<210> SEQ ID NO 355
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 355
uagaggacau gauacauug 19

<210> SEQ ID NO 356
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 356
gaggacauga uacauugua 19

<210> SEQ ID NO 357
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 357
gauacauugu acuuuacua 19

<210> SEQ ID NO 358
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 358
uuuacuaguu caagacaga 19

<210> SEQ ID NO 359
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 359
cuaguucaag acagaugaa 19

<210> SEQ ID NO 360
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 360
ccuacccaag ugauugacc 19

<210> SEQ ID NO 361
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 361
auugaccagu ggcccccua 19

<210> SEQ ID NO 362
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 362
ugaccagugg cccccuaau 19

<210> SEQ ID NO 363
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 363
guggcccccu aaugggacc 19

<210> SEQ ID NO 364
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 364
cccuaauggg accugagcu 19

<210> SEQ ID NO 365
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 365
cuaaugggac cugagcugu 19

<210> SEQ ID NO 366
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 366
gggcaguuuc cugcauugg 19

<210> SEQ ID NO 367
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 367
gcauuggaac cuggagcaa 19

<210> SEQ ID NO 368
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 368
gaaccuggag caagcgcuc 19

<210> SEQ ID NO 369
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 369
ggagcaagcg cucuaucuu 19

<210> SEQ ID NO 370
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 370
agcaagcgcu cuaucuuuc 19

<210> SEQ ID NO 371
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 371
caagcgcucu aucuuucac 19

<210> SEQ ID NO 372
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 372
agcgcucuau cuuucacac 19

<210> SEQ ID NO 373
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 373
uucacacaaa uucccucac 19

<210> SEQ ID NO 374
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 374
cacacaaauu cccucaccu 19

<210> SEQ ID NO 375
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 375
ugaggugcuc uuguuacug 19

<210> SEQ ID NO 376
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 376
aggugcucuu guuacuggg 19

<210> SEQ ID NO 377
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 377
gugcucuugu uacugggug 19

<210> SEQ ID NO 378
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 378
gcucuuguua cuggguguc 19

<210> SEQ ID NO 379
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 379
uuguuacugg gugucugug 19

<210> SEQ ID NO 380
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 380
cugugugcug uaauucugg 19

<210> SEQ ID NO 381
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 381
gugugcugua auucugguu 19

<210> SEQ ID NO 382
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 382
uucucuguua aaacuuguc 19

<210> SEQ ID NO 383
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 383
aaacuuguca gaguacuag 19

<210> SEQ ID NO 384
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 384
acuugucaga guacuagaa 19

<210> SEQ ID NO 385
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 385
uugucagagu acuagaagu 19

<210> SEQ ID NO 386
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 386
guacuagaag uuguaucuc 19

<210> SEQ ID NO 387
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 387
uuguaucucu guaggugca 19

<210> SEQ ID NO 388
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 388
ugauuaagag auugacacu 19

<210> SEQ ID NO 389
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 389
auuaagagau ugacacuuc 19

<210> SEQ ID NO 390
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 390
uaagagauug acacuucug 19

<210> SEQ ID NO 391
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 391
acacuucugu ugccuagga 19

```
<210> SEQ ID NO 392
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 392

acuucuguug ccuaggacc                                                 19


<210> SEQ ID NO 393
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 393

uucuguugcc uaggaccuc                                                 19


<210> SEQ ID NO 394
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 394

cuguugccua ggaccuccc                                                 19


<210> SEQ ID NO 395
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 395

aggugaaggc agaaaaauc                                                 19


<210> SEQ ID NO 396
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 396

auuaguuacu ccucuucag                                                 19


<210> SEQ ID NO 397
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 397

uaguuacucc ucuucagac                                                 19
```

-continued

<210> SEQ ID NO 398
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 398
auuuggccag aaaguaggu 19

<210> SEQ ID NO 399
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 399
aguagguaau augcauuga 19

<210> SEQ ID NO 400
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 400
uagguaauau gcauugauu 19

<210> SEQ ID NO 401
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 401
gguaauaugc auugauugg 19

<210> SEQ ID NO 402
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 402
auaugcauug auuggcuuc 19

<210> SEQ ID NO 403
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 403
augcauugau uggcuucug 19

<210> SEQ ID NO 404

<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 404
uucaguauag caaggugcu 19

<210> SEQ ID NO 405
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 405
caguauagca aggugcuag 19

<210> SEQ ID NO 406
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 406
guauagcaag gugcuaggu 19

<210> SEQ ID NO 407
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 407
caaggugcua gguuuuuuc 19

<210> SEQ ID NO 408
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 408
cuuagaaugg guggcccuu 19

<210> SEQ ID NO 409
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 409
ucccacauaa gcuacuuaa 19

<210> SEQ ID NO 410
<211> LENGTH: 19

```
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 410

ccacauaagc uacuuaaca                                                19


<210> SEQ ID NO 411
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 411

cuuaacaaga uugucaugg                                                19


<210> SEQ ID NO 412
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 412

gagcugcaga uuccauugc                                                19


<210> SEQ ID NO 413
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 413

auugcccacc aaagacuag                                                19


<210> SEQ ID NO 414
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 414

guaugggaac cuguacucu                                                19


<210> SEQ ID NO 415
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 415

uuugcauuau cucacaacc                                                19


<210> SEQ ID NO 416
<211> LENGTH: 19
<212> TYPE: RNA
```

<213> ORGANISM: Artificial Sequence
<220> FEATURE:
<223> OTHER INFORMATION: SiRNA sense strand for targeting Adrogen
      Receptor

<400> SEQUENCE: 416
ugcauuaucu cacaaccuu 19

<210> SEQ ID NO 417
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 417
cauuaucuca caaccuuag 19

<210> SEQ ID NO 418
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 418
cacaaccuua gcccuuggu 19

<210> SEQ ID NO 419
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 419
caaccuuagc ccuuggugc 19

<210> SEQ ID NO 420
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 420
cuuagcccuu ggugcuaac 19

<210> SEQ ID NO 421
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 421
uagcccuugg ugcuaacug 19

<210> SEQ ID NO 422
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 422
uuggugcuaa cuguccuac 19

<210> SEQ ID NO 423
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 423
cuaacugucc uacagugaa 19

<210> SEQ ID NO 424
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 424
aacuguccua cagugaagu 19

<210> SEQ ID NO 425
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 425
gugaagugcc ugggggguu 19

<210> SEQ ID NO 426
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 426
gaagugccug gggguugu 19

<210> SEQ ID NO 427
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 427 ccugggggu uguccuauc 19

<210> SEQ ID NO 428
<211> LENGTH: 19
<212> TYPE: RNA
<213> ORGANISM: Artificial Sequence
<220> FEATURE:

-continued

<223> OTHER INFORMATION: SiRNA sense strand for targeting Adrogen
      Receptor

<400> SEQUENCE: 428 uggggguug uccuauccc                                                19

<210> SEQ ID NO 429
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 429 gggguuguc cuaucccau                                                19

<210> SEQ ID NO 430
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 430
ggguuguccu aucccauaa                                                19

<210> SEQ ID NO 431
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 431
guuguccuau cccauaagc                                                19

<210> SEQ ID NO 432
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 432
uguccuaucc cauaagcca                                                19

<210> SEQ ID NO 433
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 433
uccuauccca uaagccacu                                                19

<210> SEQ ID NO 434
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 434
gaaugaccca cgcaaaaaa 19

<210> SEQ ID NO 435
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 435 aaagucccccu cacaaccca 19

<210> SEQ ID NO 436
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 436
aguccccuca caacccagu 19

<210> SEQ ID NO 437
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 437
uccccucaca acccaguga 19

<210> SEQ ID NO 438
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 438
caacccagug acaccuuuc 19

<210> SEQ ID NO 439
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 439
acccagugac accuuucug 19

<210> SEQ ID NO 440
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 440
uccucuagac uggaacauu 19

<210> SEQ ID NO 441
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 441
cucuagacug gaacauuga 19

<210> SEQ ID NO 442
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 442
gggagugccu cagacauga 19

<210> SEQ ID NO 443
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 443
gagugccuca gacaugaca 19

<210> SEQ ID NO 444
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 444
gugccucaga caugacauu 19

<210> SEQ ID NO 445
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 445
agacuaugua aacagagau 19

<210> SEQ ID NO 446
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 446
uuuagauggg gcucauuuc 19

<210> SEQ ID NO 447
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 447
ucauuucuca cgguggcac 19

<210> SEQ ID NO 448
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 448
auuucucacg guggcacuu 19

<210> SEQ ID NO 449
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 449
ccagcuccaa gcgcuagug 19

<210> SEQ ID NO 450
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 450
agcuccaagc gcuaguguu 19

<210> SEQ ID NO 451
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 451
ccaagcgcua guguucugu 19

<210> SEQ ID NO 452
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 452
aagcgcuagu guucuguuc 19

<210> SEQ ID NO 453
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 453
ggaaucuuuu guugcucua 19

<210> SEQ ID NO 454
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 454
aaauggcaga aacuuguuu 19

<210> SEQ ID NO 455
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 455
aaugucaucc auuguguaa 19

<210> SEQ ID NO 456
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 456
aaauauuggc uuacugguc 19

<210> SEQ ID NO 457
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 457
auauuggcuu acuggucug 19

<210> SEQ ID NO 458
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 458
ccacaucccc uguuauggc 19

<210> SEQ ID NO 459
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 459
acauccccug uuauggcug 19

<210> SEQ ID NO 460
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 460
ccccuguuau ggcugcagg 19

<210> SEQ ID NO 461
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 461
ccuguuaugg cugcaggau 19

<210> SEQ ID NO 462
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 462
uguuauggcu gcaggaucg 19

<210> SEQ ID NO 463
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 463
cugcaggauc gaguuauug 19

<210> SEQ ID NO 464
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 464
gcaggaucga guuauuguu 19

<210> SEQ ID NO 465
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 465
aggaucgagu uauuguuaa 19

<210> SEQ ID NO 466
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 466
gaucgaguua uuguuaaca 19

<210> SEQ ID NO 467
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 467
auguccucuu aucauuguu 19

<210> SEQ ID NO 468
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 468
guccucuuau cauuguugu 19

<210> SEQ ID NO 469
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 469
gugcaguuag ggcugggaa 19

<210> SEQ ID NO 470
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 470
gggucuaccc ucggccgcc 19

<210> SEQ ID NO 471
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 471
ucuguuccag agcgugcgc 19

<210> SEQ ID NO 472
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 472
gugauccaga acccgggcc 19

<210> SEQ ID NO 473
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 473
cagcaaccuu cacagccgc 19

<210> SEQ ID NO 474
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 474
ggggcugccg cagcagcug 19

<210> SEQ ID NO 475
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 475
agacauccug agcgaggcc 19

<210> SEQ ID NO 476
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 476
cuccuucagc aacagcagc 19

<210> SEQ ID NO 477
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 477
ggcagcagca gcgggagag 19

<210> SEQ ID NO 478
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 478
ggacaauuac uuagggggc 19

<210> SEQ ID NO 479
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 479
uuacuuaggg ggcacuucg 19

<210> SEQ ID NO 480
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 480
ggcagugucg guguccaug 19

<210> SEQ ID NO 481
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 481
cagcuucggg gggauugca 19

<210> SEQ ID NO 482
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 482
ugcaaagguu cucugcuag 19

<210> SEQ ID NO 483

<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 483
agguucucug cuagacgac 19

<210> SEQ ID NO 484
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 484
gagcacugaa gauacugcu 19

<210> SEQ ID NO 485
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 485
gauacugcug aguauuccc 19

<210> SEQ ID NO 486
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 486
gggagguuac accaaaggg 19

<210> SEQ ID NO 487
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 487
ggcgagagcc uaggcugcu 19

<210> SEQ ID NO 488
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 488
guccggagca cuggacgag 19

<210> SEQ ID NO 489
<211> LENGTH: 19

-continued

<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 489
cuuuccacug gcucuggcc 19

<210> SEQ ID NO 490
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 490
gcuggagaac ccgcuggac 19

<210> SEQ ID NO 491
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 491
cccgcuggac uacggcagc 19

<210> SEQ ID NO 492
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 492
gaaggccagu uguauggac 19

<210> SEQ ID NO 493
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 493
ggccaguugu auggaccgu 19

<210> SEQ ID NO 494
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 494
aagcgaaaug ggccccugg 19

<210> SEQ ID NO 495
<211> LENGTH: 19
<212> TYPE: RNA

<213> ORGANISM: Artificial Sequence
<220> FEATURE:
<223> OTHER INFORMATION: SiRNA sense strand for targeting Adrogen
Receptor

<400> SEQUENCE: 495
gcgaaauggg ccccuggau 19

<210> SEQ ID NO 496
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 496
augggccccu ggauggaua 19

<210> SEQ ID NO 497
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 497
gcuucugggu gucacuaug 19

<210> SEQ ID NO 498
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 498
ggucuucuuc aaaagagcc 19

<210> SEQ ID NO 499
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 499
aagagccgcu gaagggaaa 19

<210> SEQ ID NO 500
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 500
gagccgcuga agggaaaca 19

<210> SEQ ID NO 501
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 501
gggaaacaga aguaccugu 19

<210> SEQ ID NO 502
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 502
acagaaguac cugugcgcc 19

<210> SEQ ID NO 503
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 503
guaccugugc gccagcaga 19

<210> SEQ ID NO 504
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 504
auuccgaagg aaaaauugu 19

<210> SEQ ID NO 505
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 505
ggaaaaauug uccaucuug 19

<210> SEQ ID NO 506
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 506
aaauugucca ucuugucgu 19

<210> SEQ ID NO 507
<211> LENGTH: 19
<212> TYPE: RNA
<213> ORGANISM: Artificial Sequence
<220> FEATURE:

<223> OTHER INFORMATION: SiRNA sense strand for targeting Adrogen
      Receptor

<400> SEQUENCE: 507
auuguccauc uugucgucu                                                    19

<210> SEQ ID NO 508
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 508
gcagggauga cucugggag                                                    19

<210> SEQ ID NO 509
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 509
gcugaagaaa cuugguaau                                                    19

<210> SEQ ID NO 510
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 510
gaaacuuggu aaucugaaa                                                    19

<210> SEQ ID NO 511
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 511
acuugguaau cugaaacua                                                    19

<210> SEQ ID NO 512
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 512
ggagaggcuu ccagcacca                                                    19

<210> SEQ ID NO 513
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 513
ggcuaugaau gucagccca 19

<210> SEQ ID NO 514
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 514
ugucagccca ucuuucuga 19

<210> SEQ ID NO 515
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 515
caaccagccc gacuccuuu 19

<210> SEQ ID NO 516
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 516
ccagcccgac uccuuugca 19

<210> SEQ ID NO 517
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 517
ugaacuggga gagagacag 19

<210> SEQ ID NO 518
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 518
cugggagaga gacagcuug 19

<210> SEQ ID NO 519
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 519
ggccuugccu ggcuuccgc 19

<210> SEQ ID NO 520
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 520
cuuacacgug gacgaccag 19

<210> SEQ ID NO 521
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 521
ugaguaccgc augcacaag 19

<210> SEQ ID NO 522
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 522
ugaggcaccu cucucaaga 19

<210> SEQ ID NO 523
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 523
gaguuuggau ggcuccaaa 19

<210> SEQ ID NO 524
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 524
uuccugugca ugaaagcac 19

<210> SEQ ID NO 525
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 525
agcacugcua cucuucagc 19

<210> SEQ ID NO 526
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 526
aaaucaaaaa uucuuugau 19

<210> SEQ ID NO 527
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 527
aucaaaaauu cuuugauga 19

<210> SEQ ID NO 528
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 528
aaauucuuug augaacuuc 19

<210> SEQ ID NO 529
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 529
auucuuugau gaacuucga 19

<210> SEQ ID NO 530
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 530
cuucgaauga acuacauca 19

<210> SEQ ID NO 531
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 531
ugaacuacau caaggaacu 19

<210> SEQ ID NO 532
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 532
cuacaucaag gaacucgau 19

<210> SEQ ID NO 533
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 533
aagaaaaaau cccacaucc 19

<210> SEQ ID NO 534
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 534
gaaaaaaucc cacauccug 19

<210> SEQ ID NO 535
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 535
aaaaucccac auccugcuc 19

<210> SEQ ID NO 536
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 536
aaucccacau ccugcucaa 19

<210> SEQ ID NO 537
<211> LENGTH: 19
<212> TYPE: RNA
<213> ORGANISM: Artificial Sequence
<220> FEATURE:
<223> OTHER INFORMATION: SiRNA sense strand for targeting Adrogen Receptor

<400> SEQUENCE: 537

```
ucccacaucc ugcucaaga                                                  19


<210> SEQ ID NO 538
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 538

gcuccuggac uccgugcag                                                  19


<210> SEQ ID NO 539
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 539

ucaagucaca cauggugag                                                  19


<210> SEQ ID NO 540
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 540

gucacacaug gugagcgug                                                  19


<210> SEQ ID NO 541
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 541

gugcccaaga uccuuucug                                                  19


<210> SEQ ID NO 542
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 542

gauccuuucu gggaaaguc                                                  19


<210> SEQ ID NO 543
<211> LENGTH: 19
<212> TYPE: RNA
<213> ORGANISM: Artificial Sequence
<220> FEATURE:
<223> OTHER INFORMATION: SiRNA sense strand for targeting Adrogen
      Receptor

<400> SEQUENCE: 543

agucaagccc aucuauuuc                                                  19
```

<210> SEQ ID NO 544
<211> LENGTH: 19
<212> TYPE: RNA
<213> ORGANISM: Artificial Sequence
<220> FEATURE:
<223> OTHER INFORMATION: SiRNA sense strand for targeting Adrogen
Receptor

<400> SEQUENCE: 544
gcccaucuau uuccacacc 19

<210> SEQ ID NO 545
<211> LENGTH: 19
<212> TYPE: DNA
<213> ORGANISM: Artificial Sequence
<220> FEATURE:
<223> OTHER INFORMATION: Synthetic construct

<400> SEQUENCE: 545
cttacgctga gtacttcga 19

<210> SEQ ID NO 546
<211> LENGTH: 129
<212> TYPE: DNA
<213> ORGANISM: Artificial Sequence
<220> FEATURE:
<223> OTHER INFORMATION: Synthetic construct

<400> SEQUENCE: 546
gatggatagc tactccggac cttacgggga catgcgtttg gagactgcca gggaccatgt 60
tttgcccatt gactattact ttccacccca gaagacctgc ctgatctgtg gagatgaagc 120
ttctgggtg 129

<210> SEQ ID NO 547
<211> LENGTH: 19
<212> TYPE: DNA
<213> ORGANISM: Artificial Sequence
<220> FEATURE:
<223> OTHER INFORMATION: Synthetic construct

<400> SEQUENCE: 547
ttggagactg ccagggacc 19

<210> SEQ ID NO 548
<211> LENGTH: 19
<212> TYPE: DNA
<213> ORGANISM: Artificial Sequence
<220> FEATURE:
<223> OTHER INFORMATION: Synthetic construct

<400> SEQUENCE: 548
ggagactgcc agggaccat 19

<210> SEQ ID NO 549
<211> LENGTH: 19
<212> TYPE: DNA
<213> ORGANISM: Artificial Sequence
<220> FEATURE:
<223> OTHER INFORMATION: Synthetic construct

<400> SEQUENCE: 549
agactgccag ggaccatgt 19

<210> SEQ ID NO 550
<211> LENGTH: 19
<212> TYPE: DNA
<213> ORGANISM: Artificial Sequence
<220> FEATURE:
<223> OTHER INFORMATION: Synthetic construct

<400> SEQUENCE: 550
actgccaggg accatgttt 19

<210> SEQ ID NO 551
<211> LENGTH: 19
<212> TYPE: DNA
<213> ORGANISM: Artificial Sequence
<220> FEATURE:
<223> OTHER INFORMATION: Synthetic construct

<400> SEQUENCE: 551
tgccagggac catgttttg 19

<210> SEQ ID NO 552
<211> LENGTH: 19
<212> TYPE: DNA
<213> ORGANISM: Artificial Sequence
<220> FEATURE:
<223> OTHER INFORMATION: Synthetic construct

<400> SEQUENCE: 552
ccagggacca tgttttgcc 19

<210> SEQ ID NO 553
<211> LENGTH: 19
<212> TYPE: DNA
<213> ORGANISM: Artificial Sequence
<220> FEATURE:
<223> OTHER INFORMATION: Synthetic construct

<400> SEQUENCE: 553
agggaccatg ttttgccca 19

<210> SEQ ID NO 554
<211> LENGTH: 19
<212> TYPE: DNA
<213> ORGANISM: Artificial Sequence
<220> FEATURE:
<223> OTHER INFORMATION: Synthetic construct

<400> SEQUENCE: 554
ggaccatgtt ttgcccatt 19

<210> SEQ ID NO 555
<211> LENGTH: 19
<212> TYPE: DNA
<213> ORGANISM: Artificial Sequence
<220> FEATURE:
<223> OTHER INFORMATION: Synthetic construct

<400> SEQUENCE: 555
accatgtttt gcccattga 19

<210> SEQ ID NO 556
<211> LENGTH: 19
<212> TYPE: DNA
<213> ORGANISM: Artificial Sequence
<220> FEATURE:
<223> OTHER INFORMATION: Synthetic construct

<400> SEQUENCE: 556
catgttttgc ccattgaag 19

<210> SEQ ID NO 557
<211> LENGTH: 19
<212> TYPE: DNA
<213> ORGANISM: Artificial Sequence
<220> FEATURE:
<223> OTHER INFORMATION: Synthetic construct

<400> SEQUENCE: 557
tgttttgccc attgaagct 19

<210> SEQ ID NO 558
<211> LENGTH: 19
<212> TYPE: DNA
<213> ORGANISM: Artificial Sequence
<220> FEATURE:
<223> OTHER INFORMATION: Synthetic construct

<400> SEQUENCE: 558
ttttgcccat tgaagcttc 19

<210> SEQ ID NO 559
<211> LENGTH: 19
<212> TYPE: DNA
<213> ORGANISM: Artificial Sequence
<220> FEATURE:
<223> OTHER INFORMATION: Synthetic construct

<400> SEQUENCE: 559
ttgcccattg aagcttctg 19

<210> SEQ ID NO 560
<211> LENGTH: 19
<212> TYPE: DNA
<213> ORGANISM: Artificial Sequence
<220> FEATURE:
<223> OTHER INFORMATION: Synthetic construct

<400> SEQUENCE: 560
gcccattgaa gcttctggg 19

<210> SEQ ID NO 561
<211> LENGTH: 19
<212> TYPE: DNA
<213> ORGANISM: Artificial Sequence
<220> FEATURE:
<223> OTHER INFORMATION: Synthetic construct

<400> SEQUENCE: 561
ccattgaagc ttctgggtg 19